US012144826B2

(12) United States Patent
Lim et al.

(10) Patent No.: US 12,144,826 B2
(45) Date of Patent: Nov. 19, 2024

(54) METHODS OF TREATING EGFRVIII EXPRESSING GLIOBLASTOMAS

(71) Applicant: The Regents of the University of California, Oakland, CA (US)

(72) Inventors: Wendell A. Lim, San Francisco, CA (US); Hideho Okada, San Francisco, CA (US); Kole T. Roybal, San Francisco, CA (US); Joseph H. Choe, San Francisco, CA (US); Payal B. Watchmaker, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1073 days.

(21) Appl. No.: 17/042,030

(22) PCT Filed: Apr. 4, 2019

(86) PCT No.: PCT/US2019/025846
§ 371 (c)(1),
(2) Date: Sep. 25, 2020

(87) PCT Pub. No.: WO2019/195586
PCT Pub. Date: Oct. 10, 2019

(65) Prior Publication Data
US 2021/0023138 A1    Jan. 28, 2021

Related U.S. Application Data

(60) Provisional application No. 62/654,012, filed on Apr. 6, 2018, provisional application No. 62/722,681, filed on Aug. 24, 2018.

(51) Int. Cl.
*A61K 35/17* (2015.01)
*A61P 35/00* (2006.01)
*C07K 14/71* (2006.01)
*C07K 14/725* (2006.01)

(52) U.S. Cl.
CPC .............. *A61K 35/17* (2013.01); *A61P 35/00* (2018.01); *C07K 14/7051* (2013.01); *C07K 14/71* (2013.01)

(58) Field of Classification Search
CPC .............. A61K 35/17; A61K 39/0011; A61K 2039/507; A61K 2039/5156; A61K 2039/5158; A61K 2039/585; C07K 14/7051; C07K 14/71
See application file for complete search history.

(56) References Cited

U.S. PATENT DOCUMENTS

| 9,493,568 | B2 | 11/2016 | Reilly et al. |
| 2016/0264665 | A1 | 9/2016 | Lim et al. |
| 2017/0210811 | A1 | 7/2017 | Wong et al. |
| 2017/0309025 | A1 | 10/2017 | O'Rourke et al. |
| 2018/0079812 | A1* | 3/2018 | Lim .............. C07K 16/30 |
| 2018/0085401 | A1 | 3/2018 | Wu et al. |
| 2021/0023136 | A1 | 1/2021 | Lim et al. |
| 2021/0023139 | A1 | 1/2021 | Lim et al. |

FOREIGN PATENT DOCUMENTS

| WO | WO 2014/130657 A1 | 8/2014 |
| WO | WO 2016/138034 A1 | 9/2016 |
| WO | WO 2017/025038 A1 | 2/2017 |
| WO | WO 2017/087723 A1 | 5/2017 |
| WO | 2017193059 | 11/2017 |
| WO | WO 2018/039247 A1 | 3/2018 |
| WO | WO 2019/195576 A1 | 10/2019 |
| WO | WO 2019/195596 A1 | 10/2019 |

OTHER PUBLICATIONS

Chow KK et al. T cells redirected to EphA2 for the immunotherapy of glioblastoma. Mol Ther. Mar. 2013;21(3):629-37. doi: 10.1038/mt.2012.210. Epub Oct. 16, 2012. PMID: 23070117; PMCID: PMC3589173 (Year: 2013).*
Chow et al., "T Cells Redirected to EphA2 for the Immunotherapy of Glioblastoma", Molecular Therapy, 2013, 21(3): 629-637.
Johnson et al. (2015) "Rational development and characterization of humanized anti-EGFR variant III chimeric antigen receptor T cells for glioblastoma" Science Translational Medicine, 7(275):1-16.
Sattiraju et al.(2017) "IL 13RA2 targeted alpha particle therapy against glioblastomas" Oncotarget, 8 (26): 42997-43007.
Montano et al. (2011) "Expression of EGFRvIII in Glioblastoma: Prognostic Significance Revisited", Neoplasia, 13 (12):1113-1121.
O'Rourke et al. (2017) "A single dose of peripherally infused EGFRvIII-directed CART cells mediates antigen loss and induces adaptive resistance in patients with recurrent glioblastoma" Science Translational Medicine, 9(399):1-15.
Migliorini et al. (2018) "CART-Cell Therapies in Glioblastoma: A First Look" Clinical Cancer Research, 24 (3): 535-540.
Cajal et al., "Beyond molecular tumor heterogeneity: protein synthesis takes control", Oncogene, 2018, 37(19): 2490-2501.
Ding et al., "Clonal evolution in relapsed acute myeloid leukemia revealed by whole genome sequencing", Nature, 2012, 481(7382): 506-510.
Gerlinger et al., "Genomic architecture and evolution of clear cell renal cell carcinomas defined by multiregion sequencing", Nat Genet., 2014, 46(3): 225-233.

(Continued)

*Primary Examiner* — Amy M Bunker
*Assistant Examiner* — Vyoma Shubham Tiwari
(74) *Attorney, Agent, or Firm* — James S. Keddie; Bozicevic, Field & Francis LLP

(57) ABSTRACT

Methods are provided for treating a subject for an EGFRvIII expressing glioblastoma. The methods of the present disclosure involve administering to the subject a molecular circuit that is primed by EGFRvIII to induce one or more encoded therapeutics specific for one or more antigens expressed by the glioblastoma. Nucleic acids containing sequences encoding all or portions of such circuits are also provided, as well as cells, expression cassettes and vectors that contain such nucleic acids. Also provided are kits for practicing the described methods.

8 Claims, 13 Drawing Sheets

Specification includes a Sequence Listing.

(56) References Cited

OTHER PUBLICATIONS

Kortum et al., "Targeted sequencing of refractory myeloma reveals a high incidence of mutations in CRBN and Ras pathway genes", Blood, 2016, 128(9): 1226-1233.
Landau et al., "Evolution and Impact of Subclonal Mutations in Chronic Lymphocytic Leukemia", Cell, 2013, 152: 714-726.
Liang et al., "Complex roles of the stroma in the intrinsic resistance to gemcitabine in pancreatic cancer: where we are and where we are going", Experimental & Molecular Medicine, 2017, 49: e406.
Lim et al., "The Principles of Engineering Immune Cells to Treat Cancer", Cell, 2017, 168(4): 724-740.
Rathore et al., "Radiomic MRI signature reveals three distinct subtypes of glioblastoma with different clinical and molecular characteristics, offering prognostic value beyond IDH1", Scientific Reports, 2018, 8: 5087.
Roybal et al., "Synthetic Immunology: Hacking Immune Cells to Expand Their Therapeutic Capabilities", Annu Rev Immunol, 2017, 35: 229-253.
Wang et al., "Clonal Evolution in Breast Cancer Revealed by Single Nucleus Genome Sequencing", Nature, 2014, 512(7513): 155-160.
Akhavan et al., "CAR T cells for brain tumors: Lessons learned and road ahead", Immunol Rev. Jul. 2019, 290(1): 60-84.
Yang et al., "T cells expressing NKG2D chimeric antigen receptors efficiently eliminate glioblastoma and cancer stem cells", Journal for Immuno Therapy of Cancer, 2019, 7:171, 13 pages.
Choi et al., "Engineering Chimeric Antigen Receptor T cells to Treat Glioblastoma", J Target Ther Cancer., Aug. 2017, 6(4): 22-25.
Dauth et al., "Extracellular Matrix Protein Expression Is Brain Region Dependent", The Journal of Comparative Neurology, 2016, 524:1309-1336.
Ferrerosa et al., "IMMU-14. Synnotch Chimeric Antigen Receptor (CAR) T-Cells as a Potential Treatment for Diffuse Intrinsic Pontine Glioma (DIPG)/Diffuse Midline Glioma (DMG)", Jun. 2022, 24(Suppl 1): i84, doi: 10.1093/neuonc/noac079.307.
Mao et al., "Updates on Chimeric Antigen Receptor-Mediated Glioblastoma Immunotherapy", Rhode Island Medical Journal, 2017, 100(6): 39-42.
Nakagawa et al., "Identification of glioblastoma-specific antigens expressed in patient-derived tumor cells as candidate targets for chimeric antigen receptor T cell therapy", Neuro-Oncology Advances, Nov. 15, 2022, 5(1): 1-9.
Nehama et al., "B7-H3-redirected chimeric antigen receptor T cells target glioblastoma and neurospheres", EBioMedicine, 2019, 47: 33-43.
Razpotnik et al., "Targeting Malignant Brain Tumors with Antibodies", Frontiers in Immunology, 2017, 8(1181), pp. 1-14.
Shraibman et al., "Identification of Tumor Antigens Among the HLA Peptidomes of Glioblastoma Tumors and Plasma", Molecular & Cellular Proteomics, Jun. 2019, 18(6): 1255-1268.
Szeto et al., "TCR Recognition of Peptide-MHC-I: Rule Makers and Breakers", International Journal of Molecular Sciences, Dec. 2020, 22(1):68, 26 pages.
Wang et al., "Identification of tumor-associated antigens and immune subtypes of lower-grade glioma and glioblastoma for mRNA vaccine development", Chinese Neurosurgical Journal, Oct. 28, 2022, 8:34, 14 pages.
Watchmaker et al., "EXTH-33. Priming of Synnotch CAR T Cells via CNS-Specific Antigen Allows Spatial and Temporal Regulation of CAR Expression, Effective Homing and Persistence of T Cells in the CNS", Neuro-Oncology, Nov. 2022, vol. 24, Issue Supplement_7, Nov. 2022, Page vii216, https://doi.org/10.1093/neuonc/noac209.831.
Wu et al., "Tumor antigens and immune subtypes of glioblastoma: the fundamentals of mRNA vaccine and individualized immunotherapy development", Journal of Big Data, Jul. 14, 2022, 9:92, 25 pages.
Yamada et al., "Molecular Cloning of Brevican, a Novel Brain Proteoglycanof the Aggrecadersican Family", The Journal of Biological Chemistry, 1994, 269(13): 10119-10126.
Yang et al., "Targeting EGFRvIII for glioblastoma multiforme", Cancer Letters, 2017, 403: 224-230.
Bielamowicz et al., "Trivalent CAR T cells overcome interpatient antigenic variability in glioblastoma", Neuro-Oncology, 2017, 20(4): 506-518.
Bielamowicz et al., "Trivalent CAR T cells overcome interpatient antigenic variability in glioblastoma", Neuro-Oncology, 2017, 20(4), Supplemental Tables 1-3.
Dutoit et al., "Exploiting the glioblastoma peptidome to discover novel tumour-associated antigens for immunotherapy", Brain, 2012, 135: 1042-1054.
Genbler et al., "Dual targeting of glioblastoma with chimeric antigen receptor-engineered natural killer cells overcomes heterogeneity of target antigen expression and enhances antitumor activity and survival", Oncoimmunology, 2016, 5(4): e1119354, 12 pages.
Hegde et al., "Combinational Targeting Offsets Antigen Escape and Enhances Effector Functions of Adoptively Transferred T Cells in Glioglastoma", Molecular Therapy, 2013, 21(11): 2087-2101.
Suryadevara et al., "Are BiTEs the "missing link" in cancer therapy?", Oncoimmunology, 2015, 4(6): e1008339, 10 pages.
Choe et al., "SynNotch-CAR T cells overcome challenges of specificity, heterogeneity, and persistence in treating glioblastoma", Science Translational Medicine, Apr. 28, 2021, 13, eabe7378, 15 pages.

\* cited by examiner

FIG. 4
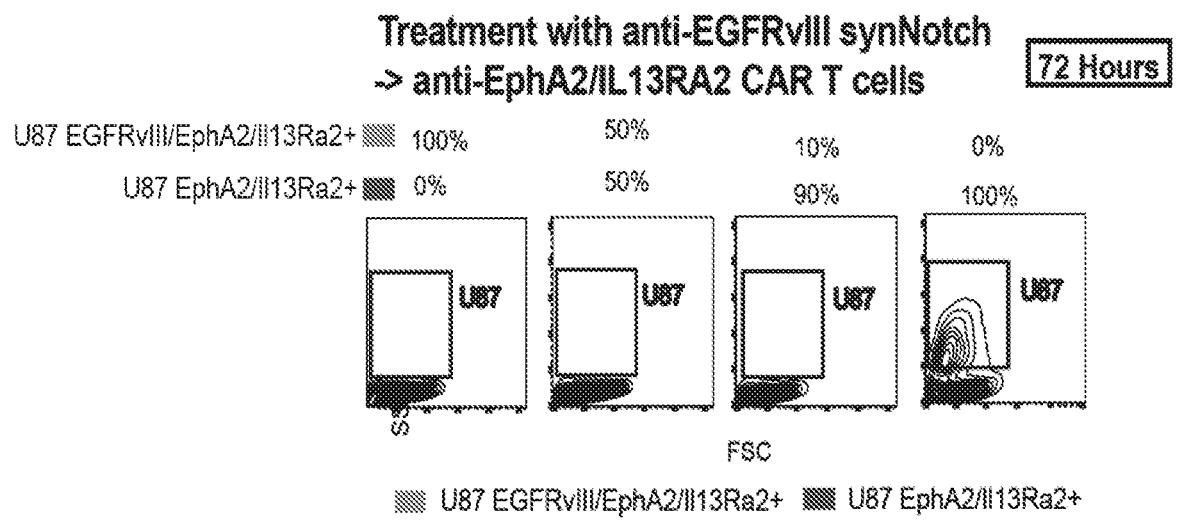
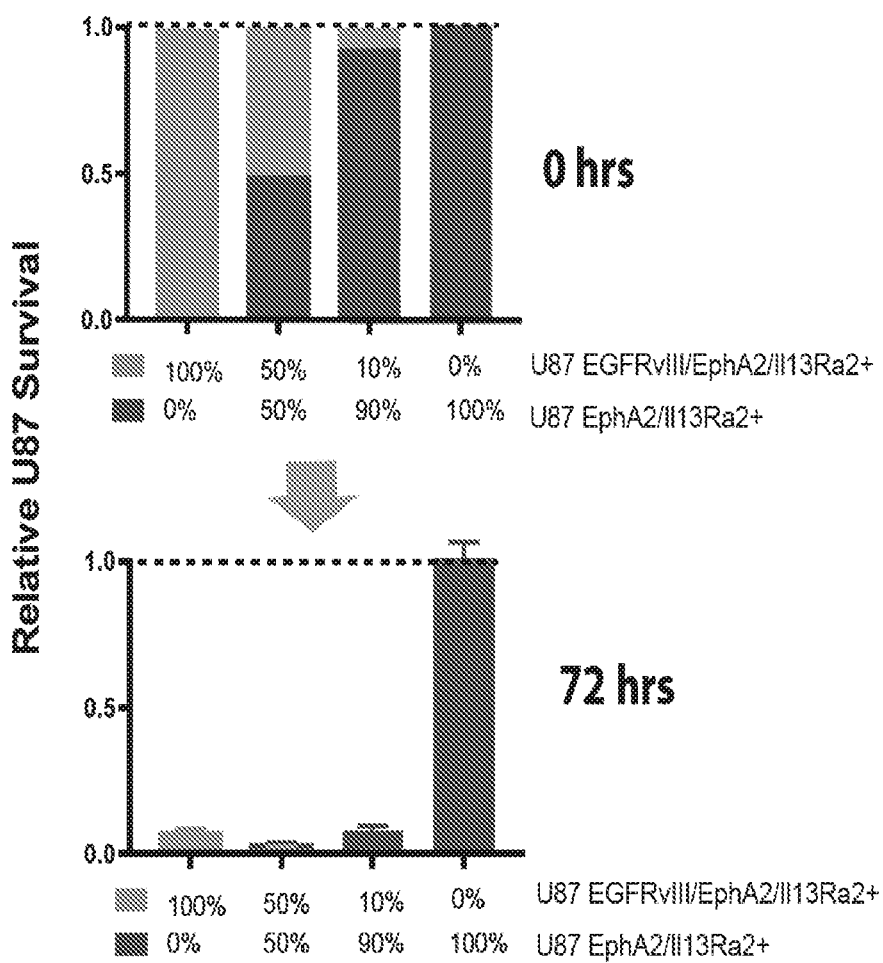

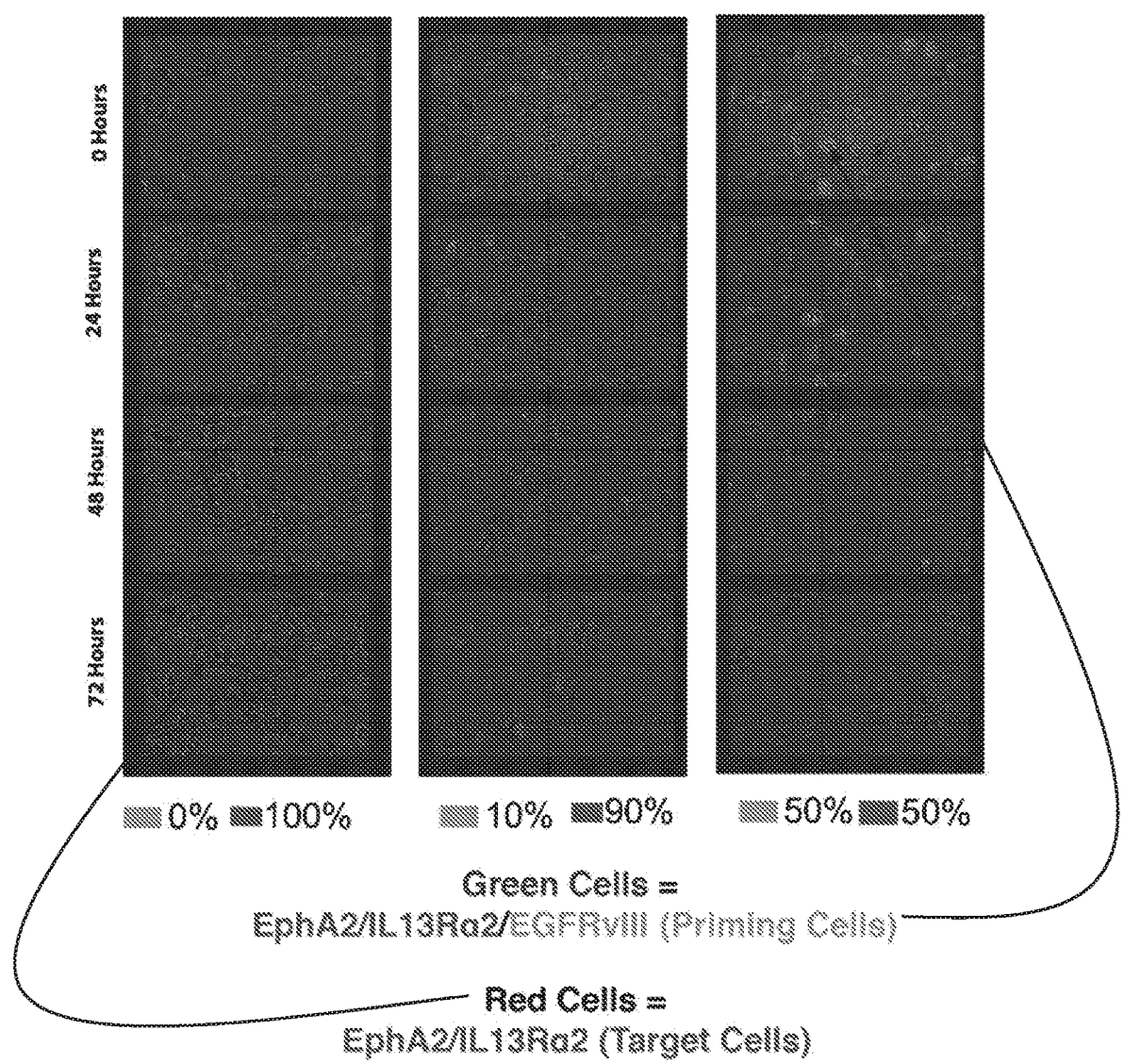

Glioblastoma - U87 Cell Line

FIG. 16
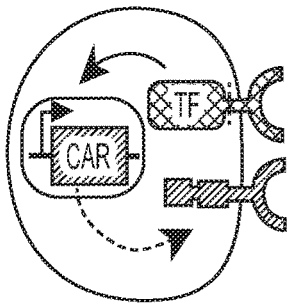
Antigen A
Antigen C
(A) and (C)
If A then kill C
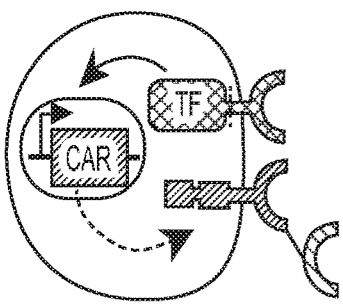
| Antigen A | Priming |
| Antigen C OR Antigen D | Killing |
(A) and (C or D)
If A then kill C or D
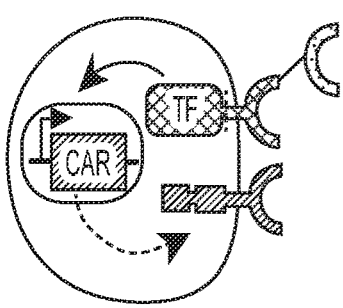
| Antigen A OR Antigen B | Priming |
| Antigen C | Killing |
(A or B) and (C)
If A or B then kill C
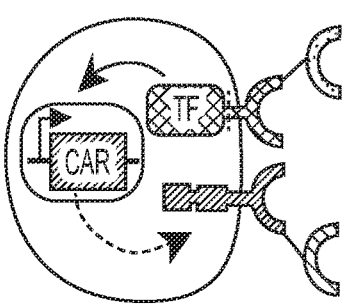
| Antigen A OR Antigen B | Priming |
| Antigen C OR Antigen D | Killing |
(A or B) and (C or D)
If A or B then kill C or D

SEQUENCE LISTING

<160> NUMBER OF SEQ ID NOS: 34

<210> SEQ ID NO 1
<211> LENGTH: 976
<212> TYPE: PRT
<213> ORGANISM: Homo sapiens

<400> SEQUENCE: 1

Met Glu Leu Gln Ala Ala Arg Ala Cys Phe Ala Leu Leu Trp Gly Cys
1               5                   10                  15

Ala Leu Ala Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

-continued

```
Tyr Met Tyr Ser Val Cys Asn Val Met Ser Gly Asp Gln Asp Asn Trp
 65                  70                  75                  80

Leu Arg Thr Asn Trp Val Tyr Arg Gly Glu Ala Glu Arg Ile Phe Ile
                 85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480
```

```
Ser Tyr Asn Val Arg Arg Thr Glu Gly Phe Ser Val Thr Leu Asp Asp
            485                 490                 495

Leu Ala Pro Asp Thr Thr Tyr Leu Val Gln Val Gln Ala Leu Thr Gln
        500                 505                 510

Glu Gly Gln Gly Ala Gly Ser Lys Val His Glu Phe Gln Thr Leu Ser
            515                 520                 525

Pro Glu Gly Ser Gly Asn Leu Ala Val Ile Gly Val Ala Val Gly
        530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
```

```
            900                 905                 910
Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
        930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 2
<211> LENGTH: 497
<212> TYPE: PRT
<213> ORGANISM: Homo sapiens

<400> SEQUENCE: 2

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300
```

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
450                 455                 460

Arg Val Trp Lys Tyr Glu Val Thr Tyr Arg Lys Lys Val Thr Pro Arg
465                 470                 475                 480

Gly Ala Gly Leu Ala Leu Ala Gly Pro Thr Ala Gly Asp Arg Leu Val
                485                 490                 495

Thr

<210> SEQ ID NO 3
<211> LENGTH: 253
<212> TYPE: PRT
<213> ORGANISM: Artificial sequence
<220> FEATURE:
<223> OTHER INFORMATION: synthetic polypeptide sequence

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr Gly Gly
            100                 105                 110

Gly Gly Ser Gly Ala Gly Gly Ser Gly Gly Gly Gly Thr Gly Gly Gly
        115                 120                 125

Gly Ser Glu Val Asp Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Arg Tyr Trp Met His Trp Val Arg Gln Ala Pro Gly Lys Gly Leu Glu

```
                    165                 170                 175

Trp Val Ser Ser Ile Ser Pro Tyr Asp Gly Glu Thr Asn Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Ile Ser Glu Trp Tyr Asn Trp Ala Val Asp Val Phe
225                 230                 235                 240

Asp Tyr Trp Gly Gln Gly Thr Leu Val Thr Val Ser Ser
                245                 250

<210> SEQ ID NO 4
<211> LENGTH: 237
<212> TYPE: PRT
<213> ORGANISM: Artificial sequence
<220> FEATURE:
<223> OTHER INFORMATION: synthetic polypeptide sequence

<400> SEQUENCE: 4

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Gln Ala Leu Glu Trp Met
        35                  40                  45

Gly Thr Ile Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Phe Thr Tyr Trp Gly Arg Gly Thr Leu Val Thr
            100                 105                 110

Ser Ser Gly Gly Gly Gly Ser Gly Gly Gly Ser Gly Gly Gly Gly
        115                 120                 125

Ser Asp Ile Gln Leu Thr Gln Ser Pro Ser Ser Leu Ser Ala Ser Val
    130                 135                 140

Gly Asp Arg Val Thr Ile Thr Cys Lys Ala Ser Gln Asp Ile Asn Asn
145                 150                 155                 160

Tyr Leu Ser Trp Tyr Gln Gln Lys Pro Gly Gln Ala Pro Arg Leu Leu
                165                 170                 175

Ile Tyr Arg Ala Asn Arg Leu Val Asp Gly Val Pro Asp Arg Phe Ser
            180                 185                 190

Gly Ser Gly Tyr Gly Thr Asp Phe Thr Leu Thr Ile Asn Asn Ile Glu
        195                 200                 205

Ser Glu Asp Ala Ala Tyr Tyr Phe Cys Leu Lys Tyr Asp Val Phe Pro
    210                 215                 220

Tyr Thr Phe Gly Gln Gly Thr Lys Val Glu Ile Lys Ser
225                 230                 235

<210> SEQ ID NO 5
<211> LENGTH: 983
<212> TYPE: PRT
<213> ORGANISM: Homo sapiens

<400> SEQUENCE: 5
```

```
Met Asp Cys Gln Leu Ser Ile Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
                35                  40                  45

Ser His Gly Trp Glu Glu Ile Ser Gly Val Asp Glu His Tyr Thr Pro
        50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
        130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
            245                 250                 255

Cys Ser Cys Asn Ala Gly Tyr Glu Glu Arg Gly Phe Met Cys Gln Ala
        260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
        290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
            325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
        355                 360                 365

Asn Ile Lys Gln Cys Glu Pro Cys Ser Pro Asn Val Arg Phe Leu Pro
        370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
            405                 410                 415
```

```
Glu Leu Ser Ser Pro Pro Arg Gln Phe Ala Val Ser Ile Thr Thr
            420                 425                 430

Asn Gln Ala Ala Pro Ser Pro Val Leu Thr Ile Lys Lys Asp Arg Thr
            435                 440                 445

Ser Arg Asn Ser Ile Ser Leu Ser Trp Gln Glu Pro Glu His Pro Asn
450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
            485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
            515                 520                 525

Ser Pro Asp Ser Phe Ser Ile Ser Gly Glu Ser Ser Gln Val Val Met
            530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
            565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
            595                 600                 605

Val His Glu Phe Ala Lys Glu Leu Asp Ala Thr Asn Ile Ser Ile Asp
            610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
            645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
            675                 680                 685

Val Thr Lys Ser Lys Pro Val Met Ile Val Thr Glu Tyr Met Glu Asn
            690                 695                 700

Gly Ser Leu Asp Ser Phe Leu Arg Lys His Asp Ala Gln Phe Thr Val
705                 710                 715                 720

Ile Gln Leu Val Gly Met Leu Arg Gly Ile Ala Ser Gly Met Lys Tyr
            725                 730                 735

Leu Ser Asp Met Gly Tyr Val His Arg Asp Leu Ala Ala Arg Asn Ile
            740                 745                 750

Leu Ile Asn Ser Asn Leu Val Cys Lys Val Ser Asp Phe Gly Leu Ser
            755                 760                 765

Arg Val Leu Glu Asp Asp Pro Glu Ala Ala Tyr Thr Thr Arg Gly Gly
            770                 775                 780

Lys Ile Pro Ile Arg Trp Thr Ser Pro Glu Ala Ile Ala Tyr Arg Lys
785                 790                 795                 800

Phe Thr Ser Ala Ser Asp Val Trp Ser Tyr Gly Ile Val Leu Trp Glu
            805                 810                 815

Val Met Ser Tyr Gly Glu Arg Pro Tyr Trp Glu Met Ser Asn Gln Asp
            820                 825                 830

Val Ile Lys Ala Val Asp Glu Gly Tyr Arg Leu Pro Pro Pro Met Asp
```

```
            835                 840                 845
Cys Pro Ala Ala Leu Tyr Gln Leu Met Leu Asp Cys Trp Gln Lys Asp
850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Thr Thr
            900                 905                 910

Phe Arg Thr Thr Gly Asp Trp Leu Asn Gly Val Trp Thr Ala His Cys
        915                 920                 925

Lys Glu Ile Phe Thr Gly Val Glu Tyr Ser Ser Cys Asp Thr Ile Ala
    930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

<210> SEQ ID NO 6
<211> LENGTH: 539
<212> TYPE: PRT
<213> ORGANISM: Homo sapiens

<400> SEQUENCE: 6

Met Asp Cys Gln Leu Ser Ile Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220
```

```
Glu Val Arg Gly Ser Cys Val Asn Asn Ser Lys Glu Asp Pro Pro
225                 230                 235                 240

Arg Met Tyr Cys Ser Thr Glu Gly Glu Trp Leu Val Pro Ile Gly Lys
            245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
            275                 280                 285

Lys Cys Pro Pro His Ser Ser Thr Gln Glu Asp Gly Ser Met Asn Cys
290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
            325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
            405                 410                 415

Glu Leu Ser Ser Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
435                 440                 445

Ser Arg Asn Ser Ile Ser Leu Ser Trp Gln Glu Pro Glu His Pro Asn
            450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
            485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
            515                 520                 525

Ser Pro Asp Cys Met Tyr Tyr Phe Asn Ala Val
530                 535

<210> SEQ ID NO 7
<211> LENGTH: 146
<212> TYPE: PRT
<213> ORGANISM: Homo sapiens

<400> SEQUENCE: 7

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
50                  55                  60
```

```
Ser Met Val Trp Ser Ile Asn Leu Thr Ala Gly Met Tyr Cys Ala Ala
 65                  70                  75                  80

Leu Glu Ser Leu Ile Asn Val Ser Gly Cys Ser Ala Ile Glu Lys Thr
                 85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Arg
130                 135                 140

Phe Asn
145

<210> SEQ ID NO 8
<211> LENGTH: 427
<212> TYPE: PRT
<213> ORGANISM: Homo sapiens

<400> SEQUENCE: 8

Met Glu Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
                 20                  25                  30

Pro Pro Val Thr Asn Leu Ser Val Ser Val Glu Asn Leu Cys Thr Val
                 35                  40                  45

Ile Trp Thr Trp Asn Pro Pro Glu Gly Ala Ser Ser Asn Cys Ser Leu
 50                  55                  60

Trp Tyr Phe Ser His Phe Gly Asp Lys Gln Asp Lys Lys Ile Ala Pro
 65                  70                  75                  80

Glu Thr Arg Arg Ser Ile Glu Val Pro Leu Asn Glu Arg Ile Cys Leu
                 85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
```

```
                275                 280                 285
Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
                340                 345                 350

Pro Val Ile Val Ala Gly Ala Ile Ile Val Leu Leu Leu Tyr Leu Lys
                355                 360                 365

Arg Leu Lys Ile Ile Ile Phe Pro Pro Ile Pro Asp Pro Gly Lys Ile
                370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
                420                 425

<210> SEQ ID NO 9
<211> LENGTH: 279
<212> TYPE: PRT
<213> ORGANISM: Homo sapiens

<400> SEQUENCE: 9

Met Glu Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
                20                  25                  30

Pro Pro Val Thr Asn Leu Ser Val Ser Val Glu Asn Leu Cys Thr Val
                35                  40                  45

Ile Trp Thr Trp Asn Pro Pro Glu Gly Ala Ser Ser Asn Cys Ser Leu
50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
                100                 105                 110

Leu Val Glu Lys Cys Ile Ser Pro Pro Glu Gly Asp Pro Glu Ser Ala
                115                 120                 125

Val Thr Glu Leu Gln Cys Ile Trp His Asn Leu Ser Tyr Met Lys Cys
                130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
                180                 185                 190

Lys Asp Ser Ser Phe Glu Gln His Ser Val Gln Ile Met Val Lys Asp
                195                 200                 205

Asn Ala Gly Lys Ile Lys Pro Ser Phe Asn Ile Val Pro Leu Thr Ser
                210                 215                 220
```

```
Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Arg Phe
            275

<210> SEQ ID NO 10
<211> LENGTH: 380
<212> TYPE: PRT
<213> ORGANISM: Homo sapiens

<400> SEQUENCE: 10

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
290                 295                 300

Cys Phe Val Val Arg Ser Lys Val Asn Ile Tyr Cys Ser Asp Asp Gly
305                 310                 315                 320
```

```
Ile Trp Ser Glu Trp Ser Asp Lys Gln Cys Trp Gly Glu Asp Leu
            325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Arg Lys Pro Asn Thr
            355                 360                 365

Tyr Pro Lys Met Ile Pro Glu Phe Phe Cys Asp Thr
            370                 375             380

<210> SEQ ID NO 11
<211> LENGTH: 122
<212> TYPE: PRT
<213> ORGANISM: Artificial sequence
<220> FEATURE:
<223> OTHER INFORMATION: synthetic polypeptide sequence

<400> SEQUENCE: 11

Leu Thr Cys Leu Gly Gly Phe Ala Ser Pro Gly Pro Val Pro Pro Ser
1               5                   10                  15

Thr Ala Leu Arg Lys Leu Ile Glu Glu Leu Val Asn Ile Thr Gln Asn
            20                  25                  30

Gln Lys Ala Pro Leu Cys Asn Gly Ser Met Val Trp Ser Ile Asn Leu
        35                  40                  45

Thr Ala Gly Met Tyr Cys Ala Ala Leu Glu Ser Leu Ile Asn Val Ser
    50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
            100                 105                 110

Arg Lys Leu Phe Arg Glu Gly Arg Phe Asn
        115                 120

<210> SEQ ID NO 12
<211> LENGTH: 1210
<212> TYPE: PRT
<213> ORGANISM: Homo sapiens

<400> SEQUENCE: 12

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125
```

```
Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
```

```
                    545                  550                 555                 560
                Glu Cys Leu Pro Gln Ala Met Asn Ile Thr Cys Thr Gly Arg Gly Pro
                                    565                 570                 575
                Asp Asn Cys Ile Gln Cys Ala His Tyr Ile Asp Gly Pro His Cys Val
                                    580                 585                 590
                Lys Thr Cys Pro Ala Gly Val Met Gly Glu Asn Asn Thr Leu Val Trp
                                    595                 600                 605
                Lys Tyr Ala Asp Ala Gly His Val Cys His Leu Cys His Pro Asn Cys
                                    610                 615                 620
                Thr Tyr Gly Cys Thr Gly Pro Gly Leu Glu Gly Cys Pro Thr Asn Gly
                625                 630                 635                 640
                Pro Lys Ile Pro Ser Ile Ala Thr Gly Met Val Gly Ala Leu Leu Leu
                                    645                 650                 655
                Leu Leu Val Val Ala Leu Gly Ile Gly Leu Phe Met Arg Arg His
                                660                 665                 670
                Ile Val Arg Lys Arg Thr Leu Arg Arg Leu Leu Gln Glu Arg Glu Leu
                                675                 680                 685
                Val Glu Pro Leu Thr Pro Ser Gly Glu Ala Pro Asn Gln Ala Leu Leu
                                690                 695                 700
                Arg Ile Leu Lys Glu Thr Glu Phe Lys Lys Ile Lys Val Leu Gly Ser
                705                 710                 715                 720
                Gly Ala Phe Gly Thr Val Tyr Lys Gly Leu Trp Ile Pro Glu Gly Glu
                                    725                 730                 735
                Lys Val Lys Ile Pro Val Ala Ile Lys Glu Leu Arg Glu Ala Thr Ser
                                    740                 745                 750
                Pro Lys Ala Asn Lys Glu Ile Leu Asp Glu Ala Tyr Val Met Ala Ser
                                    755                 760                 765
                Val Asp Asn Pro His Val Cys Arg Leu Leu Gly Ile Cys Leu Thr Ser
                                    770                 775                 780
                Thr Val Gln Leu Ile Thr Gln Leu Met Pro Phe Gly Cys Leu Leu Asp
                785                 790                 795                 800
                Tyr Val Arg Glu His Lys Asp Asn Ile Gly Ser Gln Tyr Leu Leu Asn
                                    805                 810                 815
                Trp Cys Val Gln Ile Ala Lys Gly Met Asn Tyr Leu Glu Asp Arg Arg
                                    820                 825                 830
                Leu Val His Arg Asp Leu Ala Ala Arg Asn Val Leu Val Lys Thr Pro
                                    835                 840                 845
                Gln His Val Lys Ile Thr Asp Phe Gly Leu Ala Lys Leu Leu Gly Ala
                                    850                 855                 860
                Glu Glu Lys Glu Tyr His Ala Glu Gly Gly Lys Val Pro Ile Lys Trp
                865                 870                 875                 880
                Met Ala Leu Glu Ser Ile Leu His Arg Ile Tyr Thr His Gln Ser Asp
                                    885                 890                 895
                Val Trp Ser Tyr Gly Val Thr Val Trp Glu Leu Met Thr Phe Gly Ser
                                    900                 905                 910
                Lys Pro Tyr Asp Gly Ile Pro Ala Ser Glu Ile Ser Ser Ile Leu Glu
                                    915                 920                 925
                Lys Gly Glu Arg Leu Pro Gln Pro Pro Ile Cys Thr Ile Asp Val Tyr
                                    930                 935                 940
                Met Ile Met Val Lys Cys Trp Met Ile Asp Ala Asp Ser Arg Pro Lys
                945                 950                 955                 960
                Phe Arg Glu Leu Ile Ile Glu Phe Ser Lys Met Ala Arg Asp Pro Gln
                                    965                 970                 975
```

```
Arg Tyr Leu Val Ile Gln Gly Asp Glu Arg Met His Leu Pro Ser Pro
                980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
    1010                1015                 1020

Phe Ser  Ser Pro Ser Thr Ser  Arg Thr Pro Leu Leu  Ser Ser Leu
    1025                1030                 1035

Ser Ala  Thr Ser Asn Asn Ser  Thr Val Ala Cys Ile  Asp Arg Asn
    1040                1045                 1050

Gly Leu  Gln Ser Cys Pro Ile  Lys Glu Asp Ser Phe  Leu Gln Arg
    1055                1060                 1065

Tyr Ser  Ser Asp Pro Thr Gly  Ala Leu Thr Glu Asp  Ser Ile Asp
    1070                1075                 1080

Asp Thr  Phe Leu Pro Val Pro  Glu Tyr Ile Asn Gln  Ser Val Pro
    1085                1090                 1095

Lys Arg  Pro Ala Gly Ser Val  Gln Asn Pro Val Tyr  His Asn Gln
    1100                1105                 1110

Pro Leu  Asn Pro Ala Pro Ser  Arg Asp Pro His Tyr  Gln Asp Pro
    1115                1120                 1125

His Ser  Thr Ala Val Gly Asn  Pro Glu Tyr Leu Asn  Thr Val Gln
    1130                1135                 1140

Pro Thr  Cys Val Asn Ser Thr  Phe Asp Ser Pro Ala  His Trp Ala
    1145                1150                 1155

Gln Lys  Gly Ser His Gln Ile  Ser Leu Asp Asn Pro  Asp Tyr Gln
    1160                1165                 1170

Gln Asp  Phe Phe Pro Lys Glu  Ala Lys Pro Asn Gly  Ile Phe Lys
    1175                1180                 1185

Gly Ser  Thr Ala Glu Asn Ala  Glu Tyr Leu Arg Val  Ala Pro Gln
    1190                1195                 1200

Ser Ser  Glu Phe Ile Gly Ala
    1205                1210

<210> SEQ ID NO 13
<211> LENGTH: 405
<212> TYPE: PRT
<213> ORGANISM: Homo sapiens

<400> SEQUENCE: 13

Met Arg Pro Ser Gly Thr Ala Gly Ala Ala Leu Leu Ala Leu Leu Ala
1                   5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
```

```
            115                 120                 125
Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Leu Ser
                405

<210> SEQ ID NO 14
<211> LENGTH: 705
<212> TYPE: PRT
<213> ORGANISM: Homo sapiens

<400> SEQUENCE: 14

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80
```

```
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Glu Ile Leu
130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Asn Cys Gln
            195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
```

```
                    500                 505                 510
Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 15
<211> LENGTH: 628
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160
```

-continued

```
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
    210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
```

```
              580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Ser
625

<210> SEQ ID NO 16
<211> LENGTH: 1255
<212> TYPE: PRT
<213> ORGANISM: Homo sapiens

<400> SEQUENCE: 16

Met Glu Leu Ala Ala Leu Cys Arg Trp Gly Leu Leu Leu Ala Leu Leu
1               5                  10                  15
Pro Pro Gly Ala Ala Ser Thr Gln Val Cys Thr Gly Thr Asp Met Lys
                20                  25                  30
Leu Arg Leu Pro Ala Ser Pro Glu Thr His Leu Asp Met Leu Arg His
            35                  40                  45
Leu Tyr Gln Gly Cys Gln Val Val Gln Gly Asn Leu Glu Leu Thr Tyr
        50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
        115                 120                 125
Val Thr Gly Ala Ser Pro Gly Gly Leu Arg Glu Leu Gln Leu Arg Ser
130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
        210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
        290                 295                 300
Ser Thr Asp Val Gly Ser Cys Thr Leu Val Cys Pro Leu His Asn Gln
305                 310                 315                 320
```

-continued

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile

```
                    740                 745                 750
Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
        1070                1075                1080

Asp Val Phe Asp Gly Asp Leu Gly Met Gly Ala Ala Lys Gly Leu
        1085                1090                1095

Gln Ser Leu Pro Thr His Asp Pro Ser Pro Leu Gln Arg Tyr Ser
        1100                1105                1110

Glu Asp Pro Thr Val Pro Leu Pro Ser Glu Thr Asp Gly Tyr Val
        1115                1120                1125

Ala Pro Leu Thr Cys Ser Pro Gln Pro Glu Tyr Val Asn Gln Pro
        1130                1135                1140

Asp Val Arg Pro Gln Pro Pro Ser Pro Arg Glu Gly Pro Leu Pro
        1145                1150                1155
```

```
Ala Ala Arg Pro Ala Gly Ala  Thr Leu Glu Arg Pro  Lys Thr Leu
        1160            1165                1170

Ser Pro Gly Lys Asn Gly Val  Val Lys Asp Val Phe  Ala Phe Gly
    1175            1180                1185

Gly Ala Val Glu Asn Pro Glu  Tyr Leu Thr Pro Gln  Gly Gly Ala
    1190            1195                1200

Ala Pro Gln Pro His Pro Pro  Ala Phe Ser Pro Ala  Phe Asp
    1205            1210                1215

Asn Leu Tyr Tyr Trp Asp Gln  Asp Pro Pro Glu Arg  Gly Ala Pro
    1220            1225                1230

Pro Ser Thr Phe Lys Gly Thr  Pro Thr Ala Glu Asn  Pro Glu Tyr
    1235            1240                1245

Leu Gly Leu Asp Val Pro Val
    1250            1255

<210> SEQ ID NO 17
<211> LENGTH: 645
<212> TYPE: PRT
<213> ORGANISM: Homo sapiens

<400> SEQUENCE: 17

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Ile Ser Ala Val
        35                  40                  45

Val Gly Ile Leu Leu Val Val Val Leu Gly Val Val Phe Gly Ile Leu
    50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
    130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
```

```
            260                 265                 270
Lys Val Pro Ile Lys Trp Met Ala Leu Glu Ser Ile Leu Arg Arg Arg
            275                 280                 285

Phe Thr His Gln Ser Asp Val Trp Ser Tyr Gly Val Thr Val Trp Glu
        290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335

Cys Thr Ile Asp Val Tyr Met Ile Met Val Lys Cys Trp Met Ile Asp
                340                 345                 350

Ser Glu Cys Arg Pro Arg Phe Arg Glu Leu Val Ser Glu Phe Ser Arg
            355                 360                 365

Met Ala Arg Asp Pro Gln Arg Phe Val Val Ile Gln Asn Glu Asp Leu
        370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
                420                 425                 430

Val His His Arg His Arg Ser Ser Thr Arg Ser Gly Gly Gly Asp
            435                 440                 445

Leu Thr Leu Gly Leu Glu Pro Ser Glu Glu Glu Ala Pro Arg Ser Pro
        450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
                485                 490                 495

Ser Pro Leu Gln Arg Tyr Ser Glu Asp Pro Thr Val Pro Leu Pro Ser
            500                 505                 510

Glu Thr Asp Gly Tyr Val Ala Pro Leu Thr Cys Ser Pro Gln Pro Glu
        515                 520                 525

Tyr Val Asn Gln Pro Asp Val Arg Pro Gln Pro Pro Ser Pro Arg Glu
        530                 535                 540

Gly Pro Leu Pro Ala Ala Arg Pro Ala Gly Ala Thr Leu Glu Arg Pro
545                 550                 555                 560

Lys Thr Leu Ser Pro Gly Lys Asn Gly Val Val Lys Asp Val Phe Ala
                565                 570                 575

Phe Gly Gly Ala Val Glu Asn Pro Glu Tyr Leu Thr Pro Gln Gly Gly
            580                 585                 590

Ala Ala Pro Gln Pro His Pro Pro Pro Ala Phe Ser Pro Ala Phe Asp
        595                 600                 605

Asn Leu Tyr Tyr Trp Asp Gln Asp Pro Pro Glu Arg Gly Ala Pro Pro
        610                 615                 620

Ser Thr Phe Lys Gly Thr Pro Thr Ala Glu Asn Pro Glu Tyr Leu Gly
625                 630                 635                 640

Leu Asp Val Pro Val
                645

<210> SEQ ID NO 18
<211> LENGTH: 569
<212> TYPE: PRT
<213> ORGANISM: Homo sapiens
```

<400> SEQUENCE: 18

```
Met Arg Arg Leu Leu Gln Glu Thr Glu Leu Val Glu Pro Leu Thr Pro
1               5                   10                  15

Ser Gly Ala Met Pro Asn Gln Ala Gln Met Arg Ile Leu Lys Glu Thr
            20                  25                  30

Glu Leu Arg Lys Val Lys Val Leu Gly Ser Gly Ala Phe Gly Thr Val
        35                  40                  45

Tyr Lys Gly Ile Trp Ile Pro Asp Gly Glu Asn Val Lys Ile Pro Val
50                  55                  60

Ala Ile Lys Val Leu Arg Glu Asn Thr Ser Pro Lys Ala Asn Lys Glu
65                  70                  75                  80

Ile Leu Asp Glu Ala Tyr Val Met Ala Gly Val Gly Ser Pro Tyr Val
                85                  90                  95

Ser Arg Leu Leu Gly Ile Cys Leu Thr Ser Thr Val Gln Leu Val Thr
            100                 105                 110

Gln Leu Met Pro Tyr Gly Cys Leu Leu Asp His Val Arg Glu Asn Arg
        115                 120                 125

Gly Arg Leu Gly Ser Gln Asp Leu Leu Asn Trp Cys Met Gln Ile Ala
130                 135                 140

Lys Gly Met Ser Tyr Leu Glu Asp Val Arg Leu Val His Arg Asp Leu
145                 150                 155                 160

Ala Ala Arg Asn Val Leu Val Lys Ser Pro Asn His Val Lys Ile Thr
                165                 170                 175

Asp Phe Gly Leu Ala Arg Leu Leu Asp Ile Asp Glu Thr Glu Tyr His
            180                 185                 190

Ala Asp Gly Gly Lys Val Pro Ile Lys Trp Met Ala Leu Glu Ser Ile
        195                 200                 205

Leu Arg Arg Arg Phe Thr His Gln Ser Asp Val Trp Ser Tyr Gly Val
210                 215                 220

Thr Val Trp Glu Leu Met Thr Phe Gly Ala Lys Pro Tyr Asp Gly Ile
225                 230                 235                 240

Pro Ala Arg Glu Ile Pro Asp Leu Leu Glu Lys Gly Glu Arg Leu Pro
                245                 250                 255

Gln Pro Pro Ile Cys Thr Ile Asp Val Tyr Met Ile Met Val Lys Cys
            260                 265                 270

Trp Met Ile Asp Ser Glu Cys Arg Pro Arg Phe Arg Glu Leu Val Ser
        275                 280                 285

Glu Phe Ser Arg Met Ala Arg Asp Pro Gln Arg Phe Val Val Ile Gln
290                 295                 300

Asn Glu Asp Leu Gly Pro Ala Ser Pro Leu Asp Ser Thr Phe Tyr Arg
305                 310                 315                 320

Ser Leu Leu Glu Asp Asp Asp Met Gly Asp Leu Val Asp Ala Glu Glu
                325                 330                 335

Tyr Leu Val Pro Gln Gln Gly Phe Phe Cys Pro Asp Pro Ala Pro Gly
            340                 345                 350

Ala Gly Gly Met Val His His Arg His Arg Ser Ser Ser Thr Arg Ser
        355                 360                 365

Gly Gly Gly Asp Leu Thr Leu Gly Leu Glu Pro Ser Glu Glu Glu Ala
370                 375                 380

Pro Arg Ser Pro Leu Ala Pro Ser Glu Gly Ala Gly Ser Asp Val Phe
385                 390                 395                 400

Asp Gly Asp Leu Gly Met Gly Ala Ala Lys Gly Leu Gln Ser Leu Pro
```

```
            405                 410                 415
Thr His Asp Pro Ser Pro Leu Gln Arg Tyr Ser Glu Asp Pro Thr Val
            420                 425                 430

Pro Leu Pro Ser Glu Thr Asp Gly Tyr Val Ala Pro Leu Thr Cys Ser
            435                 440                 445

Pro Gln Pro Glu Tyr Val Asn Gln Pro Asp Val Arg Pro Gln Pro Pro
        450                 455                 460

Ser Pro Arg Glu Gly Pro Leu Pro Ala Ala Arg Pro Ala Gly Ala Thr
465                 470                 475                 480

Leu Glu Arg Pro Lys Thr Leu Ser Pro Gly Lys Asn Gly Val Val Lys
                485                 490                 495

Asp Val Phe Ala Phe Gly Gly Ala Val Glu Asn Pro Glu Tyr Leu Thr
            500                 505                 510

Pro Gln Gly Gly Ala Ala Pro Gln Pro His Pro Pro Pro Ala Phe Ser
            515                 520                 525

Pro Ala Phe Asp Asn Leu Tyr Tyr Trp Asp Gln Asp Pro Pro Glu Arg
        530                 535                 540

Gly Ala Pro Pro Ser Thr Phe Lys Gly Thr Pro Thr Ala Glu Asn Pro
545                 550                 555                 560

Glu Tyr Leu Gly Leu Asp Val Pro Val
                565
```

<210> SEQ ID NO 19
<211> LENGTH: 1240
<212> TYPE: PRT
<213> ORGANISM: Homo sapiens

<400> SEQUENCE: 19

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205
```

```
Cys Ala Arg Cys Lys Gly Pro Leu Pro Thr Asp Cys His Glu Gln
210                 215                 220

Cys Ala Ala Gly Cys Thr Gly Pro Lys His Ser Asp Cys Leu Ala Cys
225             230                 235                 240

Leu His Phe Asn His Ser Gly Ile Cys Glu Leu His Cys Pro Ala Leu
            245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
            275                 280                 285

Leu Ser Thr Asp Val Gly Ser Cys Thr Leu Val Cys Pro Leu His Asn
290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
            355                 360                 365

Asp Pro Ala Ser Asn Thr Ala Pro Leu Gln Pro Glu Gln Leu Gln Val
370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
            435                 440                 445

Gly Leu Ala Leu Ile His His Asn Thr His Leu Cys Phe Val His Thr
450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
            515                 520                 525

Cys Arg Val Leu Gln Gly Leu Pro Arg Glu Tyr Val Asn Ala Arg His
530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
            595                 600                 605

Gln Pro Cys Pro Ile Asn Cys Thr His Ser Cys Val Asp Leu Asp Asp
610                 615                 620

Lys Gly Cys Pro Ala Glu Gln Arg Ala Ser Pro Leu Thr Ser Ile Ile
```

```
                625                 630                 635                 640
            Ser Ala Val Val Gly Ile Leu Val Val Leu Gly Val Val Phe
                            645                 650                 655

Gly Ile Leu Ile Lys Arg Arg Gln Gln Lys Ile Arg Lys Tyr Thr Met
                            660                 665                 670

Arg Arg Leu Leu Gln Glu Thr Glu Leu Val Glu Pro Leu Thr Pro Ser
                            675                 680                 685

Gly Ala Met Pro Asn Gln Ala Gln Met Arg Ile Leu Lys Glu Thr Glu
                            690                 695                 700

Leu Arg Lys Val Lys Val Leu Gly Ser Gly Ala Phe Gly Thr Val Tyr
            705                 710                 715                 720

Lys Gly Ile Trp Ile Pro Asp Gly Glu Asn Val Lys Ile Pro Val Ala
                            725                 730                 735

Ile Lys Val Leu Arg Glu Asn Thr Ser Pro Lys Ala Asn Lys Glu Ile
                            740                 745                 750

Leu Asp Glu Ala Tyr Val Met Ala Gly Val Gly Ser Pro Tyr Val Ser
                            755                 760                 765

Arg Leu Leu Gly Ile Cys Leu Thr Ser Thr Val Gln Leu Val Thr Gln
                            770                 775                 780

Leu Met Pro Tyr Gly Cys Leu Leu Asp His Val Arg Glu Asn Arg Gly
            785                 790                 795                 800

Arg Leu Gly Ser Gln Asp Leu Leu Asn Trp Cys Met Gln Ile Ala Lys
                            805                 810                 815

Gly Met Ser Tyr Leu Glu Asp Val Arg Leu Val His Arg Asp Leu Ala
                            820                 825                 830

Ala Arg Asn Val Leu Val Lys Ser Pro Asn His Val Lys Ile Thr Asp
                            835                 840                 845

Phe Gly Leu Ala Arg Leu Leu Asp Ile Asp Glu Thr Glu Tyr His Ala
                            850                 855                 860

Asp Gly Gly Lys Val Pro Ile Lys Trp Met Ala Leu Glu Ser Ile Leu
            865                 870                 875                 880

Arg Arg Arg Phe Thr His Gln Ser Asp Val Trp Ser Tyr Gly Val Thr
                            885                 890                 895

Val Trp Glu Leu Met Thr Phe Gly Ala Lys Pro Tyr Asp Gly Ile Pro
                            900                 905                 910

Ala Arg Glu Ile Pro Asp Leu Leu Glu Lys Gly Glu Arg Leu Pro Gln
                            915                 920                 925

Pro Pro Ile Cys Thr Ile Asp Val Tyr Met Ile Met Val Lys Cys Trp
                            930                 935                 940

Met Ile Asp Ser Glu Cys Arg Pro Arg Phe Arg Glu Leu Val Ser Glu
            945                 950                 955                 960

Phe Ser Arg Met Ala Arg Asp Pro Gln Arg Phe Val Val Ile Gln Asn
                            965                 970                 975

Glu Asp Leu Gly Pro Ala Ser Pro Leu Asp Ser Thr Phe Tyr Arg Ser
                            980                 985                 990

Leu Leu Glu Asp Asp Asp Met Gly Asp Leu Val Asp Ala Glu Glu Tyr
                            995                 1000                1005

Leu Val Pro Gln Gln Gly Phe Phe Cys Pro Asp Pro Ala Pro Gly
                            1010                1015                1020

Ala Gly Gly Met Val His His Arg His Arg Ser Ser Ser Thr Arg
                            1025                1030                1035

Ser Gly Gly Gly Asp Leu Thr Leu Gly Leu Glu Pro Ser Glu Glu
                            1040                1045                1050
```

```
Glu Ala Pro Arg Ser Pro Leu Ala Pro Ser Glu Gly Ala Gly Ser
    1055                1060                1065

Asp Val Phe Asp Gly Asp Leu Gly Met Gly Ala Ala Lys Gly Leu
    1070                1075                1080

Gln Ser Leu Pro Thr His Asp Pro Ser Pro Leu Gln Arg Tyr Ser
    1085                1090                1095

Glu Asp Pro Thr Val Pro Leu Pro Ser Glu Thr Asp Gly Tyr Val
    1100                1105                1110

Ala Pro Leu Thr Cys Ser Pro Gln Pro Glu Tyr Val Asn Gln Pro
    1115                1120                1125

Asp Val Arg Pro Gln Pro Pro Ser Pro Arg Glu Gly Pro Leu Pro
    1130                1135                1140

Ala Ala Arg Pro Ala Gly Ala Thr Leu Glu Arg Pro Lys Thr Leu
    1145                1150                1155

Ser Pro Gly Lys Asn Gly Val Val Lys Asp Val Phe Ala Phe Gly
    1160                1165                1170

Gly Ala Val Glu Asn Pro Glu Tyr Leu Thr Pro Gln Gly Gly Ala
    1175                1180                1185

Ala Pro Gln Pro His Pro Pro Pro Ala Phe Ser Pro Ala Phe Asp
    1190                1195                1200

Asn Leu Tyr Tyr Trp Asp Gln Asp Pro Pro Glu Arg Gly Ala Pro
    1205                1210                1215

Pro Ser Thr Phe Lys Gly Thr Pro Thr Ala Glu Asn Pro Glu Tyr
    1220                1225                1230

Leu Gly Leu Asp Val Pro Val
    1235                1240

<210> SEQ ID NO 20
<211> LENGTH: 1225
<212> TYPE: PRT
<213> ORGANISM: Homo sapiens

<400> SEQUENCE: 20

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
                20                  25                  30

Thr Tyr Leu Pro Thr Asn Ala Ser Leu Ser Phe Leu Gln Asp Ile Gln
            35                  40                  45

Glu Val Gln Gly Tyr Val Leu Ile Ala His Asn Gln Val Arg Gln Val
        50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
```

```
                    165                 170                 175
Glu Ser Ser Glu Asp Cys Gln Ser Leu Thr Arg Thr Val Cys Ala Gly
                180                 185                 190

Gly Cys Ala Arg Cys Lys Gly Pro Leu Pro Thr Asp Cys Cys His Glu
                195                 200                 205

Gln Cys Ala Ala Gly Cys Thr Gly Pro Lys His Ser Asp Cys Leu Ala
                210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
                260                 265                 270

Tyr Leu Ser Thr Asp Val Gly Ser Cys Thr Leu Val Cys Pro Leu His
                275                 280                 285

Asn Gln Glu Val Thr Ala Glu Asp Gly Thr Gln Arg Cys Glu Lys Cys
                290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
                340                 345                 350

Gly Asp Pro Ala Ser Asn Thr Ala Pro Leu Gln Pro Glu Gln Leu Gln
                355                 360                 365

Val Phe Glu Thr Leu Glu Glu Ile Thr Gly Tyr Leu Tyr Ile Ser Ala
                370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
                420                 425                 430

Ser Gly Leu Ala Leu Ile His His Asn Thr His Leu Cys Phe Val His
                435                 440                 445

Thr Val Pro Trp Asp Gln Leu Phe Arg Asn Pro His Gln Ala Leu Leu
                450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
                500                 505                 510

Glu Cys Arg Val Leu Gln Gly Leu Pro Arg Glu Tyr Val Asn Ala Arg
                515                 520                 525

His Cys Leu Pro Cys His Pro Glu Cys Gln Pro Gln Asn Gly Ser Val
                530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
                580                 585                 590
```

-continued

```
Cys Gln Pro Cys Pro Ile Asn Cys Thr His Ser Cys Val Asp Leu Asp
        595                 600                 605
Asp Lys Gly Cys Pro Ala Glu Gln Arg Ala Ser Pro Leu Thr Ser Ile
610                 615                 620
Ile Ser Ala Val Val Gly Ile Leu Leu Val Val Val Leu Gly Val Val
625                 630                 635                 640
Phe Gly Ile Leu Ile Lys Arg Arg Gln Gln Lys Ile Arg Lys Tyr Thr
                645                 650                 655
Met Arg Arg Leu Leu Gln Glu Thr Glu Leu Val Glu Pro Leu Thr Pro
                660                 665                 670
Ser Gly Ala Met Pro Asn Gln Ala Gln Met Arg Ile Leu Lys Glu Thr
            675                 680                 685
Glu Leu Arg Lys Val Lys Val Leu Gly Ser Gly Ala Phe Gly Thr Val
        690                 695                 700
Tyr Lys Gly Ile Trp Ile Pro Asp Gly Glu Asn Val Lys Ile Pro Val
705                 710                 715                 720
Ala Ile Lys Val Leu Arg Glu Asn Thr Ser Pro Lys Ala Asn Lys Glu
                725                 730                 735
Ile Leu Asp Glu Ala Tyr Val Met Ala Gly Val Gly Ser Pro Tyr Val
                740                 745                 750
Ser Arg Leu Leu Gly Ile Cys Leu Thr Ser Thr Val Gln Leu Val Thr
            755                 760                 765
Gln Leu Met Pro Tyr Gly Cys Leu Leu Asp His Val Arg Glu Asn Arg
        770                 775                 780
Gly Arg Leu Gly Ser Gln Asp Leu Leu Asn Trp Cys Met Gln Ile Ala
785                 790                 795                 800
Lys Gly Met Ser Tyr Leu Glu Asp Val Arg Leu Val His Arg Asp Leu
                805                 810                 815
Ala Ala Arg Asn Val Leu Val Lys Ser Pro Asn His Val Lys Ile Thr
                820                 825                 830
Asp Phe Gly Leu Ala Arg Leu Leu Asp Ile Asp Glu Thr Glu Tyr His
            835                 840                 845
Ala Asp Gly Gly Lys Val Pro Ile Lys Trp Met Ala Leu Glu Ser Ile
        850                 855                 860
Leu Arg Arg Arg Phe Thr His Gln Ser Asp Val Trp Ser Tyr Gly Val
865                 870                 875                 880
Thr Val Trp Glu Leu Met Thr Phe Gly Ala Lys Pro Tyr Asp Gly Ile
                885                 890                 895
Pro Ala Arg Glu Ile Pro Asp Leu Leu Glu Lys Gly Glu Arg Leu Pro
                900                 905                 910
Gln Pro Pro Ile Cys Thr Ile Asp Val Tyr Met Ile Met Val Lys Cys
            915                 920                 925
Trp Met Ile Asp Ser Glu Cys Arg Pro Arg Phe Arg Glu Leu Val Ser
        930                 935                 940
Glu Phe Ser Arg Met Ala Arg Asp Pro Gln Arg Phe Val Val Ile Gln
945                 950                 955                 960
Asn Glu Asp Leu Gly Pro Ala Ser Pro Leu Asp Ser Thr Phe Tyr Arg
                965                 970                 975
Ser Leu Leu Glu Asp Asp Asp Met Gly Asp Leu Val Asp Ala Glu Glu
            980                 985                 990
Tyr Leu Val Pro Gln Gln Gly Phe  Phe Cys Pro Asp Pro  Ala Pro Gly
        995                 1000                1005
```

```
Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065

Gln Ser Leu Pro Thr His Asp Pro Ser Pro Leu Gln Arg Tyr Ser
    1070                1075                1080

Glu Asp Pro Thr Val Pro Leu Pro Ser Glu Thr Asp Gly Tyr Val
    1085                1090                1095

Ala Pro Leu Thr Cys Ser Pro Gln Pro Glu Tyr Val Asn Gln Pro
    1100                1105                1110

Asp Val Arg Pro Gln Pro Pro Ser Pro Arg Glu Gly Pro Leu Pro
    1115                1120                1125

Ala Ala Arg Pro Ala Gly Ala Thr Leu Glu Arg Pro Lys Thr Leu
    1130                1135                1140

Ser Pro Gly Lys Asn Gly Val Val Lys Asp Val Phe Ala Phe Gly
    1145                1150                1155

Gly Ala Val Glu Asn Pro Glu Tyr Leu Thr Pro Gln Gly Gly Ala
    1160                1165                1170

Ala Pro Gln Pro His Pro Pro Pro Ala Phe Ser Pro Ala Phe Asp
    1175                1180                1185

Asn Leu Tyr Tyr Trp Asp Gln Asp Pro Pro Glu Arg Gly Ala Pro
    1190                1195                1200

Pro Ser Thr Phe Lys Gly Pro Thr Ala Glu Asn Pro Glu Tyr
    1205                1210                1215

Leu Gly Leu Asp Val Pro Val
    1220                1225

<210> SEQ ID NO 21
<211> LENGTH: 888
<212> TYPE: PRT
<213> ORGANISM: Homo sapiens

<400> SEQUENCE: 21

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140
```

```
Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
            165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560
```

-continued

```
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Pro Leu Thr Ser Ile Ile Ser
625                 630                 635                 640
Ala Val Val Gly Ile Leu Leu Val Val Leu Gly Val Val Phe Gly
                645                 650                 655
Ile Leu Ile Lys Arg Arg Gln Gln Lys Ile Arg Lys Tyr Thr Met Arg
                660                 665                 670
Arg Leu Leu Gln Glu Thr Glu Leu Val Glu Pro Leu Thr Pro Ser Gly
            675                 680                 685
Ala Met Pro Asn Gln Ala Gln Met Arg Ile Leu Lys Glu Thr Glu Leu
        690                 695                 700
Arg Lys Val Lys Val Leu Gly Ser Gly Ala Phe Gly Thr Val Tyr Lys
705                 710                 715                 720
Gly Ile Trp Ile Pro Asp Gly Glu Asn Val Lys Ile Pro Val Ala Ile
                725                 730                 735
Lys Val Leu Arg Glu Asn Thr Ser Pro Lys Ala Asn Lys Glu Ile Leu
                740                 745                 750
Asp Glu Thr Ile Ser Asn Leu Phe Ser Asn Phe Ala Pro Arg Gly Pro
            755                 760                 765
Ser Ala Cys Cys Glu Pro Thr Cys Trp Cys His Ser Gly Lys Gly Gln
        770                 775                 780
Asp Ser Leu Pro Arg Glu Glu Trp Gly Arg Gln Arg Arg Phe Cys Leu
785                 790                 795                 800
Trp Gly Cys Arg Gly Glu Pro Arg Val Leu Asp Thr Pro Gly Arg Ser
                805                 810                 815
Cys Pro Ser Ala Pro Pro Ser Ser Cys Leu Gln Pro Ser Leu Arg Gln
                820                 825                 830
Pro Leu Leu Leu Gly Pro Gly Pro Thr Arg Ala Gly Gly Ser Thr Gln
            835                 840                 845
His Leu Gln Arg Asp Thr Tyr Gly Arg Glu Pro Arg Val Pro Gly Ser
        850                 855                 860
Gly Arg Ala Ser Val Asn Gln Lys Ala Lys Ser Ala Glu Ala Leu Met
865                 870                 875                 880
Cys Pro Gln Gly Ala Gly Lys Ala
                885

<210> SEQ ID NO 22
<211> LENGTH: 943
<212> TYPE: PRT
<213> ORGANISM: Homo sapiens

<400> SEQUENCE: 22

Met Arg Pro Ser Gly Thr Ala Gly Ala Ala Phe Leu Ala Leu Leu Ala
1               5                   10                  15
Ala Leu Cys Pro Ala Ser Arg Ala Leu Glu Glu Lys Lys Gly Asn Tyr
            20                  25                  30
Val Val Thr Asp His Gly Ser Cys Val Arg Ala Cys Gly Ala Asp Ser
        35                  40                  45
```

```
Tyr Glu Met Glu Glu Asp Gly Val Arg Lys Cys Lys Cys Glu Gly
         50                  55                  60
Pro Cys Arg Lys Val Cys Asn Gly Ile Gly Ile Gly Glu Phe Lys Asp
 65                  70                  75                  80
Ser Leu Ser Ile Asn Ala Thr Asn Ile Lys His Phe Lys Asn Cys Thr
                     85                  90                  95
Ser Ile Ser Gly Asp Leu His Ile Leu Pro Val Ala Phe Arg Gly Asp
                100                 105                 110
Ser Phe Thr His Thr Pro Pro Leu Asp Pro Gln Glu Leu Asp Ile Leu
            115                 120                 125
Lys Thr Val Lys Glu Ile Thr Gly Phe Leu Leu Ile Gln Ala Trp Pro
130                 135                 140
Glu Asn Arg Thr Asp Leu His Ala Phe Glu Asn Leu Glu Ile Ile Arg
145                 150                 155                 160
Gly Arg Thr Lys Gln His Gly Gln Phe Ser Leu Ala Val Val Ser Leu
                165                 170                 175
Asn Ile Thr Ser Leu Gly Leu Arg Ser Leu Lys Glu Ile Ser Asp Gly
                180                 185                 190
Asp Val Ile Ile Ser Gly Asn Lys Asn Leu Cys Tyr Ala Asn Thr Ile
            195                 200                 205
Asn Trp Lys Lys Leu Phe Gly Thr Ser Gly Gln Lys Thr Lys Ile Ile
210                 215                 220
Ser Asn Arg Gly Glu Asn Ser Cys Lys Ala Thr Gly Gln Val Cys His
225                 230                 235                 240
Ala Leu Cys Ser Pro Glu Gly Cys Trp Gly Pro Glu Pro Arg Asp Cys
                245                 250                 255
Val Ser Cys Arg Asn Val Ser Arg Gly Arg Glu Cys Val Asp Lys Cys
                260                 265                 270
Asn Leu Leu Glu Gly Glu Pro Arg Glu Phe Val Glu Asn Ser Glu Cys
            275                 280                 285
Ile Gln Cys His Pro Glu Cys Leu Pro Gln Ala Met Asn Ile Thr Cys
            290                 295                 300
Thr Gly Arg Gly Pro Asp Asn Tyr Ile Gln Cys Ala His Tyr Ile Asp
305                 310                 315                 320
Gly Pro His Cys Val Lys Thr Cys Pro Ala Gly Val Met Gly Glu Asn
                325                 330                 335
Asn Thr Leu Val Trp Lys Tyr Ala Asp Ala Gly His Val Cys His Leu
                340                 345                 350
Cys His Pro Asn Cys Thr Tyr Gly Cys Thr Gly Pro Gly Leu Glu Gly
            355                 360                 365
Cys Pro Thr Asn Gly Pro Lys Ile Pro Ser Ile Ala Thr Gly Met Val
370                 375                 380
Gly Ala Leu Leu Leu Leu Leu Val Val Ala Leu Gly Ile Gly Leu Phe
385                 390                 395                 400
Met Arg Arg Arg His Ile Val Arg Lys Arg Thr Leu Arg Arg Leu Leu
                405                 410                 415
Gln Glu Arg Glu Leu Val Glu Pro Leu Thr Pro Ser Gly Glu Ala Pro
                420                 425                 430
Asn Gln Ala Leu Leu Arg Ile Leu Lys Glu Thr Glu Phe Lys Lys Ile
            435                 440                 445
Lys Val Leu Gly Ser Gly Ala Phe Gly Thr Val Tyr Lys Gly Leu Trp
450                 455                 460
```

```
Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
            485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
            515                 520                 525

Gly Cys Leu Leu Asp Tyr Val Arg Glu His Lys Asp Asn Ile Gly Ser
            530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
                580                 585                 590

Lys Leu Leu Gly Ala Glu Glu Lys Glu Tyr His Ala Glu Gly Gly Lys
            595                 600                 605

Val Pro Ile Lys Trp Met Ala Leu Glu Ser Ile Leu His Arg Ile Tyr
            610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
            675                 680                 685

Asp Ser Arg Pro Lys Phe Arg Glu Leu Ile Ile Glu Phe Ser Lys Met
            690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
            755                 760                 765

Ser Ser Leu Ser Ala Thr Ser Asn Asn Ser Thr Val Ala Cys Ile Asp
770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
            835                 840                 845

Asn Pro Ala Pro Ser Arg Asp Pro His Tyr Gln Asp Pro His Ser Thr
            850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
```

```
                885                 890                 895
Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
            915                 920                 925

Glu Tyr Leu Arg Val Ala Pro Gln Ser Ser Glu Phe Ile Gly Ala
            930                 935                 940

<210> SEQ ID NO 23
<211> LENGTH: 238
<212> TYPE: PRT
<213> ORGANISM: Artificial sequence
<220> FEATURE:
<223> OTHER INFORMATION: synthetic polypeptide sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Ser Thr Ser Gly
            100                 105                 110

Ser Gly Lys Pro Gly Ser Gly Glu Gly Ser Glu Val Gln Val Leu Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Ser Thr Asn Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Gly Ser Ser Gly Trp
    210                 215                 220

Ser Glu Tyr Trp Gly Gln Gly Thr Leu Val Thr Val Ser Ser
225                 230                 235

<210> SEQ ID NO 24
<211> LENGTH: 21
<212> TYPE: PRT
<213> ORGANISM: Artificial sequence
<220> FEATURE:
<223> OTHER INFORMATION: synthetic polypeptide sequence

<400> SEQUENCE: 24

Met Ala Leu Pro Val Thr Ala Leu Leu Leu Pro Leu Ala Leu Leu Leu
1               5                   10                  15
```

His Ala Ala Arg Pro
            20

<210> SEQ ID NO 25
<211> LENGTH: 10
<212> TYPE: PRT
<213> ORGANISM: Artificial sequence
<220> FEATURE:
<223> OTHER INFORMATION: synthetic polypeptide sequence

<400> SEQUENCE: 25

Glu Gln Lys Leu Ile Ser Glu Glu Asp Leu
1               5                   10

<210> SEQ ID NO 26
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 26

Asp Tyr Lys Asp Asp Asp Asp Lys
1               5

<210> SEQ ID NO 27
<211> LENGTH: 20
<212> TYPE: DNA
<213> ORGANISM: Artificial sequence
<220> FEATURE:
<223> OTHER INFORMATION: synthetic polynucleotide sequence

<400> SEQUENCE: 27
ggagcactgt cctccgaacg                                                   20

<210> SEQ ID NO 28
<211> LENGTH: 775
<212> TYPE: PRT
<213> ORGANISM: Artificial Sequence
<220> FEATURE:
<223> OTHER INFORMATION: synthetic polypeptide sequence

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Ser Thr Ser Gly
            100                 105                 110

Ser Gly Lys Pro Gly Ser Gly Glu Gly Ser Glu Val Gln Val Leu Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Ser Tyr Ala Met Ser Trp Val Arg

```
            145                 150                 155                 160
        Gln Ala Pro Gly Lys Gly Leu Glu Trp Val Ser Ala Ile Ser Gly Ser
                        165                 170                 175
        Gly Gly Ser Thr Asn Tyr Ala Asp Ser Val Lys Gly Arg Phe Thr Ile
                        180                 185                 190
        Ser Arg Asp Asn Ser Lys Asn Thr Leu Tyr Leu Gln Met Asn Ser Leu
                        195                 200                 205
        Arg Ala Glu Asp Thr Ala Val Tyr Tyr Cys Ala Gly Ser Ser Gly Trp
                        210                 215                 220
        Ser Glu Tyr Trp Gly Gln Gly Thr Leu Val Thr Val Ser Ser Ile Leu
        225                 230                 235                 240
        Asp Tyr Ser Phe Thr Gly Gly Ala Gly Arg Asp Ile Pro Pro Pro Gln
                        245                 250                 255
        Ile Glu Glu Ala Cys Glu Leu Pro Glu Cys Gln Val Asp Ala Gly Asn
                        260                 265                 270
        Lys Val Cys Asn Leu Gln Cys Asn Asn His Ala Cys Gly Trp Asp Gly
                        275                 280                 285
        Gly Asp Cys Ser Leu Asn Phe Asn Asp Pro Trp Lys Asn Cys Thr Gln
                        290                 295                 300
        Ser Leu Gln Cys Trp Lys Tyr Phe Ser Asp Gly His Cys Asp Ser Gln
        305                 310                 315                 320
        Cys Asn Ser Ala Gly Cys Leu Phe Asp Gly Phe Asp Cys Gln Leu Thr
                        325                 330                 335
        Glu Gly Gln Cys Asn Pro Leu Tyr Asp Gln Tyr Cys Lys Asp His Phe
                        340                 345                 350
        Ser Asp Gly His Cys Asp Gln Gly Cys Asn Ser Ala Glu Cys Glu Trp
                        355                 360                 365
        Asp Gly Leu Asp Cys Ala Glu His Val Pro Glu Arg Leu Ala Ala Gly
                        370                 375                 380
        Thr Leu Val Leu Val Val Leu Pro Pro Asp Gln Leu Arg Asn Asn
        385                 390                 395                 400
        Ser Phe His Phe Leu Arg Glu Leu Ser His Val Leu His Thr Asn Val
                        405                 410                 415
        Val Phe Lys Arg Asp Ala Gln Gly Gln Gln Met Ile Phe Pro Tyr Tyr
                        420                 425                 430
        Gly His Glu Glu Leu Arg Lys His Pro Ile Lys Arg Ser Thr Val
                        435                 440                 445
        Gly Trp Ala Thr Ser Ser Leu Leu Pro Gly Thr Ser Gly Gly Arg Gln
        450                 455                 460
        Arg Arg Glu Leu Asp Pro Met Asp Ile Arg Gly Ser Ile Val Tyr Leu
        465                 470                 475                 480
        Glu Ile Asp Asn Arg Gln Cys Val Gln Ser Ser Gln Cys Phe Gln
                        485                 490                 495
        Ser Ala Thr Asp Val Ala Ala Phe Leu Gly Ala Leu Ala Ser Leu Gly
                        500                 505                 510
        Ser Leu Asn Ile Pro Tyr Lys Ile Glu Ala Val Lys Ser Glu Pro Val
                        515                 520                 525
        Glu Pro Pro Leu Pro Ser Gln Leu His Leu Met Tyr Val Ala Ala Ala
                        530                 535                 540
        Ala Phe Val Leu Leu Phe Phe Val Gly Cys Gly Val Leu Leu Ser Arg
        545                 550                 555                 560
        Lys Arg Arg Arg Met Lys Leu Leu Ser Ser Ile Glu Gln Ala Cys Asp
                        565                 570                 575
```

-continued

```
Ile Cys Arg Leu Lys Lys Leu Lys Cys Ser Lys Glu Lys Pro Lys Cys
            580                 585                 590

Ala Lys Cys Leu Lys Asn Asn Trp Glu Cys Arg Tyr Ser Pro Lys Thr
            595                 600                 605

Lys Arg Ser Pro Leu Thr Arg Ala His Leu Thr Glu Val Glu Ser Arg
610                 615                 620

Leu Glu Arg Leu Glu Gln Leu Phe Leu Leu Ile Phe Pro Arg Glu Asp
625                 630                 635                 640

Leu Asp Met Ile Leu Lys Met Asp Ser Leu Gln Asp Ile Lys Ala Leu
                645                 650                 655

Leu Thr Gly Leu Phe Val Gln Asp Asn Val Asn Lys Asp Ala Val Thr
                660                 665                 670

Asp Arg Leu Ala Ser Val Glu Thr Asp Met Pro Leu Thr Leu Arg Gln
                675                 680                 685

His Arg Ile Ser Ala Thr Ser Ser Glu Glu Ser Ser Asn Lys Gly
            690                 695                 700

Gln Arg Gln Leu Thr Val Ser Ala Ala Gly Gly Ser Gly Gly Ser
705                 710                 715                 720

Gly Gly Ser Asp Ala Leu Asp Asp Phe Asp Leu Asp Met Leu Gly Ser
                725                 730                 735

Asp Ala Leu Asp Asp Phe Asp Leu Asp Met Leu Gly Ser Asp Ala Leu
                740                 745                 750

Asp Asp Phe Asp Leu Asp Met Leu Gly Ser Asp Ala Leu Asp Asp Phe
                755                 760                 765

Asp Leu Asp Met Leu Gly Ser
                770                 775

<210> SEQ ID NO 29
<211> LENGTH: 492
<212> TYPE: PRT
<213> ORGANISM: Artificial sequence
<220> FEATURE:
<223> OTHER INFORMATION: synthetic polypeptide sequence

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser Tyr Pro
                85                  90                  95

Trp Thr Phe Gly Gln Gly Thr Lys Val Glu Ile Lys Arg Thr Gly Gly
                100                 105                 110

Gly Gly Ser Gly Ala Gly Ser Gly Gly Gly Thr Gly Gly
            115                 120                 125

Gly Ser Glu Val Asp Leu Leu Glu Ser Gly Gly Leu Val Gln Pro
        130                 135                 140

Gly Gly Ser Leu Arg Leu Ser Cys Ala Ala Ser Gly Phe Thr Phe Ser
145                 150                 155                 160
```

Arg Tyr Trp Met His Trp Val Arg Gln Ala Pro Gly Lys Gly Leu Glu
            165                 170                 175

Trp Val Ser Ser Ile Ser Pro Tyr Asp Gly Glu Thr Asn Tyr Ala Asp
            180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
            210                 215                 220

Tyr Cys Ala Arg Ile Ser Glu Trp Tyr Asn Trp Ala Val Asp Val Phe
225                 230                 235                 240

Asp Tyr Trp Gly Gln Gly Thr Leu Val Thr Val Ser Ser Thr Thr Thr
            245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
            275                 280                 285

His Thr Arg Gly Leu Asp Phe Ala Cys Asp Ile Tyr Ile Trp Ala Pro
            290                 295                 300

Leu Ala Gly Thr Cys Gly Val Leu Leu Leu Ser Leu Val Ile Thr Leu
305                 310                 315                 320

Tyr Cys Gly Ser Gly Ser Gly Ser Gly Ser Lys Arg Gly Arg Lys Lys
            325                 330                 335

Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Gly Ser Gly Ser Gly Ser Arg Val Lys Phe
            370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
            485                 490

<210> SEQ ID NO 30
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 30

Leu Thr Cys Leu Gly Gly Phe Ala Ser Pro Gly Pro Val Pro Pro Ser
1               5                   10                  15

Thr Ala Leu Arg Lys Leu Ile Glu Glu Leu Val Asn Ile Thr Gln Asn
            20                  25                  30

Gln Lys Ala Pro Leu Cys Asn Gly Ser Met Val Trp Ser Ile Asn Leu
                35                  40                  45

Thr Ala Gly Met Tyr Cys Ala Ala Leu Glu Ser Leu Ile Asn Val Ser
    50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu His Leu
                100                 105                 110

Arg Lys Leu Phe Arg Glu Gly Arg Phe Asn Thr Thr Pro Ala Pro
                115                 120                 125

Arg Pro Pro Thr Pro Ala Pro Thr Ile Ala Ser Gln Pro Leu Ser Leu
                130                 135                 140

Arg Pro Glu Ala Cys Arg Pro Ala Ala Gly Gly Ala Val His Thr Arg
145                 150                 155                 160

Gly Leu Asp Phe Ala Cys Asp Ile Tyr Ile Trp Ala Pro Leu Ala Gly
                165                 170                 175

Thr Cys Gly Val Leu Leu Leu Ser Leu Val Ile Thr Leu Tyr Cys Gly
                180                 185                 190

Ser Gly Ser Gly Ser Gly Ser Gly Ser Lys Arg Gly Arg Lys Lys Leu
                195                 200                 205

Leu Tyr Ile Phe Lys Gln Pro Phe Met Arg Pro Val Gln Thr Thr Gln
                210                 215                 220

Glu Glu Asp Gly Cys Ser Cys Arg Phe Pro Glu Glu Glu Gly Gly
225                 230                 235                 240

Cys Glu Leu Gly Ser Gly Ser Gly Ser Arg Val Lys Phe Ser Arg Ser
                245                 250                 255

Ala Asp Ala Pro Ala Tyr Lys Gln Gly Gln Asn Gln Leu Tyr Asn Glu
                260                 265                 270

Leu Asn Leu Gly Arg Arg Glu Glu Tyr Asp Val Leu Asp Lys Arg Arg
                275                 280                 285

Gly Arg Asp Pro Glu Met Gly Gly Lys Pro Arg Arg Lys Asn Pro Gln
                290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
                340                 345                 350

Leu His Met Gln Ala Leu Pro Pro Arg
                355                 360

<210> SEQ ID NO 31
<211> LENGTH: 630
<212> TYPE: PRT
<213> ORGANISM: Artificial sequence
<220> FEATURE:
<223> OTHER INFORMATION: synthetic polypeptide sequence

<400> SEQUENCE: 31

Leu Thr Cys Leu Gly Gly Phe Ala Ser Pro Gly Pro Val Pro Pro Ser
1               5                   10                  15

Thr Ala Leu Arg Lys Leu Ile Glu Glu Leu Val Asn Ile Thr Gln Asn
                20                  25                  30

```
Gln Lys Ala Pro Leu Cys Asn Gly Ser Met Val Trp Ser Ile Asn Leu
         35                  40                  45
Thr Ala Gly Met Tyr Cys Ala Ala Leu Glu Ser Leu Ile Asn Val Ser
 50                  55                  60
Gly Cys Ser Ala Ile Glu Lys Thr Gln Arg Met Leu Ser Gly Phe Cys
 65                  70                  75                  80
Pro His Lys Val Ser Ala Gly Gln Phe Ser Ser Leu His Val Arg Asp
                 85                  90                  95
Thr Lys Ile Glu Val Ala Gln Phe Val Lys Asp Leu Leu His Leu
                100                 105                 110
Arg Lys Leu Phe Arg Glu Gly Arg Phe Asn Gly Gly Ser Gly Gly
             115                 120                 125
Gly Ser Gly Gly Gly Ser Gly Gly Ser Glu Ile Val Leu Thr Gln
     130                 135                 140
Ser Pro Gly Thr Leu Ser Leu Ser Pro Gly Glu Arg Ala Thr Leu Ser
145                 150                 155                 160
Cys Arg Ala Ser Gln Ser Val Ser Ser Ser Asn Leu Ala Trp Tyr Gln
                165                 170                 175
Gln Lys Pro Gly Gln Ala Pro Arg Leu Leu Ile Tyr Gly Ala Ser Ser
             180                 185                 190
Arg Ala Thr Gly Val Pro Asp Arg Phe Ser Gly Ser Gly Ser Gly Thr
             195                 200                 205
Asp Phe Thr Leu Thr Ile Ser Arg Leu Glu Pro Glu Asp Phe Ala Val
             210                 215                 220
Tyr Tyr Cys Gln Gln Ser Ser Tyr Pro Trp Thr Phe Gly Gln Gly
225                 230                 235                 240
Thr Lys Val Glu Ile Lys Arg Thr Gly Gly Gly Gly Ser Gly Ala Gly
                245                 250                 255
Gly Ser Gly Gly Gly Gly Thr Gly Gly Gly Gly Ser Glu Val Asp Leu
             260                 265                 270
Leu Glu Ser Gly Gly Gly Leu Val Gln Pro Gly Gly Ser Leu Arg Leu
         275                 280                 285
Ser Cys Ala Ala Ser Gly Phe Thr Phe Ser Arg Tyr Trp Met His Trp
         290                 295                 300
Val Arg Gln Ala Pro Gly Lys Gly Leu Glu Trp Val Ser Ser Ile Ser
305                 310                 315                 320
Pro Tyr Asp Gly Glu Thr Asn Tyr Ala Asp Ser Val Lys Gly Arg Phe
                325                 330                 335
Thr Ile Ser Arg Asp Asn Ser Lys Asn Thr Leu Tyr Leu Gln Met Asn
             340                 345                 350
Ser Leu Arg Ala Glu Asp Thr Ala Val Tyr Tyr Cys Ala Arg Ile Ser
         355                 360                 365
Glu Trp Tyr Asn Trp Ala Val Asp Val Phe Asp Tyr Trp Gly Gln Gly
     370                 375                 380
Thr Leu Val Thr Val Ser Ser Thr Thr Pro Ala Pro Arg Pro Pro
385                 390                 395                 400
Thr Pro Ala Pro Thr Ile Ala Ser Gln Pro Leu Ser Leu Arg Pro Glu
                405                 410                 415
Ala Cys Arg Pro Ala Ala Gly Gly Ala Val His Thr Arg Gly Leu Asp
             420                 425                 430
Phe Ala Cys Asp Ile Tyr Ile Trp Ala Pro Leu Ala Gly Thr Cys Gly
         435                 440                 445
```

```
Val Leu Leu Ser Leu Val Ile Thr Leu Tyr Cys Gly Ser Gly Ser
    450             455                 460

Gly Ser Gly Ser Gly Ser Lys Arg Gly Arg Lys Lys Leu Leu Tyr Ile
465             470                 475                 480

Phe Lys Gln Pro Phe Met Arg Pro Val Gln Thr Thr Gln Glu Asp
                485                 490                 495

Gly Cys Ser Cys Arg Phe Pro Glu Glu Glu Glu Gly Gly Cys Glu Leu
                500                 505                 510

Gly Ser Gly Ser Gly Ser Arg Val Lys Phe Ser Arg Ser Ala Asp Ala
            515                 520                 525

Pro Ala Tyr Lys Gln Gly Gln Asn Gln Leu Tyr Asn Glu Leu Asn Leu
530                 535                 540

Gly Arg Arg Glu Glu Tyr Asp Val Leu Asp Lys Arg Arg Gly Arg Asp
545                 550                 555                 560

Pro Glu Met Gly Gly Lys Pro Arg Arg Lys Asn Pro Gln Glu Gly Leu
                565                 570                 575

Tyr Asn Glu Leu Gln Lys Asp Lys Met Ala Glu Ala Tyr Ser Glu Ile
                580                 585                 590

Gly Met Lys Gly Glu Arg Arg Arg Gly Lys Gly His Asp Gly Leu Tyr
            595                 600                 605

Gln Gly Leu Ser Thr Ala Thr Lys Asp Thr Tyr Asp Ala Leu His Met
610                 615                 620

Gln Ala Leu Pro Pro Arg
625                 630

<210> SEQ ID NO 32
<211> LENGTH: 483
<212> TYPE: PRT
<213> ORGANISM: Artificial sequence
<220> FEATURE:
<223> OTHER INFORMATION: synthetic polypeptide sequence

<400> SEQUENCE: 32

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Gln Ala Leu Glu Trp Met
        35                  40                  45

Gly Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Phe Thr Tyr Trp Gly Arg Gly Thr Leu Val Thr
            100                 105                 110

Ser Ser Gly Gly Gly Gly Ser Gly Gly Gly Ser Gly Gly Gly Gly
        115                 120                 125

Ser Asp Ile Gln Leu Thr Gln Ser Pro Ser Ser Leu Ser Ala Ser Val
    130                 135                 140

Gly Asp Arg Val Thr Ile Thr Cys Lys Ala Ser Gln Asp Ile Asn Asn
145                 150                 155                 160

Tyr Leu Ser Trp Tyr Gln Gln Lys Pro Gly Gln Ala Pro Arg Leu Leu
                165                 170                 175
```

```
Ile Tyr Arg Ala Asn Arg Leu Val Asp Gly Val Pro Asp Arg Phe Ser
            180                 185                 190

Gly Ser Gly Tyr Gly Thr Asp Phe Thr Leu Thr Ile Asn Asn Ile Glu
        195                 200                 205

Ser Glu Asp Ala Ala Tyr Tyr Phe Cys Leu Lys Tyr Asp Val Phe Pro
    210                 215                 220

Tyr Thr Phe Gly Gln Gly Thr Lys Val Glu Ile Lys Ser Gly Gly Gly
225                 230                 235                 240

Gly Ser Asp Ile Lys Leu Gln Gln Ser Gly Ala Glu Leu Ala Arg Pro
                245                 250                 255

Gly Ala Ser Val Lys Met Ser Cys Lys Thr Ser Gly Tyr Thr Phe Thr
            260                 265                 270

Arg Tyr Thr Met His Trp Val Lys Gln Arg Pro Gly Gln Gly Leu Glu
        275                 280                 285

Trp Ile Gly Tyr Ile Asn Pro Ser Arg Gly Tyr Thr Asn Tyr Asn Gln
    290                 295                 300

Lys Phe Lys Asp Lys Ala Thr Leu Thr Thr Asp Lys Ser Ser Ser Thr
305                 310                 315                 320

Ala Tyr Met Gln Leu Ser Ser Leu Thr Ser Glu Asp Ser Ala Val Tyr
                325                 330                 335

Tyr Cys Ala Arg Tyr Tyr Asp Asp His Tyr Cys Leu Asp Tyr Trp Gly
            340                 345                 350

Gln Gly Thr Thr Leu Thr Val Ser Gly Gly Gly Gly Ser Gly Gly
        355                 360                 365

Gly Gly Ser Gly Gly Gly Ser Asp Ile Gln Leu Thr Gln Ser Pro
370                 375                 380

Ala Ile Met Ser Ala Ser Pro Gly Glu Lys Val Thr Met Thr Cys Arg
385                 390                 395                 400

Ala Ser Ser Ser Val Ser Tyr Met Asn Trp Tyr Gln Gln Lys Ser Gly
                405                 410                 415

Thr Ser Pro Lys Arg Trp Ile Tyr Asp Thr Ser Lys Val Ala Ser Gly
            420                 425                 430

Val Pro Tyr Arg Phe Ser Gly Ser Gly Ser Gly Thr Ser Tyr Ser Leu
        435                 440                 445

Thr Ile Ser Ser Met Glu Ala Glu Asp Ala Ala Thr Tyr Tyr Cys Gln
450                 455                 460

Gln Trp Ser Ser Asn Pro Leu Thr Phe Gly Ala Gly Thr Lys Leu Glu
465                 470                 475                 480

Leu Lys Ser

<210> SEQ ID NO 33
<211> LENGTH: 265
<212> TYPE: PRT
<213> ORGANISM: Artificial sequence
<220> FEATURE:
<223> OTHER INFORMATION: synthetic polypeptide sequence

<400> SEQUENCE: 33

Asn Tyr His Leu Glu Asn Glu Val Ala Arg Leu Lys Lys Leu Leu Val
1               5                   10                  15

Gly Glu Ala Ala Ala Lys Glu Ala Ala Lys Ala Gln Val Gln Leu
            20                  25                  30

Leu Glu Ser Gly Gly Gly Leu Val Gln Pro Gly Gly Ser Leu Arg Leu
        35                  40                  45

Ser Cys Ala Ala Ser Gly Phe Thr Phe Ser Ser Tyr Thr Met Ser Trp
```

```
                    50                  55                  60
Val Arg Gln Ala Pro Gly Gln Ala Leu Glu Trp Met Gly Thr Ile Ser
 65                  70                  75                  80

Ser Gly Gly Thr Tyr Thr Tyr Pro Asp Ser Val Lys Gly Arg Phe
                 85                  90                  95

Thr Ile Ser Arg Asp Asn Ala Lys Asn Ser Leu Tyr Leu Gln Met Asn
            100                 105                 110

Ser Leu Arg Ala Glu Asp Thr Ala Val Tyr Tyr Cys Ala Arg Glu Ala
            115                 120                 125

Ile Phe Thr Tyr Trp Gly Arg Gly Thr Leu Val Thr Ser Ser Gly Gly
            130                 135                 140

Gly Gly Ser Gly Gly Gly Ser Gly Gly Gly Ser Asp Ile Gln
145                 150                 155                 160

Leu Thr Gln Ser Pro Ser Ser Leu Ser Ala Ser Val Gly Asp Arg Val
                165                 170                 175

Thr Ile Thr Cys Lys Ala Ser Gln Asp Ile Asn Asn Tyr Leu Ser Trp
            180                 185                 190

Tyr Gln Gln Lys Pro Gly Gln Ala Pro Arg Leu Leu Ile Tyr Arg Ala
            195                 200                 205

Asn Arg Leu Val Asp Gly Val Pro Asp Arg Phe Ser Gly Ser Gly Tyr
210                 215                 220

Gly Thr Asp Phe Thr Leu Thr Ile Asn Asn Ile Glu Ser Glu Asp Ala
225                 230                 235                 240

Ala Tyr Tyr Phe Cys Leu Lys Tyr Asp Val Phe Pro Tyr Thr Phe Gly
            245                 250                 255

Gln Gly Thr Lys Val Glu Ile Lys Ser
            260                 265

<210> SEQ ID NO 34
<211> LENGTH: 433
<212> TYPE: PRT
<213> ORGANISM: Artificial sequence
<220> FEATURE:
<223> OTHER INFORMATION: synthetic polypeptide sequence

<400> SEQUENCE: 34

Asp Ala Val Val Thr Gln Glu Ser Ala Leu Thr Ser Ser Pro Gly Glu
 1               5                  10                  15

Thr Val Thr Leu Thr Cys Arg Ser Ser Thr Gly Ala Val Thr Thr Ser
                 20                  25                  30

Asn Tyr Ala Ser Trp Val Gln Glu Lys Pro Asp His Leu Phe Thr Gly
             35                  40                  45

Leu Ile Gly Gly Thr Asn Asn Arg Ala Pro Gly Val Pro Ala Arg Phe
         50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Val Leu Trp Tyr Ser Asp
                 85                  90                  95

His Trp Val Phe Gly Gly Gly Thr Lys Leu Thr Val Leu Gly Gly Gly
            100                 105                 110

Gly Gly Ser Gly Gly Gly Gly Ser Gly Gly Gly Gly Ser Gly Gly Gly
            115                 120                 125

Gly Ser Asp Val Gln Leu Gln Glu Ser Gly Pro Gly Leu Val Ala Pro
130                 135                 140

Ser Gln Ser Leu Ser Ile Thr Cys Thr Val Ser Gly Phe Leu Leu Thr
```

-continued

```
145                 150                 155                 160
Asp Tyr Gly Val Asn Trp Val Arg Gln Ser Pro Gly Lys Gly Leu Glu
                165                 170                 175

Trp Leu Gly Val Ile Trp Gly Asp Gly Ile Thr Asp Tyr Asn Ser Ala
                180                 185                 190

Leu Lys Ser Arg Leu Ser Val Thr Lys Asp Asn Ser Lys Ser Gln Val
                195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Glu Ser Lys Tyr Gly Pro Pro Cys Pro Pro Cys Pro Ile
                245                 250                 255

Tyr Ile Trp Ala Pro Leu Ala Gly Thr Cys Gly Val Leu Leu Leu Ser
                260                 265                 270

Leu Val Ile Thr Leu Tyr Cys Lys Arg Gly Arg Lys Lys Leu Leu Tyr
                275                 280                 285

Ile Phe Lys Gln Pro Phe Met Arg Pro Val Gln Thr Thr Gln Glu Glu
                290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Lys Gln
                325                 330                 335

Gly Gln Asn Gln Leu Tyr Asn Glu Leu Asn Leu Gly Arg Arg Glu Glu
                340                 345                 350

Tyr Asp Val Leu Asp Lys Arg Arg Gly Arg Asp Pro Glu Met Gly Gly
            355                 360                 365

Lys Pro Arg Arg Lys Asn Pro Gln Glu Gly Leu Tyr Asn Glu Leu Gln
            370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
                420                 425                 430

Arg
```

METHODS OF TREATING EGFRvIII EXPRESSING GLIOBLASTOMAS

CROSS-REFERENCE TO RELATED APPLICATIONS

This application is a § 371 national phase of International Application No. PCT/US2019/025846, filed on Apr. 4, 2019, which claims the benefit of U.S. Provisional Patent Application Ser. Nos. 62/654,012 filed Apr. 6, 2018 and 62/722,681 filed Aug. 24, 2018; the disclosures of which applications are herein incorporated by reference.

STATEMENT REGARDING FEDERALLY SPONSORED RESEARCH

This invention was made with government support under grant nos. RO1 CA196277, P50 GM081879 and R35 NS105068 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCSF-564WO_SeqList_ST25.txt" created on Mar. 29, 2019 and having a size of 156 KB. The contents of the text file are incorporated by reference herein in their entirety.

INTRODUCTION

Among neuroepithelial tumors, the most frequent (50-60%) is glioblastoma. Glioblastoma multiforme (GBM) is highly anaplastic and develops from a diffuse astrocytoma or de novo. GBM is often found in the cerebral hemispheres and its peak incidence occurs at an age of 45-70 years. The median survival of patients with GBM is typically less than 2 years. GBM tumors commonly appear as a heterogeneous mixture containing cells of various phenotypes and polymorphisms. Heterogeneity in GBM tumors at the cellular level undoubtedly contributes to the aggressive pathology of the disease and may play a role in tumor recurrences following treatment (see e.g., Soeda et al., Scientific Reports (2015) 5:7979). Targeted therapies for GBM have been deployed, including chimeric antigen receptor (CAR) T cell therapies directed to the neo-antigen epidermal growth factor receptor variant III (EGFRvIII) (see e.g., Johnson et al., Sci Transl Med. (2015) 7(275):275ra22). However, in some instances, these therapies have resulted in antigen loss and resistance to treatment (see e.g., O'Rourke et al., Sci Transl Med. (2017) 9(399)).

SUMMARY

Methods are provided for treating a subject for an EGFRvIII expressing glioblastoma. The methods of the present disclosure involve administering to the subject a molecular circuit that is primed by EGFRvIII to induce one or more encoded therapeutics specific for one or more antigens expressed by the glioblastoma. Nucleic acids containing sequences encoding all or portions of such circuits are also provided, as well as cells, expression cassettes and vectors that contain such nucleic acids. Also provided are kits for practicing the described methods.

BRIEF DESCRIPTION OF THE DRAWINGS

FIG. 4 demonstrates that the 'prime and kill' circuit was effective at driving the full eradication of heterogeneous populations of tumor cells having differing amounts of priming antigen-expressing tumor cells.

FIG. 5 depicts delayed killing kinetics in heterogeneous cell populations with lower ratios of priming antigen.

FIG. 16 depicts cells that contain IF/THEN circuits with and without OR gate functionality at the relevant binding triggered transcriptional switch, the antigen-specific therapeutic, or both.

DEFINITIONS

Figure 1A:
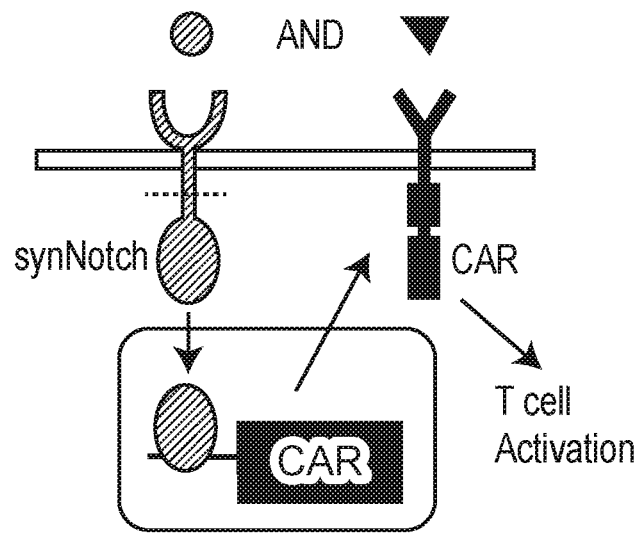
FIG. 1A-1D depict examples of prime/kill circuits, with or without diffusible components and employing antigen recognition of EGFRvIII priming antigen expressed on cancerous cells.

As used herein, the term "heterogeneous", when used in reference to cancer, generally refers to a cancer displaying some level of intracancer or intratumor heterogeneity, e.g., at the molecular, cellular, tissue or organ level. A heterogeneous cancer is composed of at least two different cell types, where different cell types may be defined in variety of ways. For example, different cell types may differ genomically (e.g., through the presence of a mutation in one cell type that is absent in another), transcriptionally (e.g., through expression of a gene in one cell type that is not expressed in another, through enhanced or reduced expression of a gene in one cell type as compared to another, etc.), or proteomically (e.g., through expression of a protein in one cell type that is not expressed in another, through enhanced or reduced expression of a protein in one cell type as compared to another, etc.). In some instances, cancer heterogeneity may be identified based on the presence of two or more phenotypically different cells present in a cancer, including e.g., where such phenotypically different cells are identified through clinical testing (e.g., histology, immunohistochemistry, in situ hybridization, cytometry, transcriptomics, mutational analysis, whole genome sequencing, proteomics, etc.).

As such, a heterogeneous cancer, as defined herein, will generally include at least one cancerous cell type and at least one other cell type, where the one other cell type may be a second cancerous cell type or a non-cancerous cell type. For example, a heterogeneous cancer may include a first cancerous cell type and a second cancerous cell type. Alternatively, a heterogeneous cancer may include a cancerous cell type and a non-cancerous cell type. Although a heterogeneous cancer will include at least two different cell types, such cancers are not so limited and may include e.g., more than two different cell types, three or more different cell types, four or more different cell types, five or more different cell types, etc., where at least one cell type is cancerous and the additional cell types may each be cancerous or non-cancerous.

As summarized above, heterogeneity of a cancer may be defined by differing gene or protein expression by different subpopulations of cells of the cancer. For example, in some instances, a first subpopulation of cells may express a first gene product from a first gene that is not expressed by a second subpopulation of cells, where such a second cell population may or may not express a second gene product from a second gene that defines the second population. Put another way, subpopulations of cells within a heterogeneous cancer may, in some instances, each be defined by the presence or absence (or relative levels) of one or more expressed gene products, where useful expressed gene products for defining cell types may include but are not limited to biomarkers, antigens, wild-type proteins, mutated proteins, wild-type transcripts, mutated transcripts, etc.

Cancer heterogeneity, in some instances, may include or exclude heterogeneity at the subject level, i.e., intrapatient heterogeneity. As used herein, the term "intrapatient heterogeneity" generally refers to heterogeneity observed between multiple cancers, e.g., multiple tumors, present in a single subject. For example, a primary tumor and a metastasis with a subject may be heterogeneous, e.g., differentially expressing a particular gene product, such as a biomarker, an antigen or a mutated protein. Multiple heterogeneous cancers may arise in a subject through various mechanisms including but not limited to mutation, clonal expansion, metastasis, selection, and combinations thereof. For example, two different intrapatient heterogeneous cancers arising by metastasis of a primary tumor may be heterogeneous with respect to the tissues in which they reside. Alternatively, two different intrapatient heterogeneous cancers derived from the same primary tumor may arise due to mutation and clonal expansion, where one cancer is a subclone of the other. Various other mechanism by which different intrapatient heterogeneous cancers may arise are possible and fall within the scope of the term as used herein.

Cancer heterogeneity, in some instances as used herein, may exclude heterogeneity at the population level, i.e., interpatient heterogeneity. As used herein, the term "interpatient heterogeneity" generally refers to differences observed between two cancers or two tumors present in separate subjects or patients.

As used herein, the terms "treatment," "treating," "treat" and the like, refer to obtaining a desired pharmacologic and/or physiologic effect and/or a response related to the treatment. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of an agent (including biologic agents, such as cells), or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "individual," "subject," "host," and "patient," used interchangeably herein, refer to a mammal, including, but not limited to, murines (e.g., rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also called resistant cancer.

The term "histology" and "histological" as used herein generally refers to microscopic analysis of the cellular anatomy and/or morphology of cells obtained from a multicellular organism including but not limited to plants and animals.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids or cells obtained from a tissue that have been dissociated into a liquid cellular sample.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional heterodimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel, Switzerland).

The terms "T cell receptor" and "TCR" are used interchangeably and will generally refer to a molecule found on the surface of T cells, or T lymphocytes, that is responsible for recognizing fragments of antigen as peptides bound to major histocompatibility complex (MHC) molecules. The TCR complex is a disulfide-linked membrane-anchored heterodimeric protein normally consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. In some instance, a TCR is generally referred to by reference to only the TCRα and TCRβ chains, however, as the assembled TCR complex may associate with endogenous delta, gamma, epsilon and/or zeta chains an ordinary skilled artisan will readily understand that reference to a TCR as present in a cell membrane may include reference to the fully or partially assembled TCR complex as appropriate.

Recombinant or engineered individual TCR chains and TCR complexes have been developed. References to the use of a TCR in a therapeutic context may refer to individual recombinant TCR chains. As such, engineered TCRs may include individual modified TCRα or modified TCRβ chains as well as single chain TCRs that include modified and/or unmodified TCRα and TCRβ chains that are joined into a single polypeptide by way of a linking polypeptide.

As used herein, by "chimeric bispecific binding member" is meant a chimeric polypeptide having dual specificity to two different binding partners (e.g., two different antigens). Non-limiting examples of chimeric bispecific binding members include bispecific antibodies, bispecific conjugated monoclonal antibodies (mab)$_2$, bispecific antibody fragments (e.g., F(ab)$_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. *MAbs*. (2012) 4(2): 182-197; Stamova et al. *Antibodies* 2012, 1(2), 172-198; Farhadfar et al. *Leuk Res*. (2016) 49:13-21; Benjamin et al. *Ther Adv Hematol*. (2016) 7(3):142-56; Kiefer et al. *Immunol Rev*. (2016) 270(1):178-92; Fan et al. *J Hematol Oncol*. (2015) 8:130; May et al. *Am J Health Syst Pharm*. (2016) 73(1):e6-e13; the disclosures of which are incorporated herein by reference in their entirety.

A "biological sample" encompasses a variety of sample types obtained from an individual or a population of individuals and can be used in various ways, including e.g., the isolation of cells or biological molecules, diagnostic assays, etc. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples (e.g., biopsy samples), and cellular samples. Accordingly, biological samples may be cellular samples or acellular samples.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, nanobodies, single-domain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al. (1993) *Nature* 363:446; Desmyter et al. (2015) *Curr. Opin. Struct. Biol.* 32:1). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama,*

*Llama guanicoe* and *Llama vicugna*). A single variable domain heavy chain antibody is referred to herein as a nanobody or a $V_{HH}$ antibody.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

A "orthogonal" or "orthogonalized" member or members of a binding pair are modified from their original or wild-type forms such that the orthogonal pair specifically bind one another but do not specifically or substantially bind the non-modified or wild-type components of the pair. Any binding partner/specific binding pair may be orthogonalized, including but not limited to e.g., those binding partner/specific binding pairs described herein.

The terms "domain" and "motif", used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

The terms "synthetic", "chimeric" and "engineered" as used herein generally refer to artificially derived polypeptides or polypeptide encoding nucleic acids that are not naturally occurring. Synthetic polypeptides and/or nucleic acids may be assembled de novo from basic subunits including, e.g., single amino acids, single nucleotides, etc., or may be derived from pre-existing polypeptides or polynucleotides, whether naturally or artificially derived, e.g., as through recombinant methods. Chimeric and engineered polypeptides or polypeptide encoding nucleic acids will generally be constructed by the combination, joining or fusing of two or more different polypeptides or polypeptide encoding nucleic acids or polypeptide domains or polypeptide domain encoding nucleic acids. Chimeric and engineered polypeptides or polypeptide encoding nucleic acids include where two or more polypeptide or nucleic acid "parts" that are joined are derived from different proteins (or nucleic acids that encode different proteins) as well as where the joined parts include different regions of the same protein (or nucleic acid encoding a protein) but the parts are joined in a way that does not occur naturally.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "operably linked" refers to a juxtaposition wherein the components so described are in a relationship permitting them to function in their intended manner. For instance, a promoter is operably linked to a coding sequence if the promoter affects its transcription or expression. Operably linked nucleic acid sequences may but need not necessarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "vector" or "expression vector" is a replicon, such as plasmid, phage, virus, or cosmid, to which another DNA segment, i.e. an "insert", may be attached so as to bring about the replication of the attached segment in a cell.

The term "Heterologous", as used herein, means a nucleotide or polypeptide sequence that is not found in the native (e.g., naturally-occurring) nucleic acid or protein, respectively. Heterologous nucleic acids or polypeptide may be derived from a different species as the organism or cell within which the nucleic acid or polypeptide is present or is expressed. Accordingly, a heterologous nucleic acids or polypeptide is generally of unlike evolutionary origin as compared to the cell or organism in which it resides.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides methods of treating a subject for an EGFRvIII expressing glioblastoma. The methods of the present disclosure involve administering to the subject a molecular circuit that is primed by EGFRvIII to induce one or more encoded therapeutics specific for one or more antigens expressed by the glioblastoma. The circuit may be administered in the form of cells encoding the molecular circuit, vector(s) that deliver nucleic acids encoding the circuit to cells of the subject, or the like. Accordingly, nucleic acids containing sequences encoding all or portions of such circuits are also provided, as well as cells, expression cassettes and vectors that contain such nucleic acids. Also provided are kits for practicing the described methods.

The subject circuits may integrate the expression of EGFRvIII on a glioblastoma multiforme (GBM) cell and at least a second antigen expressed on a second cell of the GBM to produce a desired outcome with respect to the second cell. The integration of two antigens expressed by different cells of a heterogeneous cell population to result in a desired targeting event may be referred to herein as "trans-targeting".

For example, an employed circuit may integrate EGFRvIII as a "priming antigen" expressed by a first GBM cell, referred to as a "priming cell", and a second antigen (e.g., a "targeting antigen" or "targeted antigen" or "killing antigen") expressed by a second cell, e.g., a nearby cell, of the GBM, referred to as a "targeted cell", to target the second cell type in trans. A therapeutic cell modified with such a circuit is primed by the presence of the EGFRvIII antigen on the first cell to then target the targeted cell.

For comparison, in this context cis-targeting refers to integrating of two antigens to target a single cell which expresses both a priming antigen and a targeting antigen to produce a desired outcome with respect to the single cell. Thus, in cis-targeting, the targeted cell expresses both the priming antigen and the targeting antigen such that the two antigens are expressed in cis with respect to the cell. In trans-targeting, the targeted cell expresses only the targeting antigen and not the priming antigen such that the two antigens are expressed in trans with respect to the two cells. As such, trans targeting may be employed to target a cell that does not express a priming antigen, e.g., does not express EGFRvIII. In some instances, a circuit of the present disclosure may employ both trans-targeting and cis-targeting, i.e., cis- and trans-targeting may be combined in a single circuit. In some instances, a circuit of the present disclosure may employ only trans-targeting and may e.g., exclude cis-targeting.

The circuits of the present disclosure will generally employ at least one binding triggered transcriptional switch (BTTS) as described in more detail below. A therapeutic cell may be modified to express a BTTS responsive to an EGFRvIII priming antigen. The BTTS may be expressed in the plasma membrane of the cell. Binding of the BTTS to EGFRvIII may induce expression of a protein in the BTTS expressing cell. The induced protein may be a heterologous antigen-specific protein, such as a second BTTS or a heterologous antigen-specific therapeutic, as described in more detail below. In the context of cis-targeting, binding of the BTTS to EGFRvIII expressed on a GBM priming cell induces expression of an antigen specific protein that is specific for a targeting antigen that is also expressed by the GBM priming cell (i.e., the GBM cell is both the priming cell and the targeted cell). In the context of trans-targeting, binding of the BTTS to EGFRvIII expressed on a GBM priming cell induces expression of an antigen specific protein that is specific for a targeting antigen that is expressed on a GBM cell that does not express the priming antigen (i.e., a GBM cell other than the priming cell).

In this manner, trans-targeting allows for targeting of cells by an antigen specific protein, such as an antigen-specific therapeutic, only in the presence of EGFRvIII-positive ("EGFRvIII(+)") priming cells. Correspondingly, trans-targeting allows for targeting of cells with an antigen specific protein, such as an antigen-specific therapeutic, in a heterogeneous cell population, such as a heterogeneous cancer, where the targeted cells do not express EGFRvIII, i.e., are EGFRvIII-negative ("EGFRvIII(−)") cells. Accordingly, such targeted EGFRvIII(−) GBM cells may be spatially associated with cells that do express EGFRvIII.

Methods

As summarized above, the present disclosure provides methods of targeting EGFRvIII(−) cells in a heterogeneous EGFRvIII(+) GBM, including where such cells are targeted in trans. Such methods may include administering, to a subject in need thereof, a circuit encoding a BTTS responsive to EGFRvIII(+) that induces expression of an antigen-specific therapeutic, where the antigen-specific therapeutic may be responsive to one or more antigens other than EGFRvIII. Such circuits, when expressed on a therapeutic immune cell, may activate the immune cell to mediate the targeted killing of EGFRvIII(−) GBM cells in a EGFR(+) GBM tumor.

Methods of Treatment

As summarized above, the methods of the present disclosure find use in treating a subject for a GBM, including where a subject's GBM is heterogeneous for EGFRvIII. Such treatments may include obtaining a desired effect with respect to at least one EGFRvIII(−) cell type (or subpopulation thereof) of a heterogeneously positive EGFRvIII tumor. By the terms "heterogeneously positive EGFRvIII", "EGFRvIII(+) GBM" or "EGFRvIII(+) tumor", as used herein, is generally meant a GBM tumor containing at least some cells that express EGFRvIII. Such tumors may include cells that are EGFRvIII(−) or may evolve to contain cells that are EGFR(−) over the course of tumor progression.

In some instances, treatments may include obtaining a desired effect with respect to one cell type or more than one cell type (or subpopulation of cells) of the heterogeneous GBM, including two or more, three or more, four or more, five or more, etc., cell types or subpopulations of cells of the heterogeneous GBM. Desired effects of the treatments, as described in more detail below, will vary. For example, with respect to one or more targeted cell types, desired effects will vary and may include but are not limited to e.g., killing of the one or more targeted cell types, reducing the proliferation of the one or more targeted cell types, and the like.

The subject methods may include introducing into a subject in need thereof, cells that contain nucleic acid sequences encoding a circuit for trans-targeting of a cell of a heterogeneous GBM. The introduced cells may be immune cells, including e.g., myeloid cells or lymphoid cells.

In some instances, the instant methods may include contacting a cell with one or more nucleic acids encoding a circuit wherein such contacting is sufficient to introduce the nucleic acid(s) into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like. Nucleic acids may be introduced into cells maintained or cultured in vitro or ex vivo. Nucleic acids may also be introduced into a cell in a living subject in vivo, e.g., through the use of one or more vectors (e.g., viral vectors) that deliver the nucleic acids into the cell without the need to isolate, culture or maintain the cells outside of the subject.

Introduced nucleic acids may be maintained within the cell or transiently present. As such, in some instance, an introduced nucleic acid may be maintained within the cell, e.g., integrated into the genome. Any convenient method of nucleic acid integration may find use in the subject methods, including but not limited to e.g., viral-based integration, transposon-based integration, homologous recombination-based integration, and the like. In some instance, an introduced nucleic acid may be transiently present, e.g., extrachromosomally present within the cell. Transiently present nucleic acids may persist, e.g., as part of any convenient transiently transfected vector.

An introduced nucleic acid encoding a circuit may be introduced in such a manner as to be operably linked to a regulatory sequence, such as a promoter, that drives the expression of one or more components of the circuit. The source of such regulatory sequences may vary and may include e.g., where the regulatory sequence is introduced with the nucleic acid, e.g., as part of an expression construct or where the regulatory sequence is present in the cell prior to introducing the nucleic acid or introduced after the nucleic acid. As described in more detail herein, useful regulatory sequence can include e.g., endogenous promoters and heterologous promoters. For example, in some instances, a nucleic acid may be introduced as part of an expression construct containing a heterologous promoter operably linked to a nucleic acid sequence. In some instances, a nucleic acid may be introduced as part of an expression construct containing a copy of a promoter that is endogenous to the cell into which the nucleic acid is introduced. In some instances, a nucleic acid may be introduced without a regulatory sequence and, upon integration into the genome of the cell, the nucleic acid may be operably linked to an endogenous regulatory sequence already present in the cell. Depending on the confirmation and/or the regulatory sequence utilized, expression of each component of the circuit from the nucleic acid may be configured to be constitutive, inducible, tissue-specific, cell-type specific, etc., including combinations thereof.

Any convenient method of delivering the circuit encoding components may find use in the subject methods. In some instances, the subject circuit may be delivered by administering to the subject a cell expressing the circuit. In some instances, the subject circuit may be delivered by administering to the subject a nucleic acid comprising one or more nucleotide sequences encoding the circuit. Administering to a subject a nucleic acid encoding the circuit may include administering to the subject a cell containing the nucleic acid where the nucleic acid may or may not yet be expressed. In some instances, administering to a subject a nucleic acid encoding the circuit may include administering to the subject a vector designed to deliver the nucleic acid to a cell.

Accordingly, in the subject methods of treatment, nucleic acids encoding a circuit or components thereof may be administered in vitro, ex vivo or in vivo. In some instances, cells may be collected from a subject and transfected with nucleic acid and the transfected cells may be administered to the subject, with or without further manipulation including but not limited to e.g., in vitro expansion. In some instances, the nucleic acid, e.g., with or without a delivery vector, may be administered directly to the subject.

EGFRvIII(+) priming cells and targeted cells of a subject circuit will generally differ in at least the expression of EGFRvIII. In some instances, priming cells and targeted cells may differ in the expression of at least one surface expressed epitope, e.g., a surfaced expressed protein, an antigen presented in the context of MHC, etc., other than EGFRvIII. In some instances, two different targeted cells may differ in the expression of at least one surface expressed epitope, e.g., a surfaced expressed protein, an antigen presented in the context of MHC, etc.

Differential expression between two cells or two cell types of a GBM will vary. For example, in some instances, a cell expresses one surface epitope not expressed by the other. In some instances, a cell expresses one surface epitope more highly than the surface epitope is expressed by the other cell. Where cells differ in the level, e.g., as compared to the presence/absence, of expression of a surface epitope the difference in level may vary but will generally be substantially different, e.g., sufficiently different to allow for practical targeting of one cell versus the other. Differences in expression between cells may range from less than one order of magnitude of expression to ten orders of magnitude of expression or more, including but not limited to e.g., 1 order of magnitude, 2 orders of magnitude, 3 orders of magnitude, 4 orders of magnitude, 5 orders of magnitude, 6 orders of magnitude, 7 orders of magnitude, 8 orders of magnitude, 9 orders of magnitude, 10 orders of magnitude, etc. In some instances, two cell types differing in level of expression of a particular epitope may be said to be "high" and "low" for the epitope, respectively, where high versus low expression may be differentiated using conventional methods known to the relevant artisan.

In some instances, the presence or absence of a particular epitope will be defined by the limit of detection of the method employed to detect the epitope, including e.g., where such limit of detection may or may not be based on an appropriate reference standard or positive or negative control. For example, where the epitope is present below the limit of detection the cell may be said to be "negative" for the epitope. Correspondingly, where the epitope is present below the level detected in a reference standard or appropriate control the cell may be said to be negative for the epitope. Where the epitope is present above the limit of detection the cell may be said to be "positive" for the epitope. Correspondingly, where the epitope is present above the level detected in a reference standard or appropriate control the cell may be said to be positive for the epitope.

As summarized above, EGFRvIII(+) priming cells and targeted cells in a heterogeneous GBM will generally be in sufficient proximity to allow for recognition of a targeted cell expressing a targeting antigen, but not the priming antigen, by a primed immune cell. Relative proximity between an EGFRvIII(+) priming cell and a targeted cell sufficient for trans-targeting of the targeted cell will vary and, as described herein, may be modified as desired depending on how the subject circuit is designed (e.g., through the use of a more or less stable antigen-specific therapeutic, through the use of a diffusible payload, etc.). In some instances, the EGFRvIII(+) priming cell and the targeted cell may be adjacent. In some instances, the priming cell and the targeted cell may be non-adjacent. As such, the proximity, expressed in this context as the distance between, a priming cell and a targeted cell may range from about 1 cell diameter to 100 cell diameters or more, including but not limited to e.g., 1 to 100 cell diameters, 2 to 100 cell diameters, 5 to 100 cell diameters, 10 to 100 cell diameters, 1 to 50 cell diameters, 2 to 50 cell diameters, 5 to 50 cell diameters, 10 to 50 cell diameters, 1 to 25 cell diameters, 2 to 25 cell diameters, 5 to 25 cell diameters, 10 to 25 cell diameters, etc.

Heterogeneity of GBM tumors treated using the methods described herein will vary. For example, in some instances, the degree of heterogeneity in a heterogeneous GBM will vary. For example, with respect to each individual cell type present in a heterogeneous GBM, a subject cell type (e.g., an EGFRvIII priming cell, a first targeted cell type, a second targeted cell type, or another cell type) will represent less than 100% of the cells of the GBM including but not limited to e.g., less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous GBM.

In some instances, 75% or less of the cells of a heterogeneous GBM express EGFRvIII, including but not limited to e.g., 70% or less, 65% or less, 60% or less, 55% or less, 50% or less, 45% or less, 40% or less, 35% or less, 30% or less, 25% or less, or 20% or less. In some instances, methods of the present disclosure find use in treating a heterogeneous GBM in a subject where the percentage of cell of the GBM that express EGFRvIII ranges from 1% or more than 1% to 99% or less than 99%, including but not limited to e.g., from 1% to 99%, from 5% to 90%, from 10% to 85%, from 20% to 80%, from 25% to 75% and the like.

In some instances, a targeted cell (e.g., an EGFR(−) cell present in an EGFR(+) tumor) of a herein disclosed methods may represent less than 50% of the cells of the heterogeneous cancer or heterogeneous tumor, including but not limited to e.g., less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous cancer or a heterogeneous tumor.

In some instances, a particular cell type present in a heterogeneous EGFR(+) GBM (e.g., a EGFR(+) priming cell type, a targeted cell type or another cell type) may be a majority cell type of the heterogeneous cancer, including e.g., where the particular cell type represents 50% or greater, including e.g., 60% or greater, 70% or greater, 80% or greater, 90% or greater, 95% or greater, of the cells of the heterogeneous GBM. In some instances, a EGFR(+) priming cell of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM. In some instances, a EGFRvIII(−) targeted cell of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM.

The methods of the present disclosure may be employed to target and treat a variety of GBM tumors, including e.g., primary GBM, secondary GBM tumors, re-growing GBM tumors, recurrent GBM tumors, refractory GBM tumors and the like. For example, in some instances, the methods of the present disclosure may be employed as an initial treatment of a primary GBM identified in a subject. In some instances, the methods of the present disclosure may be employed as a non-primary (e.g., secondary or later) treatment, e.g., in a subject with a GBM that is refractory to at least one prior treatment, in a subject with a GBM that is re-growing following at least one prior treatment, in a subject with a mixed response to at least one prior treatment (e.g., a positive response in at least one tumor in the subject and a negative or neutral response in at least a second tumor in the subject, including e.g., a mixed response to a treatment for multiple GBM), and the like.

In some instances, the method of the present disclosure may be employed to target, treat or clear a subject for minimal residual disease (MRD) remaining after a prior GBM therapy. Targeting, treating and/or clearance of GBM MRD may be pursued using the instant methods whether or not the MRD is or has been determined to be refractory to the prior treatment. In some instances, a method of the present disclosure may be employed to target, treat and/or clear a subject of MRD following a determination that the MRD is refractory to a prior treatment or one or more available treatment options other than those employing the herein described circuits.

In some instances, the instant methods may be employed prophylactically for surveillance. For example, a subject in need thereof may be administered a treatment involving one or more of the herein described circuits when the subject does not have detectable disease but is at risk of developing a GBM or a recurrent GBM. In some instances, a prophylactic approach may be employed when a subject is at particularly high risk of developing a primary GBM that would be predicted to be a heterogeneous GBM. In some instances, a prophylactic approach may be employed when a subject has been previously treated for a GBM and is at risk of reoccurrence. Essentially any combination of EGFRvIII priming antigen and targeting antigen may be employed in prophylactic treatments, including those described herein.

In some instances, the herein described methods may be used to prophylactically surveil a subject for GBM cells expressing one or more mutations commonly present in GBM tumors, including mutations found in recurrent and/or refractory GBM or that occur in primary GBM. Mutations found in primary, recurrent and/or refractory GBM (and subtypes thereof) include but are not limited to e.g., IDH1 mutation, TP53 mutation, ALK mutation, RRM1 mutation, TUBB3 mutation, ATRX mutation, BRAF mutation, PTEN mutation, PDGFRA mutation, PTPN11 mutation, and SMARCA4 mutation. In some instances, methods may employ an antigen-specific therapeutic specific for one or more killing antigens, where the one or more killing antigens include one or more commonly mutated proteins, including surface expressed proteins.

In some instances, methods of the present disclosure may be employed to treat subjects that do not necessarily present with a heterogeneous GBM, including primary and non-primary GBMs, but are at an increased risk of developing such a heterogeneous GBM. For example, a subject having an apparently homogeneous EGFRvIII(+) GBM may be treated with a circuit to prophylactically surveil a subject for GBM cells expressing one or more mutations that occur in GBM. In some instances, a subject having an EGFRvIII(+) GBM, e.g., whether or not an apparently homogeneous EGFRvIII(+) GBM, may be treated with a circuit directed to a targeting antigen other than EGFRvIII as described herein in anticipation of the loss of EGFRvIII(+) in the GBM, i.e., EGFRvIII(+) antigen loss.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy.

With respect to the GBM as a whole, desired effects of the described treatments may result in a reduction in the number of cells in the GBM, a reduction in the size of a GBM tumor, a reduction in the overall proliferation of the GBM, a reduction in the overall growth rate of a GBM tumor, etc. For example, an effective treatment is in some cases a treatment that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the treatment. Reductions in the number of cancer cells or the size of the tumor mass may be defined with respect to the heterogeneous tumor as a whole or with respect to the targeted cells of the GBM.

In some embodiments, an effective treatment is a treatment that, when administered alone (e.g., in monotherapy) or in combination (e.g., in combination therapy) with one or more additional therapeutic agents, in one or more doses, is effective to reduce one or more of tumor growth rate, GBM cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, GBM cell number, or tumor mass in the absence of the treatment. Reductions in the tumor growth rate, GBM cell number, or tumor mass may be defined with respect to the heterogeneous tumor as a whole or with respect to the targeted cells of the GBM.

In some instances, treatment may involve activation of an immune cell containing nucleic acid sequences encoding a circuit as described herein. Accordingly, the present disclosure correspondingly presents methods of activating an immune cell, e.g., where the immune cell expresses an EGFRvIII priming/targeting circuit as described herein and is contacted with a first cell of a GBM expressing a EGFRvIII priming antigen and a second cell of the GBM expressing a targeting antigen.

Immune cell activation, as a result of the methods described herein, may be measured in a variety of ways, including but not limited to e.g., measuring the expression level of one or more markers of immune cell activation. Useful markers of immune cell activation include but are not limited to e.g., CD25, CD38, CD40L (CD154), CD69, CD71, CD95, HLA-DR, CD137 and the like. For example, in some instances, upon antigen binding by an immune cell receptor an immune cell may become activated and may express a marker of immune cell activation (e.g., CD69) at an elevated level (e.g., a level higher than a corresponding cell not bound to antigen). Levels of elevated expression of activated immune cells of the present disclosure will vary and may include an increase, such as a 1-fold or greater increase in marker expression as compared to un-activated control, including but not limited to e.g., a 1-fold increase, a 2-fold increase, a 3-fold increase, a 4-fold increase, etc.

In some instances, an immune cell modified to encode a circuit of the present disclosure, when bound to a targeted antigen, may have increased cytotoxic activity, e.g., as compared to an un-activated control cell. In some instances, activated immune cells encoding a subject circuit may show 10% or greater cell killing of antigen expressing target cells as compared to un-activated control cells. In some instances, the level of elevated cell killing of activated immune cells will vary and may range from 10% or greater, including but not limited to e.g., 20% or greater, 30% or greater, 40% or greater, 50% or greater, 60% or greater, 70% or greater, 80% or greater, 90% or greater, etc., as compared to an appropriate control.

In some instances, treatment may involve modulation, including induction, of the expression and/or secretion of a cytokine by an immune cell containing nucleic acid sequences encoding a circuit as described herein. Non-limiting examples of cytokines, the expression/secretion of which may be modulated, include but are not limited to e.g., Interleukins and related (e.g., IL-1-like, IL-1α, IL-1β, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.), Interferons (e.g., IFN-α, IFN-β, IFN-γ, etc.), TNF family (e.g., CD154, LT-β, TNF-α, TNF-β, 4-1BBL, APRIL, CD70, CD153, CD178, GITRL, LIGHT, OX40L, TALL-1, TRAIL, TWEAK, TRANCE, etc.), TGF-β family (e.g., TGF-β(1, TGF-β2, TGF-β3, etc.) and the like.

In some instances, activation of an immune cell through a circuit of the present disclosure may induce an increase in cytokine expression and/or secretion relative to that of a comparable cell where the circuit is not present or otherwise inactive. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

Conventional Treatments and Combination Therapy

As will be readily understood, the methods of treating described herein may, in some instances, be combined with one or more conventional treatments. For example, in the case of oncology for GBM, the methods described herein may, in some instances, be combined with a conventional GBM therapy including but not limited to e.g., conventional chemotherapy, conventional radiation therapy, conventional immunotherapy, surgery, etc. Also as described above, in some instances, the methods of treating described herein may be employed following conventional therapy, e.g., to treat a heterogeneous GBM that is refractory to a conventional therapy, to treat a heterogeneous GBM that is recurrent after a conventional therapy, to treat a subject for MRD following conventional therapy, and the like.

In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Standard GBM therapies include surgery (e.g., surgical removal of cancerous tissue), radiation therapy, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Antibodies suitable for use in, or under investigation for, GBM treatment include, but are not limited to, naked antibodies, e.g., trastuzumab (Herceptin), bevacizumab (Avastin™) cetuximab (Erbitux™), panitumumab (Vectibix™), Ipilimumab (Yervoy™), rituximab (Rituxan), alemtuzumab (Lemtrada™), Oregovomab (OvaRex™), Lambrolizumab (pembrolizumab, MK-3475, Keytruda™), ranibizumab (Lucentis™) etc., and conjugated antibodies, e.g., conjugated antibodies of those listed above and the like.

Conventional cancer therapies also include targeted therapies for cancer including but not limited to e.g., Bevacizumab (Avastin) targeting VEGF ligand (approved for use in Glioblastoma) and the like.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.;

phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some instances, methods of treating a subject for cancer may further include administering an agent which enhances the activity of the treatment. Such agents that enhance the activity of the treatment will vary widely and may include but are not limited to e.g., agents that inhibit an inhibitor molecule. Suitable inhibitory molecules that may be targeted include but are not limited to e.g., PD1, PD-L1, CTLA4, TIM3, LAG3, VISTA, BTLA, TIGIT, LAIR1, CD160, 2B4 and TGFR beta.

Inhibiting of inhibitory molecules may be achieved by any convenient method including but not limited to e.g., the administration of a direct inhibitor of the inhibitory molecule (e.g., an antibody that binds the inhibitory molecule, a small molecule antagonist of the inhibitory molecule, etc.), administration of an agent that inhibits expression of the inhibitory molecule (e.g., an inhibitory nucleic acid, e.g., a dsRNA, e.g., an siRNA or shRNA targeting a nucleic acid encoding the inhibitory molecule), an indirect inhibitor of the inhibitory signaling, and the like. In some instances, an agent that may be administered may be an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy (Bristol-Myers Squibb)), Tremelimumab (Pfizer, formerly known as ticilimumab, CP-675, 206)), TIM3, LAG3, or the like.

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a GBM, including e.g., a primary GBM, a recurrent GBM, and the like.

Determining when combination therapies, e.g., involving the administration of one or more agents that ameliorates one or more side effects of a therapy described herein or involving the administration of one or more agents that enhances a therapy described herein, are indicated and the specifics of the administration of such combination therapies are within the skill of the relevant medical practitioner. In some instances, dosage regimens and treatment schedules of combination therapies may be determined through clinical trials.

Testing

As summarized above, the methods of the present disclosure may, in some instances, include testing, where such testing may include but is not limited to e.g., testing of the subject, testing of a biological sample obtained from the subject, and the like. In some instances, methods of the present disclosure may include testing and/or evaluating a subject for a heterogeneous GBM. Testing may be employed, in some instances, to determine or identify whether a subject has a heterogeneous GBM or whether a GBM, in a subject known to have such, is a heterogeneous GBM.

In some instances, a GBM of a subject may be tested or evaluated to determine, detect or identify whether the GBM expresses one or more particular antigens, including but not limited to e.g., an EGFRvIII antigen and/or a targeting antigen, including but not limited to e.g., Ephrin type-A receptor 2 (EphA2), Ephrin type-A receptor 3 (EphA3), a Interleukin-13 receptor (IL13R) (e.g., IL13RA1 or IL13RA2), Epidermal growth factor receptor (EGFR), erb-b2 receptor tyrosine kinase 2 (ERBB2), combinations thereof and the like. In some instances, whether a method of the present disclosure is employed and/or the particular combination of EGFRvIII priming antigen and targeting antigen(s) employed in a subject circuit may be determined based on testing the subject for particular antigen expression in the cells of the subject's GBM.

Subjects suitable for testing will include those that have or have not been previously treated for a GBM including a heterogeneous GBM. For example, in some instances, a subject may have been recently diagnosed with a GBM and the subject may be tested, e.g., to evaluate the presence of EGFRvIII priming antigen and/or one or more targeting antigens, before any treatment of the diagnosed GBM. In some instances, the subject may have been previously treated for a GBM and the subject may be tested, e.g., to evaluate the presence of EGFRvIII priming antigen and/or one or more targeting antigens, after treatment of the diagnosed GBM, including e.g., where the subject's GBM is responsive or refractory to the prior treatment. In some instances, the subject may be undergoing treatment for a GBM and the subject may be tested, e.g., to evaluate the presence of EGFRvIII priming antigen and/or one or more targeting antigens, during the treatment of the diagnosed GBM, including e.g., where the subject's GBM is responsive or refractory to the ongoing treatment or where the subject's response is as yet unknown.

Testing of a subject may include assaying a biological sample obtained from the subject. Useful biological samples may include but are not limited to e.g., biopsy (e.g., a GBM tumor biopsy, etc.), blood samples, and the like. Any convenient method of collecting a biological sample may find use in the herein described methods including but not limited to e.g., needle biopsy, stereotactic biopsy, open biopsy, and the like.

In a brain tumor needle biopsy, a small cut may be made and a small hole, called a burr hole, may be drilled in the skull. A narrow, hollow needle may be inserted through the hole, and tumor tissue may be removed from the core of the needle. In a stereotactic biopsy (a.k.a. a "closed" biopsy) of a brain tumor, the same general procedure may be employed as described for a needle biopsy; however, a computer-assisted guidance system that aids in the location and diagnosis of the tumor may be employed. A computer, using information from a CT or MRI scan, may provide precise information about a tumor's location and its position relative to other structures in the brain. Stereotactically guided equipment might be moved into the burr hole to remove a sample of the tumor. In an open biopsy of a brain tumor a tissue sample is taken during an operation while the tumor is exposed. The sample, regardless of the biopsy method employed for collection, may then be sent for study and review, e.g., by a pathologist.

Any convenient method of assaying a biological sample may find use in the herein described methods including but not limited to e.g., a blood chemistry test, cancer gene mutation testing, complete blood count (CBC), cytogenetic analysis, immunophenotyping, tumor marker tests, histology, cytology (including e.g., flow cytometry, including FACS), immunohistochemistry, gene expression analysis, proteomics, in situ hybridization, and the like. For example, in some instances, immunohistochemistry and/or in situ hybridization may be performed on a biopsy sample obtained from the subject, e.g., to detect the expression of one or more antigens. In some instances, cytology may be performed on a blood sample from the subject, e.g., to detect circulating tumor cells (CTCs).

In some instances, antigen detection in a biological sample may include molecular detection of antigen transcript. Any convenient method of transcript detection may be employed including but not limited to PCR-based assays. Antigen transcript detection may find use in various embodiments of the herein described methods, including but not limited to e.g., where the methods include determining whether one or more cells from a sample of a subject express EGFRvIII, EGFR or both EGFRvIII, EGFR and/or performing quantification of the level(s) of expression thereof.

In some instances, testing of a subject may include multi-sampling. Multi-sampling, as used herein, generally refers to the process of taking multiple samples of a suspected tumor and/or multiple samples of multiple tumors present in a subject. Multi-sampling may be performed at one instance, e.g., where multiple samples are collected from various locations during one period of collection, or over multiple instances, e.g., were one or more sites are sampled over at multiple instances over a period of time. Multi-sampling may find use in subject with heterogeneous cancers, e.g., to ensure that the heterogeneity of a cancer or tumor is sufficiently sampled, e.g., to detect the cellular distribution and/or antigen distribution of a particular cancer or tumor.

In some instances, a subject may be evaluated, in certain contexts, through one or more of the following diagnostics procedures: 3D CT angiography, Angiography, Anoscopy, Autofluorescence bronchoscopy/fluorescence bronchoscopy, Barium swallow or enema, Biopsy, Bone Marrow Aspiration and Biopsy, Bone Scan, Bronchoscopy, CA-125 test, CAD for mammography, CTC Test, Chest x-ray, Colonoscopy, Complete Blood Count Test, Computed Tomography Scan, CT-guided biopsy, DEXA scan, Digital Breast Tomosynthesis, Electrocardiogram, Endobronchial ultrasound, Endoscopic ultrasound, ERCP, Flow cytometry, Full-field digital mammography, Genetic testing, Large bore CT scanner/RT with simulation, Lumbar puncture, Magnetic Resonance Imaging, Mammography, Miraluma breast imaging, MRI-Guided Breast Biopsy, Multi-detector CT scanner, Multiple-gated acquisition (MUGA) scan, Navigational Bronchoscopy, Nuclear Medicine Imaging, Oncotype DX Test, Pap test, Pelvic exam, PET Scan, PET-CT Scan, Radiofrequency ablation, Sentinel lymph node biopsy, Spiral CT, Tumor marker testing, Tumor molecular profiling, Ultrasound, Video Capsule Endoscopy, X-ray, and the like.

Diagnostic procedures may be performed for a variety of reasons including but not limited to e.g., to screen for GBM or precancerous conditions indicative of increased risk of GBM (e.g., CMV infection) before a person has any symptoms of disease; to help diagnose GBM; to provide information about the stage of a GBM; to provide information about the malignancy of a GBM; to provide information about the size and/or extent of a primary GBM; to provide information about whether or not a GBM has metastasized; to plan treatment; to monitor a patient's general health during treatment; to check for potential side effects of the treatment; to determine whether a GBM is responding to treatment; to find out whether a GBM has recurred; etc.

Antigens

Antigens employed in the present methods include, as described above, the EGFRvIII priming antigen and one or more targeting antigens and others in some instances. In instances where the targeted cell is targeted for killing, the subject targeting antigen may be referred to herein as a "killing antigen". Such terms may, but need not necessarily, be used interchangeably where appropriate.

As described herein with regards to cancer heterogeneity, the relative presence of an antigen and/or the relative presence of cells expressing an antigen will vary. In general, less than 100% of the cells of a heterogeneous cancer treated with the described methods will express EGFRvIII antigen, including but not limited to e.g., where less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20% of cells of the heterogeneous cancer express EGFRvIII antigen.

In some instances, all cells of a heterogeneous GBM may express an employed killing antigen. Such heterogeneous GBMs may be said to be homogeneous for killing antigen expression. In some instances, a heterogeneous GBM may be heterogeneous for EGFRvIII antigen expression but homogeneous for killing antigen expression. Accordingly, in certain embodiments, certain cells of the heterogeneous GBM may express both the priming antigen and the killing antigen. In such instances, the methods of the present disclosure may be employed where the heterogeneous GBM still includes cells that express the killing antigen but not the priming antigen.

In some instances, a heterogeneous GBM may be heterogeneous for both EGFRvIII priming antigen expression and targeting/killing antigen expression, including where the targeting/killing antigen is expressed by less than 100% of the cells of the heterogeneous GBM. In some instances, the targeting/killing antigen may be expressed in a majority of the cells of the heterogeneous GBM but less than 100% of the cells, including but not limited to e.g., where more than 95%, more than 90%, more than 85%, more than 80%, more than 75%, more than 70%, more than 65%, more than 60%, more than 55%, or more than 50% of the cells of the heterogeneous GBM.

In some instances, multiple antigen-specific therapeutics targeting different targeting/killing antigens may be employed. In some instances, antigen-specific therapeutics targeting multiple different targeting/killing antigens may be employed. In some instances, multiple targeting/killing antigens may be targeted in cases where targeting/killing antigen expression is heterogeneous, including where e.g., one or more of the subject targeting/killing antigens is expressed by a majority of the cells of the GBM, where one or more of the subject targeting/killing antigens is expressed by a minority of the cells of the GBM, and the like. In some instances, the targeting of two or more different targeting/killing antigens results in combination of antigens employed targeting 100% or nearly 100% (e.g., 99% or greater, 98% or greater, 95% or greater, 90% or greater, etc.) of the cells of the GBM.

Useful antigens that may be employed as targeting antigens include but are not limited to e.g., Ephrin type-A receptor 2 (EphA2), Ephrin type-A receptor 3 (EphA3), a Interleukin-13 receptor (IL13R) (e.g., IL13RA1 or IL13RA2), Epidermal growth factor receptor (EGFR), erb-b2 receptor tyrosine kinase 2 (ERBB2) and the like. In some instances, EGFRvIII may find use as a targeting antigen. For example, in some instances, EGFRvIII may be employed as both a priming antigen and a killing antigen, including but not limited to e.g., as in a AND-OR gate where EGFRvIII functions as a priming antigen to induce expression of one or more antigen-specific therapeutics specific for EGFRvIII as a first targeting/killing antigen and a second targeting/killing antigen. In such instances, the second targeting/killing antigen may, but need not necessarily, be selected from EphA2, EphA3, IL13RA1, IL13RA2, EGFR, and ERBB2.

In some instances, useful targeting/killing antigens include Ephrin type-A receptor 2 (EphA2). EphA2 is a receptor tyrosine kinase encoded by the EPH receptor A2 gene located at 1p36.13 in humans. EphA2 protein may be found in at least two isoforms in humans, including EphA2 Isoform 1 having the following amino acid sequence:

```
                                          (SEQ ID NO: 1)
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIMGQFSHHNIIRLEGVISKYKPMMIITEYMENGAL

DKFLREKDGEFSVLQLVGMLRGIAAGMKYLANMNYVHRDLAARNILVNSN

LVCKVSDFGLSRVLEDDPEATYTTSGGKIPIRWTAPEAISYRKFTSASDV

WSFGIVMWEVMTYGERPYWELSNHEVMKAINDGFRLPTPMDCPSAIYQLM

MQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVR

LPGHQKRIAYSLLGLKDQVNTVGIPI;
``` and EphA2 Isoform 2 having the following amino acid sequence:

```
                                          (SEQ ID NO: 2)
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD
```

```
GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKVTPRGAGLALAGPTAGDRLVT.
```

In some instances, the methods described herein may employ an antigen-specific therapeutic that specifically binds EphA2, including e.g., human EphA2 Isoform 1, human EphA2 Isoform 2, or both human EphA2 Isoform 1 and human EphA2 Isoform 2.

In some instances, useful EphA2 binding domains may include antibody based EphA2 binding domains, including but not limited to an EphA2 scFv. In some instances, a useful EphA2 scFv may have the following amino acid sequence or a variant thereof:

```
                                          (SEQ ID NO: 3)
EIVLTQSPGTLSLSPGERATLSCRASQSVSSSNLAWYQQKPGQAPRLLIY

GASSRATGVPDRFSGSGSGTDFTLTISRLEPEDFAVYYCQQSSSYPWTFG

QGTKVEIKRTGGGGSGAGGSGGGGTGGGGSEVDLLESGGGLVQPGGSLRL

SCAASGFTFSRYWMHWVRQAPGKGLEWVSSISPYDGETNYADSVKGRFTI

SRDNSKNTLYLQMNSLRAEDTAVYYCARISEWYNWAVDVFDYWGQGTLVT

VSS;
``` including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, a useful EphA2 scFv may have the following amino acid sequence or a variant thereof:

```
                                          (SEQ ID NO: 4)
QVQLLESGGGLVQPGGSLRLSCAASGFTFSSYTMSWVRQAPGQALEWMGT

ISSGGTYTYYPDSVKGRFTISRDNAKNSLYLQMNSLRAEDTAVYYCAREA

IFTYWGRGTLVTSSGGGGSGGGGSGGGGSDIQLTQSPSSLSASVGDRVTI

TCKASQDINNYLSWYQQKPGQAPRLLIYRANRLVDGVPDRFSGSGYGTDF

TLTINNIESEDAAYYFCLKYDVFPYTFGQGTKVEIKS;
``` including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful EphA2 binding domains include those described in Goldgur et al., Growth Factors. (2014) 32(6):214-22 and Damschroder et al., Mol Immunol. (2007) 44(11):3049-60; the disclosures of which are incorporated herein by reference in their entirety.

In some instances, useful targeting/killing antigens include Ephrin type-A receptor 3 (EphA3). EphA3 is a receptor tyrosine kinase encoded by the EPH receptor A3 gene located at 3p11.1 in humans. EphA3 protein may be found in at least two isoforms, including EphA3 Isoform 1 having the following amino acid sequence:

```
                                          (SEQ ID NO: 5)
MDCQLSILLLLSCSVLDSFGELIPQPSNEVNLLDSKTIQGELGWISYPSH

GWEEISGVDEHYTPIRTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDSFSISGESSQVVMIAISAA

VAIILLTVVIYVLIGRFCGYKSKHGADEKRLHFGNGHLKLPGLRTYVDPH

TYEDPTQAVHEFAKELDATNISIDKVVGAGEFGEVCSGRLKLPSKKEISV

AIKTLKVGYTEKQRRDFLGEASIMGQFDHPNIIRLEGVVTKSKPVMIVTE

YMENGSLDSFLRKHDAQFTVIQLVGMLRGIASGMKYLSDMGYVHRDLAAR

NILINSNLVCKVSDFGLSRVLEDDPEAAYTTRGGKIPIRWTSPEAIAYRK

FTSASDVWSYGIVLWEVMSYGERPYWEMSNQDVIKAVDEGYRLPPPMDCP

AALYQLMLDCWQKDRNNRPKFEQIVSILDKLIRNPGSLKIITSAAARPSN

LLLDQSNVDITTFRTTGDWLNGVWTAHCKEIFTGVEYSSCDTIAKISTDD

MKKVGVTVVGPQKKIISSIKALETQSKNGPVPV;
``` and EphA3 Isoform 2 having the following amino acid sequence:

```
                                          (SEQ ID NO: 6)
MDCQLSILLLLSCSVLDSFGELIPQPSNEVNLLDSKTIQGELGWISYPSH

GWEEISGVDEHYTPIRTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDCMYYFNAV.
```

In some instances, the methods described herein may employ an antigen-specific therapeutic that specifically binds EphA3, including e.g., human EphA3 Isoform 1, human EphA3 Isoform 2, or both human EphA3 Isoform 1 and human EphA3 Isoform 2.

In some instances, useful targeting/killing antigens include receptors for Interleukin-13 (IL13). IL13 is an immunoregulatory cytokine encoded by the interleukin 13 gene located at 5q31.1 in humans, which is a ligand for IL13R proteins: interleukin 13 receptor subunit alpha 1

(IL13RA1) and interleukin 13 receptor subunit alpha 2 (IL13RA2). An exemplary amino acid sequence of human IL13 is as follows:

(SEQ ID NO: 7)
MHPLLNPLLLALGLMALLLTTVIALTCLGGFASPGPVPPSTALRELIEEL

VNITQNQKAPLCNGSMVWSINLTAGMYCAALESLINVSGCSAIEKTQRML

SGFCPHKVSAGQFSSLHVRDTKIEVAQFVKDLLLHLKKLFREGRFN.

IL13RA1 is encoded by the interleukin 13 receptor subunit alpha 1 gene, located in humans at Xq24, and is a subunit of the interleukin 13 receptor which forms a receptor complex with IL4 receptor alpha, a subunit shared by IL13 and IL4 receptors. IL13RA1 is a primary IL13-binding subunit of the IL13 receptor. IL13RA1 protein may be found in at least two isoforms, including IL13RA1 Isoform 1 having the following amino acid sequence:

(SEQ ID NO: 8)
MEWPARLCGLWALLLCAGGGGGGGAAPTETQPPVTNLSVSVENLCTVIW

TWNPPEGASSNCSLWYFSHFGDKQDKKIAPETRRSIEVPLNERICLQVGS

QCSTNESEKPSILVEKCISPPEGDPESAVTELQCIWHNLSYMKCSWLPGR

NTSPDTNYTLYYWHRSLEKIHQCENIFREGQYFGCSFDLTKVKDSSFEQH

SVQIMVKDNAGKIKPSFNIVPLTSRVKPDPPHIKNLSFHNDDLYVQWENP

QNFISRCLFYEVEVNNSQTETHNVFYVQEAKCENPEFERNVENTSCFMVP

GVLPDTLNTVRIRVKTNKLCYEDDKLWSNWSOEMSIGKKRNSTLYITMLL

IVPVIVAGAIIVLLLYLKRLKIIIFPPIPDPGKIFKEMFGDONDDTLHWK

KYDIYEKOTKEETDSVVLIENLKKASQ;

and IL13RA1 Isoform 2 having the following amino acid sequence:

(SEQ ID NO: 9)
MEWPARLCGLWALLLCAGGGGGGGAAPTETQPPVTNLSVSVENLCTVIW

TWNPPEGASSNCSLWYFSHFGDKQDKKIAPETRRSIEVPLNERICLQVGS

QCSTNESEKPSILVEKCISPPEGDPESAVTELQCIWHNLSYMKCSWLPGR

NTSPDTNYTLYYWHRSLEKIHQCENIFREGQYFGCSFDLTKVKDSSFEQH

SVQIMVKDNAGKIKPSFNIVPLTSRVKPDPPHIKNLSFHNDDLYVQWENP

QNFISRCLFYEVEVNNSQTETHNVFYVRF.

IL13RA2 is encoded by the interleukin 13 receptor subunit alpha 2 gene, located in humans at Xq23, and is a subunit of the interleukin 13 receptor complex. IL13RA2 binds IL13 with high affinity, but lacks cytoplasmic domain. IL13RA2 protein may be found in at least one isoform, including IL13RA2 having the following amino acid sequence:

(SEQ ID NO: 10)
MAFVCLAIGCLYTFLISTTFGCTSSSDTEIKVNPPQDFEIVDPGYLGYLY

LQWQPPLSLDHFKECTVEYELKYRNIGSETWKTIITKNLHYKDGFDLNKG

IEAKIHTLLPWQCTNGSEVQSSWAETTYWISPQGIPETKVQDMDCVYYNW

QYLLCSWKPGIGVLLDTNYNLFYWYEGLDHALQCVDYIKADGQNIGCRFP

YLEASDYKDFYICVNGSSENKPIRSSYFTFQLQNIVKPLPPVYLTFTRES

SCEIKLKWSIPLGPIPARCFDYEIEIREDDTTLVTATVENETYTLKTTNE

TRQLCFVVRSKVNIYCSDDGIWSEWSDKQCWEGEDLSKKTLLRFWLPFGF

ILILVIFVTGLLLRKPNTYPKMIPEFFCDT.

In some instances, the methods described herein may employ an antigen-specific therapeutic that specifically binds an IL13R, including IL13RA1 and/or IL13RA2, including e.g., human IL13RA1 Isoform 1, human IL13RA1 Isoform 2, human IL13RA2, or any combination thereof. In some instances, useful IL13R binding domains may be derived from IL13, including but not limited to IL13 conjugation products (e.g., wild-type or mutated IL13 conjugated to one or more moieties), derivatives or mutants of IL13, e.g., IL13 muteins, and the like. Useful muteins include but are not limited to e.g., IL13 muteins including one or more amino acid substitutions including E13K and/or K105R.

In some instances, as summarized above, useful IL13R binding domains may include a ligand-based binding domain derived from IL13, including but not limited to an IL13 mutein-based binding domain. In some instances, a useful IL13 mutein-based binding domain may have the following amino acid sequence or a variant thereof:

(SEQ ID NO: 11)
LTCLGGFASPGPVPPSTALRKLIEELVNITQNQKAPLCNGSMVWSINLTA

GMYCAALESLINVSGCSAIEKTQRMLSGFCPHKVSAGQFSSLHVRDTKIE

VAQFVKDLLLHLRKLFREGRFN;

including e.g., where the useful IL13 mutein-based binding domain has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful IL13R binding domains include those described in Krebs et al., Cytotherapy. (2014) 16(8): 1121-31; the disclosure of which is incorporated herein by reference in its entirety.

In some instances, useful targeting/killing antigens include epidermal growth factor receptor (EGFR, also known as Proto-oncogene c-ErbB-1, Receptor tyrosine-protein kinase erbB-1, ERBB, HER1, mENA, ERBB1, PIG61, and NISBD2). EGFR is a receptor tyrosine kinase encoded by the epidermal growth factor receptor gene, present at 7p11.2 in humans. Known ligands of EGFR include EGF, TGFA/TGF-alpha, amphiregulin, epigen/EPGN, BTC/betacellulin, epiregulin/EREG and HBEGF/heparin-binding EGF. EGFR protein may be found in at least four isoforms, including EGFR Isoform 1 having the following amino acid sequence:

(SEQ ID NO: 12)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

-continued
```
CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA,
```

EGFR Isoform 2 having the following amino acid sequence:

```
                                     (SEQ ID NO: 13)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGLS,
```

EGFR Isoform 3 having the following amino acid sequence:

```
                                     (SEQ ID NO: 14)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGPGNESLKAMLFCLFKLSSCNQSN

DGSVSHQSGSPAAQESCLGWIPSLLPSEFQLGWGGCSHLHAWPSASVIIT

ASSCH,
``` and EGFR Isoform 4 having the following amino acid sequence:

```
                                     (SEQ ID NO: 15)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGS.
```

In some instances, the methods described herein may employ an antigen-specific therapeutic that specifically binds an EGFR, including human EGFR, including e.g., human EGFR Isoform 1, human EGFR Isoform 2, human EGFR Isoform 3, EGFR Isoform 4, or any combination thereof.

In some instances, useful targeting/killing antigens include Erb-b2 receptor tyrosine kinase 2 (ERBB2; also known as Metastatic lymph node gene 19 protein, Proto-oncogene Neu, Proto-oncogene c-ErbB-2, Tyrosine kinase-type cell surface receptor HER2, NEU, NGL, HER2, TKR1, CD340, HER-2, MLN 19, and HER-2/neu). ERBB2 is a protein tyrosine kinase that is encoded by the erb-b2 receptor tyrosine kinase 2 gene, located at 17q12 in humans. ERBB2 protein may be found in various isoforms, including ERBB2 Isoform 1 having the following amino acid sequence:

```
                                     (SEQ ID NO: 16)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK
```

-continued
GSRCWGESSEDCQSLTRTVCAGGCARCKGPLPTDCCHEQCAAGCTGPKHS
DCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVF
ETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRP
EDECVGEGLACHQLCARGHCWGPGPTQCVNCSQFLRGQECVEECRVLQGL
PREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASP
LTSIISAVVGILLVVVLGVVFGILIKRRQQKIRKYTMRRLLQETELVEPL
TPSGAMPNQAQMRILKETELRKVKVLGSGAFGTVYKGIWIPDGENVKIPV
AIKVLRENTSPKANKEILDEAYVMAGVGSPYVSRLLGICLTSTVQLVTQL
MPYGCLLDHVRENRGRLGSQDLLNWCMQIAKGMSYLEDVRLVHRDLAARN
VLVKSPNHVKITDFGLARLLDIDETEYHADGGKVPIKWMALESILRRRFT
HQSDVWSYGVTVWELMTFGAKPYDGIPAREIPDLLEKGERLPQPPICTID
VYMIMVKCWMIDSECRPRFRELVSEFSRMARDPQRFVVIQNEDLGPASPL
DSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQS
LPTHDPSPLQRYSEDPTVPLPSETDGYVAPLTCSPQPEYVNQPDVRPQPP
SPREGPLPAARPAGATLERPKTLSPGKNGVVKDVFAFGGAVENPEYLTPQ
GGAAPQPHPPPAFSPAFDNLYYWDQDPPERGAPPSTFKGTPTAENPEYLG
LDVPV, ERBB2 Isoform 2 having the following amino acid sequence:

(SEQ ID NO: 17)
MPIWKFPDEEGACQPCPINCTHSCVDLDDKGCPAEQRASPLTSIISAVVG
ILLVVVLGVVFGILIKRRQQKIRKYTMRRLLQETELVEPLTPSGAMPNQA
QMRILKETELRKVKVLGSGAFGTVYKGIWIPDGENVKIPVAIKVLRENTS
PKANKEILDEAYVMAGVGSPYVSRLLGICLTSTVQLVTQLMPYGCLLDHV
RENRGRLGSQDLLNWCMQIAKGMSYLEDVRLVHRDLAARNVLVKSPNHVK
ITDFGLARLLDIDETEYHADGGKVPIKWMALESILRRRFTHQSDVWSYGV
TVWELMTFGAKPYDGIPAREIPDLLEKGERLPQPPICTIDVYMIMVKCWM
IDSECRPRFRELVSEFSRMARDPQRFVVIQNEDLGPASPLDSTFYRSLLE
DDDMGDLVDAEEYLVPQQGFFCPDPAPGAGGMVHHRHRSSSTRSGGGDLT
LGLEPSEEEAPRSPLAPSEGAGSDVFDGDLGMGAAKGLQSLPTHDPSPLQ
RYSEDPTVPLPSETDGYVAPLTCSPQPEYVNQPDVRPQPPSPREGPLPAA
RPAGATLERPKTLSPGKNGVVKDVFAFGGAVENPEYLTPQGGAAPQPHPP
PAFSPAFDNLYYWDQDPPERGAPPSTFKGTPTAENPEYLGLDVPV,

ERBB2 Isoform 3 having the following amino acid sequence:

(SEQ ID NO: 18)
MRRLLQETELVEPLTPSGAMPNQAQMRILKETELRKVKVLGSGAFGTVYK
GIWIPDGENVKIPVAIKVLRENTSPKANKEILDEAYVMAGVGSPYVSRLL
GICLTSTVQLVTQLMPYGCLLDHVRENRGRLGSQDLLNWCMQIAKGMSYL
EDVRLVHRDLAARNVLVKSPNHVKITDFGLARLLDIDETEYHADGGKVPI
KWMALESILRRRFTHQSDVWSYGVTVWELMTFGAKPYDGIPAREIPDLLE
KGERLPQPPICTIDVYMIMVKCWMIDSECRPRFRELVSEFSRMARDPQRF
VVIQNEDLGPASPLDSTFYRSLLEDDDMGDLVDAEEYLVPQQGFFCPDPA
PGAGGMVHHRHRSSSTRSGGGDLTLGLEPSEEEAPRSPLAPSEGAGSDVF
DGDLGMGAAKGLQSLPTHDPSPLQRYSEDPTVPLPSETDGYVAPLTCSPQ
PEYVNQPDVRPQPPSPREGPLPAARPAGATLERPKTLSPGKNGVVKDVFA
FGGAVENPEYLTPQGGAAPQPHPPPAFSPAFDNLYYWDQDPPERGAPPST
FKGTPTAENPEYLGLDVPV,

ERBB2 Isoform 4 having the following amino acid sequence:

(SEQ ID NO: 19)
MPRGSWKPQVCTGTDMKLRLPASPETHLDMLRHLYQGCQVVQGNLELTYL
PTNASLSFLQDIQEVQGYVLIAHNQVRQVPLQRLRIVRGTQLFEDNYALA
VLDNGDPLNNTTPVTGASPGGLRELQLRSLTEILKGGVLIQRNPQLCYQD
TILWKDIFHKNNQLALTLIDTNRSRACHPCSPMCKGSRCWGESSEDCQSL
TRTVCAGGCARCKGPLPTDCCHEQCAAGCTGPKHSDCLACLHFNHSGICE
LHCPALVTYNTDTFESMPNPEGRYTFGASCVTACPYNYLSTDVGSCTLVC
PLHNQEVTAEDGTQRCEKCSKPCARVCYGLGMEHLREVRAVTSANIQEFA
GCKKIFGSLAFLPESFDGDPASNTAPLQPEQLQVFETLEEITGYLYISAW
PDSLPDLSVFQNLQVIRGRILHNGAYSLTLQGLGISWLGLRSLRELGSGL
ALIHHNTHLCFVHTVPWDQLFRNPHQALLHTANRPEDECVGEGLACHQLC
ARGHCWGPGPTQCVNCSQFLRGQECVEECRVLQGLPREYVNARHCLPCHP
ECQPQNGSVTCFGPEADQCVACAHYKDPPFCVARCPSGVKPDLSYMPIWK
FPDEEGACQPCPINCTHSCVDLDDKGCPAEQRASPLTSIISAVVGILLVV
VLGVVFGILIKRRQQKIRKYTMRRLLQETELVEPLTPSGAMPNQAQMRIL
KETELRKVKVLGSGAFGTVYKGIWIPDGENVKIPVAIKVLRENTSPKANK
EILDEAYVMAGVGSPYVSRLLGICLTSTVQLVTQLMPYGCLLDHVRENRG
RLGSQDLLNWCMQIAKGMSYLEDVRLVHRDLAARNVLVKSPNHVKITDFG
LARLLDIDETEYHADGGKVPIKWMALESILRRRFTHQSDVWSYGVTVWEL
MTFGAKPYDGIPAREIPDLLEKGERLPQPPICTIDVYMIMVKCWMIDSEC
RPRFRELVSEFSRMARDPQRFVVIQNEDLGPASPLDSTFYRSLLEDDDMG
DLVDAEEYLVPQQGFFCPDPAPGAGGMVHHRHRSSSTRSGGGDLTLGLEP
SEEEAPRSPLAPSEGAGSDVFDGDLGMGAAKGLQSLPTHDPSPLQRYSED
PTVPLPSETDGYVAPLTCSPQPEYVNQPDVRPQPPSPREGPLPAARPAGA

-continued
TLERPKTLSPGKNGVVKDVFAFGGAVENPEYLTPQGGAAPQPHPPPAFSP

AFDNLYYWDQDPPERGAPPSTFKGTPTAENPEYLGLDVPV,

ERBB2 Isoform 5 having the following amino acid sequence:

(SEQ ID NO: 20)
MKLRLPASPETHLDMLRHLYQGCQVVQGNLELTYLPTNASLSFLQDIQEV

QGYVLIAHNQVRQVPLQRLRIVRGTQLFEDNYALAVLDNGDPLNNTTPVT

GASPGGLRELQLRSLTEILKGGVLIQRNPQLCYQDTILWKDIFHKNNQLA

LTLIDTNRSRACHPCSPMCKGSRCWGESSEDCQSLTRTVCAGGCARCKGP

LPTDCCHEQCAAGCTGPKHSDCLACLHFNHSGICELHCPALVTYNTDTFE

SMPNPEGRYTFGASCVTACPYNYLSTDVGSCTLVCPLHNQEVTAEDGTQR

CEKCSKPCARVCYGLGMEHLREVRAVTSANIQEFAGCKKIFGSLAFLPES

FDGDPASNTAPLQPEQLQVFETLEEITGYLYISAWPDSLPDLSVFQNLQV

IRGRILHNGAYSLTLQGLGISWLGLRSLRELGSGLALIHHNTHLCFVHTV

PWDQLFRNPHQALLHTANRPEDECVGEGLACHQLCARGHCWGPGPTQCVN

CSQFLRGQECVEECRVLQGLPREYVNARHCLPCHPECQPQNGSVTCFGPE

ADQCVACAHYKDPPFCVARCPSGVKPDLSYMPIWKFPDEEGACQPCPINC

THSCVDLDDKGCPAEQRASPLTSIISAVVGILLVVVLGVVFGILIKRRQQ

KIRKYTMRRLLQETELVEPLTPSGAMPNQAQMRILKETELRKVKVLGSGA

FGTVYKGIWIPDGENVKIPVAIKVLRENTSPKANKEILDEAYVMAGVGSP

YVSRLLGICLTSTVQLVTQLMPYGCLLDHVRENRGRLGSQDLLNWCMQIA

KGMSYLEDVRLVHRDLAARNVLVKSPNHVKITDFGLARLLDIDETEYHAD

GGKVPIKWMALESILRRRFTHQSDVWSYGVTVWELMTFGAKPYDGIPARE

IPDLLEKGERLPQPPICTIDVYMIMVKCWMIDSECRPRFRELVSEFSRMA

RDPQRFVVIQNEDLGPASPLDSTFYRSLLEDDDMGDLVDAEEYLVPQQGF

FCPDPAPGAGGMVHHRHRSSSTRSGGGDLTLGLEPSEEEAPRSPLAPSEG

AGSDVFDGDLGMGAAKGLQSLPTHDPSPLQRYSEDPTVPLPSETDGYVAP

LTCSPQPEYVNQPDVRPQPPSPREGPLPAARPAGATLERPKTLSPGKNGV

VKDVFAFGGAVENPEYLTPQGGAAPQPHPPPAFSPAFDNLYYWDQDPPER

GAPPSTFKGTPTAENPEYLGLDVPV, and ERBB2 Isoform 6 having the following amino acid sequence:

(SEQ ID NO: 21)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

-continued
ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSPLTSIISAVVGILLVVV

LGVVFGILIKRRQQKIRKYTMRRLLQETELVEPLTPSGAMPNQAQMRILK

ETELRKVKVLGSGAFGTVYKGIWIPDGENVKIPVAIKVLRENTSPKANKE

ILDETISNLFSNFAPRGPSACCEPTCWCHSGKGQDSLPREEWGRQRRFCL

WGCRGEPRVLDTPGRSCPSAPPSSCLQPSLRQPLLLGPGPTRAGGSTQHL

QRDTYGREPRVPGSGRASVNQKAKSAEALMCPQGAGKA.

In some instances, the methods described herein may employ an antigen-specific therapeutic that specifically binds an ERBB2, including human ERBB2, including e.g., human ERBB2 Isoform 1, human ERBB2 Isoform 2, human ERBB2 Isoform 3, human ERBB2 Isoform 4, human ERBB2 Isoform 5, human ERBB2 Isoform 6, or any combination thereof.

In some instances, combinations of two or more targeting antigens may be employed, including but not limited to e.g., where such combinations include EphA2 and EphA3, EphA2 and IL13RA2 (or IL13RA1), EphA2 and EGFR, EphA2 and ERBB2, EphA3 and IL13RA2 (or IL13RA1), EphA3 and EGFR, EphA3 and ERBB2, IL13RA2 (or IL13RA1) and EGFR, IL13RA2 (or IL13RA1) and ERBB2, or EGFR and ERBB2. In some instances, such combinations may find use in an OR gate as described herein. In some instances, a two-headed antigen-specific therapeutic may be employed, including but not limited to e.g., where the two-headed antigen-specific therapeutic binds to EphA2 and EphA3, EphA2 and IL13RA2 (or IL13RA1), EphA2 and EGFR, EphA2 and ERBB2, EphA3 and IL13RA2 (or IL13RA1), EphA3 and EGFR, EphA3 and ERBB2, IL13RA2 (or IL13RA1) and EGFR, IL13RA2 (or IL13RA1) and ERBB2, or EGFR and ERBB2.

In some instances, useful priming and/or targeting/killing antigens include Epidermal growth factor receptor variant III (EGFRvIII). EGFRvIII is a mutant of EGFR where, commonly exons 2-7 of the EGFR gene are deleted as a result of EGFR rearrangement (see e.g., Gan et al. FEBS J. (2013) 280(21):5350-70; the disclosure of which is incorporated herein in its entirety). Methods described herein may employ EGFRvIII as a priming antigen and may include the use of a BTTS (described in more detail herein) that specifically binds EGFRvIII in a circuit employed in the subject methods.

In some instances, circuits of the present disclosure may include an antigen-specific therapeutic that specifically binds an EGFRvIII, including e.g., where EGFRvIII is employed as both a priming antigen and a targeting antigen. For example, an antigen-specific therapeutic that specifically binds an EGFRvIII may be employed in an AND-OR gate where the circuit-containing cells are primed by EGFRvIII to target EGFRvIII or another antigen (including but not limited to e.g., EphA2, EphA3, IL13RA2 (or IL13RA1), EGFR, or ERBB2). In some instances, the targeted antigens of a circuit used in a method of the present disclosure will not include EGFRvIII such that the circuit does not target EGFRvIII, including e.g., where EGFRvIII is utilized solely as a priming antigen.

The amino acid sequence of EGFRvIII may vary, e.g., depending on the particular mutation and/or rearrangement from which a particular EGFRvIII is derived. A non-limiting example of an EGFRvIII amino acid sequence is as follows:

(SEQ ID NO: 22)
MRPSGTAGAAFLALLAALCPASRALEEKKGNYVVTDHGSCVRACGADSYE

MEEDGVRKCKKCEGPCRKVCNGIGIGEFKDSLSINATNIKHFKNCTSISG

DLHILPVAFRGDSFTHTPPLDPQELDILKTVKEITGFLLIQAWPENRTDL

HAFENLEIIRGRTKQHGQFSLAVVSLNITSLGLRSLKEISDGDVIISGNK

NLCYANTINWKKLFGTSGQKTKIISNRGENSCKATGQVCHALCSPEGCWG

PEPRDCVSCRNVSRGRECVDKCNLLEGEPREFVENSECIQCHPECLPQAM

NITCTGRGPDNYIQCAHYIDGPHCVKTCPAGVMGENNTLVWKYADAGHVC

HLCHPNCTYGCTGPGLEGCPTNGPKIPSIATGMVGALLLLLVVALGIGLF

MRRRHIVRKRTLRRLLQERELVEPLTPSGEAPNQALLRILKETEFKKIKV

LGSGAFGTVYKGLWIPEGEKVKIPVAIKELREATSPKANKEILDEAYVMA

SVDNPHVCRLLGICLTSTVQLITQLMPFGCLLDYVREHKDNIGSQYLLNW

CVQIAKGMNYLEDRRLVHRDLAARNVLVKTPQHVKITDFGLAKLLGAEEK

EYHAEGGKVPIKWMALESILHRIYTHQSDVWSYGVTVWELMTFGSKPYDG

IPASEISSILEKGERLPQPPICTIDVYMIMVKCWMIDADSRPKFRELIIE

FSKMARDPQRYLVIQGDERMHLPSPTDSNFYRALMDEEDMDDVVDADEYL

IPQQGFFSSPSTSRTPLLSSLSATSNNSTVACIDRNGLQSCPIKEDSFLQ

RYSSDPTGALTEDSIDDTFLPVPEYINQSVPKRPAGSVQNPVYHNQPLNP

APSRDPHYQDPHSTAVGNPEYLNTVQPTCVNSTFDSPAHWAQKGSHQISL

DNPDYQQDFFPKEAKPNGIFKGSTAENAEYLRVAPQSSEFIGA.

EGFRvIII proteins, and the amino acid sequences thereof, to which an antigen-binding domain of a BTTS or an antigen-specific therapeutic bind may vary from that provided above. For example, in some instances, a subject EGFRvIII variant may include one or more mutations relative to the sequence provided above, including but not limited to e.g., 1 mutation, 2 or less, 3 or less, 4 or less, 5 or less mutations, etc. In some instances, a subject EGFRvIII variant may share 80% or greater sequence identity with the amino acid sequence provided above, including but not limited to e.g., 85% or greater, 90% or greater, 95% or greater, 96% or greater, 97% or greater, 98% or greater, 99% or greater, or 100% sequence identity with the above EGFRvIII sequence.

In some instances, useful EGFRvIII binding domains may include antibody based EGFRvIII binding domains, including but not limited to an EGFRvIII scFv. In some instances, a useful EGFRvIII scFv may have the following amino acid sequence or a variant thereof:

(SEQ ID NO: 23)
DIQMTQSPSSLSASVGDRVTITCRASQGIRNNLAWYQQKPGKAPKRLIYA

ASNLQSGVPSRFTGSGSGTEFTLIVSSLQPEDFATYYCLQHHSYPLTSGG

GTKVEIKGSTSGSGKPGSGEGSEVQVLESGGGLVQPGGSLRLSCAASGFT

FSSYAMSWVRQAPGKGLEWVSAISGSGGSTNYADSVKGRFTISRDNSKNT

LYLQMNSLRAEDTAVYYCAGSSGWSEYWGQGTLVTVSS;

including e.g., where the useful EGFRvIII scFv has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful EGFRvIII binding domains include those described in Morgan et al. Hum Gene Ther. (2012) 23(10):1043-5; the disclosure of which is incorporated herein by reference it its entirety.

Antigen-Specific Therapeutics

As summarized above, in the present methods a BTTS responsive to an EGFRvIII priming antigen may induce the expression of an antigen-specific therapeutic responsive to one or more targeting antigens. Useful antigen-specific therapeutics will vary and may include surfaced expressed and secreted antigen-specific therapeutics. For example, in some instances, an antigen-specific therapeutic used in the methods of the present disclosure may be expressed, in response to the activation of a BTTS, on the surface of an immune cell, i.e., the immune cell genetically modified to encode a EGFRvIII priming/targeting circuit as described herein. In some instances, an antigen-specific therapeutic used in the methods of the present disclosure may be secreted, in response to the activation of a BTTS, from an immune cell, i.e., the immune cell genetically modified to encode a EGFRvIII priming/targeting circuit as described herein.

In general, except where described otherwise, the antigen-specific therapeutic of a herein described circuit will not be expressed in the absence of the activation of the BTTS that induces its expression. Also, except where described otherwise, an antigen-specific therapeutic of a herein described circuit will not be active in the absence of the antigen to which it binds, i.e., without binding the antigen to which the antigen-specific therapeutic is specific. Binding of its respective antigen, or antigens in the case of multi- or bispecific agents, results in activation of the antigen-specific therapeutic. When expressed by, or otherwise engaged with, an immune cell and bound to antigen(s) the antigen-specific therapeutic may activate the immune cell. Activated immune cells may mediate one or more beneficial effects with respect to a heterogeneous GBM of a subject, including those described herein such as but not limited to e.g., cancer cell killing, cytokine release, and the like.

The term "antigen", with respect to the herein described antigen-specific binding domains, is used in a broad sense to refer to essentially any specific binding partner to which the antigen-specific therapeutic binds. As such, any convenient specific binding pair, i.e., specific binding member and specific binding partner pair, may find use in the antigen-specific therapeutics of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a ligand and its binding partner may be a receptor to which the ligand specifically binds.

In some instances, useful ligand-receptor specific binding pairs may include where the specific binding member is a mutein of a ligand having at least one mutation relative to the wild-type ligand, including but not limited to e.g., one or more mutations, two or more mutations, three or more mutations, four or more mutations, five or more mutations, etc. In some instances, useful muteins will have at least 90% sequence identity with the relevant wild-type amino acid sequence, including but not limited to e.g., at least 95%, at least 96%, at least 97%, at least 98%, at least 99%, etc., sequence identity with the relevant wild-type amino acid sequence. In some instances, a mutein employed in the subject polypeptide may have higher affinity for the receptor as compared to the affinity between the receptor and the wild-type ligand.

Antigen-specific therapeutics useful in the methods of the present disclosure will vary and may include but are not limited to e.g., chimeric antigen receptors (CARs), T cell receptors (TCRs), chimeric bispecific binding members, and the like.

Useful CARs include essentially any CAR useful in the treatment of cancer, including single-chain and multi-chain CARs, directed to one or more targeting antigens. A CAR used in the instant methods will generally include, at a minimum, an antigen binding domain, a transmembrane domain and an intracellular signaling domain. An employed CAR may further include one or more costimulatory domains.

Non-limiting examples of CARs that may be employed include those used in commercialized CAR T cell (CART) therapies that are directed to one or more appropriate targeting antigens or have been modified to be directed to one or more appropriate targeting antigens. For example, in some instances, one or more CARs may be employed that target one or more targeting antigens, including but not limited to e.g., EphA2, EphA3, IL13RA2 (or IL13RA1), EGFR, and ERBB2. In some instances, a CAR may be employed that targets EGFRvIII, including where EGFRvIII is the sole antigen targeted by the CAR or one of two or more antigens targeted by the CAR.

Useful CARs that may be modified to be directed to one or more appropriate targeting antigens include but are not limited to those CARs directed to CD19 and BCMA, including e.g., the anti-CD19-4-1BB-CDζCAR expressed by lentivirus loaded CTL019 (Tisagenlecleucel-T) CAR-T cells, also referred to as Kymriah™ (tisagenlecleucel) as commercialized by Novartis (Basel, Switzerland) and the anti-BCMA-4-1BB-CDζCAR expressed by lentivirus loaded CAR-T cells called "bb2121" as commercialized by bluebird bio, Inc. (Cambridge, MA) and Celgene Corporation (Summit, NJ).

Useful CARs, e.g., that may be modified to be directed to an appropriate targeting antigen, or useful domains thereof, e.g., that may be employed in a CAR directed to an appropriate targeting antigens, in some instances may include those described in U.S. Pat. Nos. 9,914,909; 9,821,012; 9,815,901; 9,777,061; 9,662,405; 9,657,105; 9,629,877; 9,624,276; 9,598,489; 9,587,020; 9,574,014; 9,573,988; 9,499,629; 9,446,105; 9,394,368; 9,328,156; 9,233,125; 9,175,308 and 8,822,647; the disclosures of which are incorporated herein by reference in their entirety. In some instances, useful CARs may include or exclude heterodimeric, also referred to as dimerizable or switchable, CARs and/or include or exclude one or more of the domains thereof. Useful heterodimeric CARs and/or useful domains thereof may, in some instances, include those described in U.S. Pat. Nos. 9,587,020 and 9,821,012 as well as U.S. Pub. Nos. US20170081411A1, US20160311901A1, US20160311907A1, US20150266973A1 and PCT Pub. Nos. WO2014127261A1, WO2015142661A1, WO2015090229A1 and WO2015017214A1; the disclosures of which are incorporated herein by reference in their entirety.

As summarized above, in some instances, the antigen binding domain of a CAR, such but not limited to e.g., those described in any one of the documents referenced above, may be substituted or amended with an alternative or additional antigen binding domain directed to a different antigen, such as but not limited to one or more of the antigens described herein, for use in the herein described methods. In such instances, the intracellular portions (i.e., the intracellular signaling domain or the one or more co-stimulatory domains) of the antigen-domain-substituted CAR may or may not be modified.

Useful CARs and/or useful domains thereof may, in some instances, include those that have been or are currently being investigated in one or more clinical trials, including but not limited to the CARs directed to the following antigens (listed with an exemplary corresponding clinical trial number, further information pertaining to which may be retrieved by visiting www(dot)clinicaltrials(dot)gov): AFP, e.g., in NCT03349255; BCMA, e.g., in NCT03288493; CD10, e.g., in NCT03291444; CD117, e.g., in NCT03291444; CD123, e.g., in NCT03114670; CD133, e.g., in NCT02541370; CD138, e.g., in NCT01886976; CD171, e.g., in NCT02311621; CD19, e.g., in NCT02813252; CD20, e.g., in NCT03277729; CD22, e.g., in NCT03244306; CD30, e.g., in NCT02917083; CD33, e.g., in NCT03126864; CD34, e.g., in NCT03291444; CD38, e.g., in NCT03291444; CD5, e.g., in NCT03081910; CD56, e.g., in NCT03291444; CD7, e.g., in NCT02742727; CD70, e.g., in NCT02830724; CD80, e.g., in NCT03356808; CD86, e.g., in NCT03356808; CEA, e.g., in NCT02850536; CLD18, e.g., in NCT03159819; CLL-1, e.g., in NCT03312205; cMet, e.g., in NCT01837602; EGFR, e.g., in NCT03182816; EGFRvIII, e.g., in NCT02664363; EpCAM, e.g., in NCT03013712; EphA2, e.g., in NCT02575261; GD-2, e.g., in NCT01822652; Glypican 3, e.g., in NCT02905188; GPC3, e.g., in NCT02723942; HER-2, e.g., in NCT02547961; kappa immunoglobulin, e.g., in NCT00881920; LeY, e.g., in NCT02958384; LMP1, e.g., in NCT02980315; mesothelin, e.g., in NCT02930993; MG7, e.g., in NCT02862704; MUC1, e.g., in NCT02587689; NKG2D-ligands, e.g., in NCT02203825; PD-L1, e.g., in NCT03330834; PSCA, e.g., in NCT02744287; PSMA, e.g., in NCT03356795; ROR1, e.g., in NCT02706392; ROR1R, e.g., in NCT02194374; TACI, e.g., in NCT03287804; and VEGFR2, e.g., in NCT01218867.

Useful TCRs include essentially any TCR useful in the treatment of cancer, including single-chain and multi-chain TCRs, directed to a targeting antigen. A TCR used in the instant methods will generally include, at a minimum, an antigen binding domain and a modified or unmodified TCR chain, or portion thereof, including but not limited to e.g., a modified or unmodified α-chain, a modified or unmodified β-chain, etc. An employed TCR may further include one or more costimulatory domains. In some instances, a TCR employed herein will include an alpha chain and a beta chain and recognize antigen when presented by a major histocompatibility complex.

Essentially any TCR can be induced by a BTTS using a method of the present disclosure including e.g., TCRs that are specific for any of a variety of epitopes, including, e.g., an epitope expressed on the surface of a cancer cell, a peptide-MHC complex on the surface of cancer cell, and the like. In some cases, the TCR is an engineered TCR.

Non-limiting examples of engineered TCRs, including those having immune cell activation function and that may be modified to include an antigen-binding domain specific for a suitable targeting antigen, useful in the methods described herein include, e.g., antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID: 25483644); Gschweng et al. Immunol Rev. 2014; 257(1): 237-49 (PMID:24329801); Hinrichs et al. Immunol Rev. 2014; 257(1):56-71 (PMID:24329789); Zoete et al. Front Immunol. 2013; 4:268 (PMID:24062738); Man et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Clin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2): e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety.

Useful TCRs include those having wild-type affinity for their respective antigen as well as those having enhanced affinity for their respective antigen. TCRs having enhanced affinity for their respective antigen may be referred to as "affinity enhanced" or "enhanced affinity" TCRs. The affinity of a TCR may be enhanced by any convenient means, including but not limited to binding-site engineering (i.e., rational design), screening (e.g., TCR display), or the like. Non-limiting examples of affinity enhanced TCRs and methods of generating enhanced affinity TCRs include but are not limited to e.g., those described in PCT Pub. Nos. 20150118208, 2013256159, 20160083449; 20140349855, 20100113300, 20140371085, 20060127377, 20080292549, 20160280756, 20140065111, 20130058908, 20110038842, 20110014169, 2003276403 and the like; the disclosures of which are incorporated herein by reference in their entirety. Further engineered TCRs, modified to be directed to an appropriate targeting antigen, that may be expressed in response to release of an intracellular domain of a BTTS of the present disclosure include e.g., those described in PCT Application No. US2017/048040; the disclosure of which is incorporated herein by reference in its entirety.

Useful TCRs, which may be modified to be directed to an appropriate targeting antigen, may, in some instances, also include those described in U.S. Pat. Nos. 9,889,161; 9,889,160; 9,868,765; 9,862,755; 9,717,758; 9,676,867; 9,409,969; 9,115,372; 8,951,510; 8,906,383; 8,889,141; 8,722,048; 8,697,854; 8,603,810; 8,383,401; 8,361,794; 8,283,446; 8,143,376; 8,003,770; 7,998,926; 7,666,604; 7,456,263; 7,446,191; 7,446,179; 7,329,731; 7,265,209; and 6,770,749; the disclosures of which are incorporated herein by reference in their entirety.

As described above, in some instances, the antigen binding domain of a TCR, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., the transmembrane domain, any intracellular signaling domains, etc.) of the antigen-domain-substituted TCR may or may not be modified.

As summarized above, in some instances, useful antigen-specific therapeutics may include those that, upon induction by an activated BTTS, are expressed and secreted from the producing cell, including e.g., where the secreting cell is an immune cell. For example, upon binding of a BTTS expressed by an immune cell, the BTTS may induce expression and secretion of an encoded antigen-specific therapeutic specific for a targeting antigen. The secreted antigen-specific therapeutic may target a target antigen expressing cancer cell in trans, thereby mediating killing of the target cell. As described herein, in some instances, a secreted antigen-specific therapeutic may increase the zone of targeting or the zone of killing of a subject circuit as compared to a similar circuit encoding a non-secreted (e.g., membrane expressed) antigen-specific therapeutic.

Useful secreted antigen-specific therapeutics will vary and in some instances may include but are not limited to e.g., chimeric bispecific binding members. In some instances, useful chimeric bispecific binding members may include those that target a protein expressed on the surface of an immune cell, including but not limited to e.g., a component of the T cell receptor (TCR), e.g., one or more T cell co-receptors. Chimeric bispecific binding members that bind to a component of the TCR may be referred to herein as a TCR-targeted bispecific binding agent. Chimeric bispecific binding members useful in the instant methods will generally be specific for a targeting antigen and may, in some instances, be specific for a targeting antigen and a protein expressed on the surface of an immune cell (e.g., a component of a TCR such as e.g., a CD3 co-receptor).

Non-limiting examples of useful chimeric bispecific binding members include those that bind Ephrin type-A receptor 2 (EphA2), Ephrin type-A receptor 3 (EphA3), an Interleukin-13 receptor (IL13R) (e.g., IL13RA2 or IL13RA1), Epidermal growth factor receptor (EGFR) or erb-b2 receptor tyrosine kinase 2 (ERBB2). Non-limiting examples of useful chimeric bispecific binding members also include those that have been modified to bind EphA2, EphA3, IL13RA2 (or IL13RA1), EGFR or ERBB2.

In some instances, useful chimeric bispecific binding members may include a bispecific T cell engager (BiTE). A BiTE is generally made by fusing a specific binding member (e.g., a scFv) that binds an immune cell antigen to a specific binding member (e.g., a scFv) that binds a cancer antigen (e.g., a tumor associated antigen, a tumor specific antigen, etc.). For example, an exemplary BiTE includes an anti-CD3 scFv fused to an anti-tumor associated antigen (e.g., EpCAM, CD19, etc.) scFv via a short peptide linker (e.g., a five amino acid linker, e.g., GGGGS).

In some instances, a BiTE, suitable for use in the herein described methods may include e.g., an anti-CD3× anti-CD19 BiTE (e.g., Blinatumomab) that has been modified to bind a suitable targeting antigen (including but not limited to e.g., EphA2, EphA3, IL13RA2 (or IL13RA1), EGFR or ERBB2), an anti-EpCAM×anti-CD3 BiTE (e.g., MT110) that has been modified to bind a suitable targeting antigen (including but not limited to e.g., EphA2, EphA3, IL13RA2

(or IL13RA1), EGFR or ERBB2), an anti-CEAxanti-CD3 BiTE (e.g., MT111/MEDI-565) that has been modified to bind a suitable targeting antigen (including but not limited to e.g., EphA2, EphA3, IL13RA2 (or IL13RA1), EGFR or ERBB2), an anti-CD33× anti-CD3 BiTE that has been modified to bind a suitable targeting antigen (including but not limited to e.g., EphA2, EphA3, IL13RA2 (or IL13RA1), EGFR or ERBB2), an anti-HER2 BiTE that has been modified to bind a suitable targeting antigen (including but not limited to e.g., EphA2, EphA3, IL13RA2 (or IL13RA1), EGFR or ERBB2), an anti-EGFR BiTE, an anti-IgE BiTE that has been modified to bind a suitable targeting antigen (including but not limited to e.g., EphA2, EphA3, IL13RA2 (or IL13RA1), EGFR or ERBB2), and the like.

As summarized above, in some instances, the antigen binding domain of a chimeric bispecific binding member, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., linker domain, any immune cell targeting domains, etc.) of the antigen-domain-substituted chimeric bispecific binding member may or may not be modified.

In some instances, a payload induced by binding of a BTTS to its respective priming antigen in a herein described method may include a secreted bio-orthogonal adapter molecule. Such bio-orthogonal adapter molecules may, in some instances, be configured to target and bind a targeting antigen and also bind or be bound by a heterologous polypeptide expressed by an immune cell.

For example, in some instances, a subject circuit employed in the herein described methods may encode, within an immune cell: a BTTS responsive to an EGFRvIII priming antigen; a bio-orthogonal adapter molecule specific for a targeting antigen; and a therapeutic, or portion thereof, which binds the bio-orthogonal adapter molecule. In such a circuit, expression and secretion of the bio-orthogonal adapter molecule is induced upon binding of the BTTS to EGFRvIII. Then, in the presence of both (1) a cancer cell expressing the targeting antigen and (2) the therapeutic that binds the bio-orthogonal adapter molecule, the therapeutic binds the bio-orthogonal adapter molecule which then binds the targeting antigen, thereby activating the therapeutic. The activated therapeutic may then mediate a therapeutic effect (e.g., a cytotoxic effect) on the cancer cell expressing the targeting antigen, including where the targeting antigen is expressed in trans with respect to the EGFRvIII priming antigen. As described herein, in some instances, a secreted bio-orthogonal adapter molecule may increase the zone of targeting or the zone of killing of a subject circuit as compared to a similar circuit encoding a non-secreted (e.g., membrane expressed) antigen-specific therapeutic.

Bio-orthogonal adapter molecules may be employed in various contexts within the herein described methods. For example, in some instances, a bio-orthogonal adapter molecule may be employed that includes a diffusible antigen binding portion of an antigen-specific therapeutic, such as e.g., a diffusible antigen binding portion of a CAR, a diffusible antigen binding portion of a TCR, or the like. In some instances, such diffusible antigen binding portion of antigen-specific therapeutics may be referred to a "diffusible head", including e.g., a "diffusible CAR head", a "diffusible TCR head", and the like. In some instances, a diffusible antigen binding portion may be specific for one or more of EphA2, EphA3, IL13RA2 (or IL13RA1), EGFR and/or ERBB2.

In some instances, the therapeutic may bind directly to the bio-orthogonal adapter molecule. Strategies for direct binding of the therapeutic to the bio-orthogonal adapter molecule may vary. For example, in some instances, the therapeutic may include a binding domain (e.g., such as an orthogonal antibody or fragment thereof) that binds a binding moiety (e.g., an orthogonal epitope to which an antibody may be directed) covalently attached to the bio-orthogonal adapter. As a non-limiting example, a therapeutic may include a binding domain to a non-naturally occurring epitope, e.g., an anti-fluorescein antibody or a fragment thereof, and the bio-orthogonal adapter molecule may include the epitope, e.g., a fluorescein, covalently attached thereto. In some instances, the configuration of the bio-orthogonal adapter molecule and therapeutic interaction may be reversed as compared to that previously described, including e.g., where the therapeutic includes a covalently attached epitope and the bio-orthogonal adapter molecule includes a binding domain to the epitope. Useful epitopes will vary and may include but are not limited to e.g., small molecule-based epitopes, peptide-based epitopes (e.g., peptide neo-epitopes), oligonucleotide-based epitopes, and the like. The epitope-binding domains will vary correspondingly and may include but are not limited to e.g., small molecule binding domains, peptide binding domains, oligonucleotide binding domains, and the like.

Non-limiting examples of useful bio-orthogonal adapter molecules, and the domains that bind thereto, include but are not limited to e.g., the peptide neo-epitopes and the antibody binding domains that bind thereto as used in switchable CAR (sCAR) T cells, including but not limited to e.g., those described in Rodgers et al. Proc Natl Acad Sci USA. (2016) 113(4):E459-68 and Cao et al., Angew Chem Int Ed Engl. 2016 Jun. 20; 55(26):7520-4 as well as PCT Pub. No. WO2016168773; the disclosures of which are incorporated herein by reference in their entirety.

In some instances, the therapeutic may bind indirectly to the bio-orthogonal adapter molecule, including e.g., where binding is mediated by a diffusible dimerizing agent. Non-limiting examples of suitable dimerizing agents, and the dimerizing domains that bind thereto, include protein dimerizers.

Protein dimerizers generally include polypeptide pairs that dimerize, e.g., in the presence of or when exposed to a dimerizing agent. The dimerizing polypeptide pairs of a protein dimerizer may homo-dimerize or hetero-dimerize (i.e., the dimerizing polypeptide pairs may include two of the same polypeptide that form a homodimer or two different polypeptides that form a heterodimer). Non-limiting pairs of protein dimerizers (with the relevant dimerizing agent in parentheses) include but are not limited to e.g., FK506 binding protein (FKBP) and FKBP (rapamycin); FKBP and calcineurin catalytic subunit A (CnA) (rapamycin); FKBP and cyclophilin (rapamycin); FKBP and FKBP-rapamycin associated protein (FRB) (rapamycin); gyrase B (GyrB) and GyrB (coumermycin); dihydrofolate reductase (DHFR) and DHFR (methotrexate); DmrB and DmrB (AP20187); PYL and ABI (abscisic acid); Cry2 and CIB1 (blue light); GAI and GID1 (gibberellin); and the like. Further description, including the amino acid sequences, of such protein dimerizers is provided in U.S. Patent Application Publication No. US 2015-0368342 A1; the disclosure of which is incorporated herein by reference in its entirety.

Useful protein dimerizers also include those nuclear hormone receptor derived protein dimerizers that dimerize in the presence of a dimerizing agent described in PCT Pub. No. WO 2017/120546 and U.S. Patent Pub. No. US 2017/0306303 A1; the disclosures of which are incorporated by reference herein in their entirety, and the like. Such nuclear hormone receptor derived dimerizers will generally include a first member of the dimerization pair that is a co-regulator of a nuclear hormone receptor and a second member of the dimerization pair comprises an LBD of the nuclear hormone receptor.

Where a bio-orthogonal adapter molecule is employed in a subject circuit, the expression of the therapeutic, which binds the bio-orthogonal adapter molecule to mediate targeting antigen recognition, may or may not be controlled by the circuit. Put another way, the expression of the therapeutic may or may not be tied to the activation of the BTTS (e.g., the binding of the BTTS to EGFRvIII or another antigen) of the circuit. In some instances, the circuit may be configured such that binding of a BTTS to its antigen induces expression of a therapeutic which binds a bio-orthogonal adapter molecule. In some instances, the BTTS that induces expression of the therapeutic is the same BTTS that induces expression of the bio-orthogonal adapter molecule. In some instance, the therapeutic is induced by a BTTS that is different (i.e., separate) from the BTTS that induces expression of the bio-orthogonal adapter molecule.

In some instances, expression of a therapeutic which binds a bio-orthogonal adapter molecule may not be induced by a BTTS. For example, in some instances, rather than being induced by a BTTS, such a therapeutic is expressed under the control of a separate regulatory element or sequence, including but not limited to e.g., where the expression of the therapeutic is constitutive, inducible, conditional, tissue specific, cell type specific, or the like. In some instances, for example, independent expression (e.g., constitutive expression, inducible expression, etc.) of the therapeutic by introduced immune cells allows for a diffusible bio-orthogonal adapter molecule to mediate the activation of the therapeutic in immune cells that are distant from the site of priming.

In some instances, expression of a bio-orthogonal adapter molecule, bound by a therapeutic, may not be induced by a BTTS, including where the corresponding therapeutic is induced by a BTTS. For example, in some instances, rather than being induced by a BTTS, such a bio-orthogonal adapter molecule is expressed under the control of a separate regulatory element or sequence, including but not limited to e.g., where the expression of the bio-orthogonal adapter molecule is constitutive, inducible, conditional, tissue specific, cell type specific, or the like. In some instances, the bio-orthogonal adapter molecule may be externally provided.

In some instances, an antigen-specific therapeutic may have an extracellular domain that includes a first member of a specific binding pair that binds a second member of the specific binding pair, wherein the extracellular domain does not include any additional first or second member of a second specific binding pair. For example, in some instances, an antigen-specific therapeutic may have an extracellular domain that includes a first antigen-binding domain that binds an antigen, wherein the extracellular domain does not include any additional antigen-binding domains and does not bind any other antigens. A subject antigen-specific therapeutic may, in some instances, include only a single extracellular domain. Accordingly, an employed antigen-specific therapeutic may be specific for a single antigen and only specific for the single antigen. Such, antigen-specific therapeutics may be referred to as a "single antigen antigen-specific therapeutic".

In some instances, an antigen-specific therapeutic may have an extracellular domain that includes the first or second members of two or more specific binding pairs. For example, in some instances, an antigen-specific therapeutic may have an extracellular domain that includes a first antigen-binding domain and a second antigen-binding domain that are different such that the extracellular domain is specific for two different antigens. In some instances, an antigen-specific therapeutic may have two or more extracellular domains that each includes the first or second members of two different specific binding pairs. For example, in some instances, an antigen-specific therapeutic may have a first extracellular domain that includes a first antigen-binding domain and a second extracellular domain that includes a second antigen-binding domain where the two different antigen binding domains are each specific for a different antigen. As such, the antigen-specific therapeutic may be specific for two different antigens.

An antigen-specific therapeutic specific for two or more different antigens, containing either two extracellular domains or one extracellular domain specific for two different antigens, may be configured such that the binding of either antigen to the antigen-specific therapeutic is sufficient to active the antigen-specific therapeutic. Such an antigen-specific therapeutic, capable of being activated by any of two or more antigens, may find use in the described circuits as a component of a logic gate containing OR functionality. In some instances, an antigen-specific therapeutic specific for two different antigens may be referred to as a "two-headed antigen-specific therapeutic". Antigen-specific therapeutics specific for multiple antigens will not be limited to only two antigens and may, e.g., be specific for and/or activated by more than two antigens, including e.g., three or more, four or more, five or more, etc.

For example, in some instances, an antigen-specific therapeutic specific for two or more different antigens may bind, and/or be activated by, EphA2 or EphA3, EphA2 or IL13RA1, EphA2 or IL13RA2, EphA2 or EGFR, EphA2 or ERBB2, EphA3 or IL13RA1, EphA3 or IL13RA2, EphA3 or EGFR, EphA3 or ERBB2, IL13RA1 or IL13RA2, IL13RA1 or EGFR, IL13RA1 or ERBB2, IL13RA2 or EGFR, IL13RA2 or ERBB2, or EGFR or ERBB2.

An example of an antigen-specific therapeutic specific for two or more different antigens is a tandem CAR (also referred to as "tan CAR" or "tanCAR"). A "tandem CAR" is a bispecific CAR that includes two or more non-identical antigen recognition domains. Non-limiting examples of tandem CARs include those described in U.S. Pat. Nos. 9,447,194; 10,155,038; 10,189,903; and 10,239,948; U.S. Patent Application Pub. No. 20130280220 and PCT Application Pub. No. WO/2013/123061; the disclosures of which are incorporated herein by reference in their entirety. Tandem CARs may be configured to bind a variety of different antigens, including but not limited to e.g., two or more or the antigens described herein and/or two or more of the antigens described in U.S. Pat. Nos. 9,447,194; 10,155,038; 10,189,903; and 10,239,948; U.S. Patent Application Pub. No. 20130280220 and PCT Application Pub. No. WO/2013/123061.

Binding Triggered Transcriptional Switches (BTTS)

The methods of the instant disclosure include the use of circuits employing a BTTS to induce expression of an encoded antigen-specific therapeutic. As used herein, a "binding-triggered transcriptional switch" or BTTS generally refers to a synthetic modular polypeptide or system of interacting polypeptides having an extracellular domain that includes a first member of a specific binding pair, a binding-transducer and an intracellular domain. Upon binding of the second member of the specific binding pair to the BTTS the binding signal is transduced to the intracellular domain such that the intracellular domain becomes activated and performs some function within the cell that it does not perform in the absence of the binding signal. Binding triggered transcriptional switches are described in e.g., PCT Pub. No. WO 2016/138034 as well as U.S. Pat. Nos. 9,670,281 and 9,834,608; the disclosures of which are incorporated herein by reference in their entirety.

The specific binding member of the extracellular domain generally determines the specificity of the BTTS. In some instances, a BTTS may be referred according to its specificity as determined based on its specific binding member. For example, a specific binding member having binding partner "X" may be referred to as an X-BTTS or an anti-X BTTS.

Any convenient specific binding pair, i.e., specific binding member and specific binding partner pair, may find use in the BTTS of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a scaffold protein and its binding partner may be a protein to which the scaffold protein specifically binds. Useful specific binding pairs include those specific for EGFRvIII priming antigen and/or one or more targeting/killing antigens, including those described herein.

In some cases, the specific binding member is an antibody. The antibody can be any antigen-binding antibody-based polypeptide, a wide variety of which are known in the art. In some instances, the specific binding member is or includes a monoclonal antibody, a single chain Fv (scFv), a Fab, etc. Other antibody based recognition domains (cAb $V_{HH}$ (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VaVβ) are also suitable for use.

Where the specific binding member of a BTTS is an antibody-based binding member, the BTTS can be activated in the presence of a binding partner to the antibody-based binding member, including e.g., an antigen specifically bound by the antibody-based binding member. In some instances, antibody-based binding member may be defined, as is commonly done in the relevant art, based on the antigen bound by the antibody-based binding member, including e.g., where the antibody-based binding member is described as an "anti-" antigen antibody, e.g., an anti-EGFRvIII antibody. Accordingly, antibody-based binding members suitable for inclusion in a BTTS or an antigen-specific therapeutic of the present methods can have a variety of antigen-binding specificities.

The components of BTTS's, employed in the described methods, and the arrangement of the components of the switch relative to one another will vary depending on many factors including but not limited to e.g., the desired binding trigger, the activity of the intracellular domain, the overall function of the BTTS, the broader arrangement of a molecular circuit comprising the BTTS, etc. The first binding member may include but is not limited to e.g., those agents that bind an antigen described herein. The intracellular domain may include but is not limited e.g., those intracellular domains that activate or repress transcription at a regulatory sequence, e.g., to induce or inhibit expression of a downstream component of a particular circuit.

The binding transducer of BTTS's will also vary depending on the desired method of transduction of the binding signal. Generally, binding transducers may include those polypeptides and/or domains of polypeptides that transduce an extracellular signal to intracellular signaling e.g., as performed by the receptors of various signal transduction pathways. Transduction of a binding signal may be achieved through various mechanisms including but not limited to e.g., binding-induced proteolytic cleavage, binding-induced phosphorylation, binding-induced conformational change, etc. In some instances, a binding-transducer may contain a ligand-inducible proteolytic cleavage site such that upon binding the binding-signal is transduced by cleavage of the BTTS, e.g., to liberate an intracellular domain. For example, in some instances, a BTTS may include a Notch derived cleavable binding transducer, such as, e.g., a chimeric notch receptor polypeptide as described herein.

In other instances, the binding signal may be transduced in the absence of inducible proteolytic cleavage. Any signal transduction component or components of a signaling transduction pathway may find use in a BTTS whether or not proteolytic cleavage is necessary for signal propagation. For example, in some instances, a phosphorylation-based binding transducer, including but not limited to e.g., one or more signal transduction components of the Jak-Stat pathway, may find use in a non-proteolytic BTTS.

For simplicity, BTTS's, including but not limited to chimeric notch receptor polypeptides, are described primarily as single polypeptide chains. However, BTTS's, including chimeric notch receptor polypeptides, may be divided or split across two or more separate polypeptide chains where the joining of the two or more polypeptide chains to form a functional BTTS, e.g., a chimeric notch receptor polypeptide, may be constitutive or conditionally controlled. For example, constitutive joining of two portions of a split BTTS may be achieved by inserting a constitutive heterodimerization domain between the first and second portions of the split polypeptide such that upon heterodimerization the split portions are functionally joined.

Useful BTTS's that may be employed in the subject methods include, but are not limited to modular extracellular sensor architecture (MESA) polypeptides. A MESA polypeptide comprises: a) a ligand binding domain; b) a transmembrane domain; c) a protease cleavage site; and d) a functional domain. The functional domain can be a transcription regulator (e.g., a transcription activator, a transcription repressor). In some cases, a MESA receptor comprises two polypeptide chains. In some cases, a MESA receptor comprises a single polypeptide chain. Non-limiting examples of MESA polypeptides are described in, e.g., U.S. Patent Publication No. 2014/0234851; the disclosure of which is incorporated herein by reference in its entirety.

Useful BTTS's that may be employed in the subject methods include, but are not limited to polypeptides employed in the TANGO assay. The subject TANGO assay employs a TANGO polypeptide that is a heterodimer in which a first polypeptide comprises a tobacco etch virus (Tev) protease and a second polypeptide comprises a Tev proteolytic cleavage site (PCS) fused to a transcription factor. When the two polypeptides are in proximity to one another, which proximity is mediated by a native protein-protein interaction, Tev cleaves the PCS to release the transcription factor. Non-limiting examples of TANGO polypeptides are described in, e.g., Barnea et al. (Proc Natl Acad Sci USA. 2008 Jan. 8; 105(1):64-9); the disclosure of which is incorporated herein by reference in its entirety.

Useful BTTS's that may be employed in the subject methods include, but are not limited to von Willebrand Factor (vWF) cleavage domain-based BTTS's, such as but not limited to e.g., those containing a unmodified or modified vWF A2 domain. A subject vWF cleavage domain-based BTTS will generally include: an extracellular domain comprising a first member of a binding pair; a von Willebrand Factor (vWF) cleavage domain comprising a proteolytic cleavage site; a cleavable transmembrane domain and an intracellular domain. Non-limiting examples of vWF cleavage domains and vWF cleavage domain-based BTTS's are described in Langridge & Struhl (Cell (2017) 171(6): 1383-1396); the disclosure of which is incorporated herein by reference in its entirety.

Useful BTTS's that may be employed in the subject methods include, but are not limited to chimeric Notch receptor polypeptides, such as but not limited to e.g., synNotch polypeptides, non-limiting examples of which are described in PCT Pub. No. WO 2016/138034, U.S. Pat. Nos. 9,670,281, 9,834,608, Roybal et al. Cell (2016) 167(2):419-432, Roybal et al. Cell (2016) 164(4):770-9, and Morsut et al. Cell (2016) 164(4):780-91; the disclosures of which are incorporated herein by reference in their entirety.

SynNotch polypeptides are generally proteolytically cleavable chimeric polypeptides that generally include: a) an extracellular domain comprising a specific binding member; b) a proteolytically cleavable Notch receptor polypeptide comprising one or more proteolytic cleavage sites; and c) an intracellular domain. Binding of the specific binding member by its binding partner generally induces cleavage of the synNotch at the one or more proteolytic cleavage sites, thereby releasing the intracellular domain. In some instances, the instant methods may include where release of the intracellular domain triggers (i.e., induces) the production of an encoded payload, the encoding nucleic acid sequence of which is contained within the cell. Depending on the particular context, the produced payload is then generally expressed on the cell surface or secreted. SynNotch polypeptides generally include at least one sequence that is heterologous to the Notch receptor polypeptide (i.e., is not derived from a Notch receptor), including e.g., where the extracellular domain is heterologous, where the intracellular domain is heterologous, where both the extracellular domain and the intracellular domain are heterologous to the Notch receptor, etc.

Useful synNotch BTTS's will vary in the domains employed and the architecture of such domains. SynNotch polypeptides will generally include a Notch receptor polypeptide that includes one or more ligand-inducible proteolytic cleavage sites. The length of Notch receptor polypeptides will vary and may range in length from about 50 amino acids or less to about 1000 amino acids or more.

In some cases, the Notch receptor polypeptide present in a synNotch polypeptide has a length of from 50 amino acids (aa) to 1000 aa, e.g., from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, from 750 aa to 800 aa, from 800 aa to 850 aa, from 850 aa to 900 aa, from 900 aa to 950 aa, or from 950 aa to 1000 aa. In some cases, the Notch receptor polypeptide present in a synNotch polypeptide has a length of from 300 aa to 400 aa, from 300 aa to 350 aa, from 300 aa to 325 aa, from 350 aa to 400 aa, from 750 aa to 850 aa, from 50 aa to 75 aa. In some cases, the Notch receptor polypeptide has a length of from 310 aa to 320 aa, e.g., 310 aa, 311 aa, 312 aa, 313 aa, 314 aa, 315 aa, 316 aa, 317 aa, 318 aa, 319 aa, or 320 aa. In some cases, the Notch receptor polypeptide has a length of 315 aa. In some cases, the Notch receptor polypeptide has a length of from 360 aa to 370 aa, e.g., 360 aa, 361 aa, 362 aa, 363 aa 364 aa, 365 aa, 366 aa, 367 aa, 368 aa, 369 aa, or 370 aa. In some cases, the Notch receptor polypeptide has a length of 367 aa.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Subject Notch regulatory regions may include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an S1 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta-binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

Non-limiting examples of particular synNotch BTTS's, the domains thereof, and suitable domain arrangements are described in PCT Pub. Nos. WO 2016/138034, WO 2017/193059, WO 2018/039247 and U.S. Pat. Nos. 9,670,281 and 9,834,608; the disclosures of which are incorporated herein by reference in their entirety.

Domains of a useful BTTS, e.g., the extracellular domain, the binding-transducer domain, the intracellular domain, etc., may be joined directly, i.e., with no intervening amino acid residues or may include a peptide linker that joins two domains. Peptide linkers may be synthetic or naturally derived including e.g., a fragment of a naturally occurring polypeptide.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa. A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

In some instances, a BTTS may have an extracellular domain that includes a first member of a specific binding pair that binds a second member of the specific binding pair, wherein the extracellular domain does not include any additional first or second member of a second specific binding pair. For example, in some instances, a BTTS may have an extracellular domain that includes a first antigen-binding domain that binds an antigen, wherein the extracellular domain does not include any additional antigen-binding domains and does not bind any other antigens. A subject BTTS may, in some instances, include only a single extracellular domain. Accordingly, an employed BTTS may be specific for a single antigen and only specific for the single antigen. Such, BTTS's may be referred to as a "single antigen BTTS".

In some instances, a BTTS may have an extracellular domain that includes the first or second members of two or more specific binding pairs. For example, in some instances, a BTTS may have an extracellular domain that includes a first antigen-binding domain and a second antigen-binding domain that are different such that the extracellular domain is specific for two different antigens. In some instances, a BTTS may have two or more extracellular domains that each includes the first or second members of two different specific binding pairs. For example, in some instances, a BTTS may have a first extracellular domain that includes a first antigen-binding domain and a second extracellular domain that includes a second antigen-binding domain where the two different antigen binding domains are each specific for a different antigen. As such, the BTTS may be specific for two different antigens.

A BTTS specific for two or more different antigens, containing either two extracellular domains or one extracellular domain specific for two different antigens, may be configured such that the binding of either antigen to the BTTS is sufficient to trigger activation of the BTTS, e.g., proteolytic cleavage of a cleavage domain of the BTTS, e.g., releasing an intracellular domain of the BTTS. Such a BTTS, capable of being triggered by any of two or more antigens, may find use in the described circuits as a component of a logic gate containing OR functionality. In some instances, a BTTS specific for two different antigens may be referred to as a "two-headed BTTS" or a tandem BTTS (or tanBTTS). For example, in some instances, a synNotch BTTS configured to bind two or more different antigens may be referred to as a tandem SynNotch or tanSynNotch. BTTS specific for multiple antigens will not be limited to only two antigens and may, e.g., be specific for and/or triggered by more than two antigens, including e.g., three or more, four or more, five or more, etc.

Methods of Making

The present disclosure further includes methods of making the nucleic acids, circuits, and cells employed in the herein described methods. In making the subject nucleic acids and circuits, and components thereof, any convenient methods of nucleic acid manipulation, modification and amplification (e.g., collectively referred to as "cloning") may be employed. In making the subject cells, containing the nucleic acids encoding the described circuits, convenient methods of transfection, transduction, culture, etc., may be employed.

A nucleotide sequence encoding all or a portion of the components of a circuit of the present disclosure can be present in an expression vector and/or a cloning vector. Where a subject circuit or component thereof is split between two or more separate polypeptides, nucleotide sequences encoding the two or more polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding a circuit or component thereof of the present disclosure will in some embodiments be DNA or RNA, e.g., in vitro synthesized DNA, recombinant DNA, in vitro synthesized RNA, recombinant RNA, etc. Methods for in vitro synthesis of DNA/RNA are known in the art; any known method can be used to synthesize DNA/RNA comprising a desired sequence. Methods for introducing DNA/RNA into a host cell are known in the art. Introducing DNA/RNA into a host cell can be carried out in vitro or ex vivo or in vivo. For example, a host cell (e.g., an NK cell, a cytotoxic T lymphocyte, etc.) can be transduced, transfected or electroporated in vitro or ex vivo with DNA/RNA comprising a nucleotide sequence encoding all or a portion of a circuit of the present disclosure.

Methods of the instant disclosure may further include culturing a cell genetically modified to encode a circuit of the instant disclosure including but not limited to e.g., culturing the cell prior to administration, culturing the cell in vitro or ex vivo (e.g., the presence or absence of one or more antigens), etc. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS, microfluidics, etc.), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Nucleic Acids

As summarized above, the present disclosure provides nucleic acids encoding a circuit for treating a subject for a heterogeneous EGFRvIII(+) GBM and components thereof. The subject nucleic acids may include, e.g., a sequence encoding a BTTS specific for EGFRvIII and a sequence encoding a targeting antigen-specific therapeutic, including e.g., a targeting antigen-specific therapeutic specific for one or more of EphA2, EphA3, IL13RA2 (or IL13RA1), EGFR and/or ERBB2. Such nucleic acids may be configured such that the sequence encoding the targeting antigen-specific therapeutic is operably linked to a regulatory sequence responsive to activation of the BTTS. Provided are nucleic acids encoding essentially any circuit employing trans-targeting utilizing recognition of an EGFRvIII priming antigen expressed on a first GBM cell to target a second GBM cell expressing a targeting antigen, including but not limited to those circuits specifically described herein. Encompassed are isolated nucleic acids encoding the subject circuits as well as various configurations containing such nucleic acids, such as vectors, e.g., expression cassettes, recombinant expression vectors, viral vectors, and the like.

Recombinant expression vectors of the present disclosure include those comprising one or more of the described nucleic acids. A nucleic acid comprising a nucleotide sequence encoding all or a portion of the components of a circuit of the present disclosure will in some embodiments be DNA, including, e.g., a recombinant expression vector. A nucleic acid comprising a nucleotide sequence encoding all or a portion of the components of a circuit of the present disclosure will in some embodiments be RNA, e.g., in vitro synthesized RNA.

As summarized above, in some instances, the subject circuits may make use of an encoding nucleic acid (e.g., a nucleic acid encoding a BTTS or an antigen-specific therapeutic) that is operably linked to a regulatory sequence such as a transcriptional control element (e.g., a promoter; an enhancer; etc.). In some cases, the transcriptional control element is inducible. In some cases, the transcriptional control element is constitutive. In some cases, the promoters are functional in eukaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is an immune cell promoter such as a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90: 7739; and Marodon et al. (2003) *Blood* 101:3416. As another example, a CD8 gene promoter can be used. NK cell-specific expression can be achieved by use of an *Ncr*1 (p46) promoter; see, e.g., Eckelhart et al. (2011) *Blood* 117:1565.

In some instances, an immune cell specific promoter of a nucleic acid of the present disclosure may be a promoter of a B29 gene promoter, a CD14 gene promoter, a CD43 gene promoter, a CD45 gene promoter, a CD68 gene promoter, a IFN-β gene promoter, a WASP gene promoter, a T-cell receptor β-chain gene promoter, a V9γ (TRGV9) gene promoter, a V2δ (TRDV2) gene promoter, and the like.

In some cases, a nucleic acid comprising a nucleotide sequence encoding a circuit of the present disclosure, or one or more components thereof, is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a circuit of the present disclosure, or one or more components thereof, is a recombinant lentivirus vector. In some cases, a nucleic acid comprising a nucleotide sequence encoding a circuit of the present disclosure, or one or more components thereof, is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some instances, nucleic acids of the present disclosure may have a single sequence encoding two or more polypeptides where expression of the two or more polypeptides is made possible by the presence of a sequence element between the individual coding regions that facilitates separate expression of the individual polypeptides. Such sequence elements, may be referred to herein as bicistronic-facilitating sequences, where the presence of a bicistronic-facilitating sequence between two coding regions makes possible the expression of a separate polypeptide from each coding region present in a single nucleic acid sequence. In some instances, a nucleic acid may contain two coding regions encoding two polypeptides present in a single nucleic acid with a bicistronic-facilitating sequence between the coding regions. Any suitable method for separate expression of multiple individual polypeptides from a single nucleic acid sequence may be employed and, similarly, any suitable method of bicistronic expression may be employed.

In some instances, a bicistronic-facilitating sequence may allow for the expression of two polypeptides from a single nucleic acid sequence that are temporarily joined by a cleavable linking polypeptide. In such instances, a bicistronic-facilitating sequence may include one or more encoded peptide cleavage sites. Suitable peptide cleavage sites include those of self-cleaving peptides as well as those cleaved by a separate enzyme. In some instances, a peptide cleavage site of a bicistronic-facilitating sequence may include a furin cleavage site (i.e., the bicistronic-facilitating sequence may encode a furin cleavage site).

In some instances, the bicistronic-facilitating sequence may encode a self-cleaving peptide sequence. Useful self-cleaving peptide sequences include but are not limited to e.g., peptide 2A sequences, including but not limited to e.g., the T2A sequence.

In some instances, a bicistronic-facilitating sequence may include one or more spacer encoding sequences. Spacer encoding sequences generally encode an amino acid spacer, also referred to in some instances as a peptide tag. Useful spacer encoding sequences include but are not limited to e.g., V5 peptide encoding sequences, including those sequences encoding a V5 peptide tag.

Multi- or bicistronic expression of multiple coding sequences from a single nucleic acid sequence may make use of but is not limited to those methods employing furin cleavage, T2A, and V5 peptide tag sequences. For example, in some instances, an internal ribosome entry site (IRES) based system may be employed. Any suitable method of bicistronic expression may be employed including but not limited to e.g., those described in Yang et al. (2008) Gene Therapy. 15(21):1411-1423; Martin et al. (2006) BMC Biotechnology. 6:4; the disclosures of which are incorporated herein by reference in their entirety.

Cells

As summarized above, the present disclosure also provides immune cells. Immune cells of the present disclosure include those that contain one or more of the described nucleic acids, expression vectors, etc., encoding a described circuit. Immune cells of the present disclosure include mammalian immune cells including e.g., those that are genetically modified to produce the components of a circuit of the present disclosure or to which a nucleic acid, as described above, has been otherwise introduced. In some instances, the subject immune cells have been transduced with one or more nucleic acids and/or expression vectors to express one or more components of a circuit of the present disclosure.

Suitable mammalian immune cells include primary cells and immortalized cell lines. Suitable mammalian cell lines include human cell lines, non-human primate cell lines, rodent (e.g., mouse, rat) cell lines, and the like. In some instances, the cell is not an immortalized cell line, but is instead a cell (e.g., a primary cell) obtained from an individual. For example, in some cases, the cell is an immune cell, immune cell progenitor or immune stem cell obtained from an individual. As an example, the cell is a lymphoid cell, e.g., a lymphocyte, or progenitor thereof, obtained from an individual. As another example, the cell is a cytotoxic cell, or progenitor thereof, obtained from an individual. As another example, the cell is a stem cell or progenitor cell obtained from an individual.

As used herein, the term "immune cells" generally includes white blood cells (leukocytes) which are derived from hematopoietic stem cells (HSC) produced in the bone marrow. "Immune cells" includes, e.g., lymphoid cells, i.e., lymphocytes (T cells, B cells, natural killer (NK) cells), and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses. "B cell" includes mature and immature cells of the B cell lineage including e.g., cells that express CD19 such as Pre B cells, Immature B cells, Mature B cells, Memory B cells and plasmablasts. Immune cells also include B cell progenitors such as Pro B cells and B cell lineage derivatives such as plasma cells.

Immune cells encoding a circuit of the present disclosure may be generated by any convenient method. Nucleic acids encoding one or more components of a subject circuit may be stably or transiently introduced into the subject immune cell, including where the subject nucleic acids are present only temporarily, maintained extrachromosomally, or integrated into the host genome. Introduction of the subject nucleic acids and/or genetic modification of the subject immune cell can be carried out in vivo, in vitro, or ex vivo.

In some cases, the introduction of the subject nucleic acids and/or genetic modification is carried out ex vivo. For example, a T lymphocyte, a stem cell, or an NK cell is obtained from an individual; and the cell obtained from the individual is modified to express components of a circuit of the present disclosure. The modified cell can thus be redirected to one or more antigens of choice, as defined by the one or more antigen binding domains present on the introduced components of the circuit. In some cases, the modified cell is modulated ex vivo. In other cases, the cell is introduced into (e.g., the individual from whom the cell was obtained) and/or already present in an individual; and the cell is modulated in vivo, e.g., by administering a nucleic acid or vector to the individual in vivo.

Circuits

As summarized above, the present disclosure also provides circuits encoded by nucleic acid sequences, also referred to in some instances as molecular circuits. Such circuits may, in some instances, be present and/or configured in expression vectors and/or expression cassettes. The subject nucleic acids of the present circuits may, in some instances, be contained within a vector, including e.g., viral and non-viral vectors. Such circuits may, in some instances, be present in cells, such as immune cells, or may be introduced into cells by various means, including e.g., through the use of a viral vector. Cells may, in some instances, be genetically modified to encode a subject circuit, where such modification may be effectively permanent (e.g., integrated) or transient as desired.

Encoded components of the circuits of the present disclosure will generally include at a minimum at least one encoded BTTS and at least one encoded antigen-specific therapeutic. Circuits of the present disclosure integrate multiple inputs, where such inputs include antigens, such as EGFRvIII priming antigen, one or more targeting antigens (e.g., EphA2, EphA3, IL13RA2 (or IL13RA1), EGFR, ERBB2 and/or combinations thereof) and the like. The expression of a component of a circuit of the present disclosure may be dependent upon the state (i.e., active/inactive state) of another component of the circuit. For example, the expression of an antigen-specific therapeutic may be dependent upon the activation of a BTTS, where the BTTS is activated by binding to an antigen for which the BTTS is specific (e.g., EGFRvIII). In some instances, dependency of one component of the circuit on another may be mediated by a regulatory sequence. For example, a sequence encoding a second component of a circuit may be operably linked to a regulatory sequence that is responsive to the activation of a first component of the circuit, thus linking the expression of the second component to the activation of the first.

The use of a BTTS in a circuit of the present disclosure facilitates the linking of expression and/or activity to molecular binding events. Systems involving binding-triggered transcriptional switches, and components thereof, have been described in PCT Publication No. WO 2016/138034, US Patent Application Pub. No. US 2016-0264665 A1 and issued U.S. Pat. Nos. 9,670,281 and 9,834,608; the disclosures of which are incorporated by reference herein in their entirety.

Circuits of the present disclosure may be configured in various ways. In some instances, the independent activities and/or induced expression of two or more polypeptides or domains of a single polypeptide may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates). In some instances, useful circuits may further include IF/THEN gates.

"AND" gates include where two or more inputs are required for propagation of a signal. For example, in some instances, an AND gate allows signaling through a first input of a first polypeptide or a first polypeptide domain and a second input dependent upon the output of the first input. In an AND gate two inputs, e.g., two antigens, are required for signaling through the circuit.

"OR" gates include where either of two or more inputs may allow for the propagation of a signal. For example, in some instances, an OR gate allows signaling through binding of either of two different antigens. In an OR gate any one input, e.g., either of two antigens, may induce the signaling output of the circuit. In one embodiment, an OR gate may be achieved through the use of two separate molecules or constructs. In another embodiment, an OR gate may be achieved through the use of a single construct that recognizes two antigens, including e.g., a BTTS or an antigen-specific therapeutic (e.g., a CAR or TCR) having two different antigen binding domains that each bind a different antigen and each binding event can independently propagate the signal (e.g., induce expression of a downstream component of the circuit, activate an immune cell, etc.).

"NOT" gates include where an input is capable of preventing the propagation of a signal.

For example, in some instances, a NOT gate inhibits signaling through a circuit of the instant disclosure. In one embodiment, a NOT gate may prevent the expression of a component of a circuit, or activation of a particular component of the circuit, e.g., a CAR or a TCR.

"IF/THEN" gates include where the output of the gate depends upon a first input. For example, in some instances, IF a first input is present THEN signaling may proceed through a second input, and where the first input is absent signaling may not proceed. A non-limiting example of a circuit that includes an IF/THEN gate is a circuit having at least two receptors where the first receptor, in response to an input, induces expression of the second receptor, which has some output in response to a second input. As such, IF the first input of the first receptor is present, THEN the second receptor is expressed and signaling can proceed through the second receptor via the second input to produce the output. IF/THEN gates may or may not include an OR component (e.g., a receptor with OR functionality).

Non-limiting examples of IF/THEN gates, including examples with OR functionality, are depicted in FIG. 16. The circuit depicted in the first (top) cell of FIG. 16 includes a BTTS responsive to antigen "A" and an antigen-specific therapeutic that binds antigen "C". Note that although the antigen-specific therapeutic is depicted as a CAR, the disclosure is not so limited and other antigen-specific therapeutics may be readily substituted. In the first (top) circuit, IF antigen A is present THEN cell killing is induced based on the presence of antigen C.

In various embodiments, OR functionality may be employed, including where one or more components of a subject circuit include an OR functionality. As shown in the second, third and fourth cells depicted in FIG. 16, OR functionality may be provided by a BTTS, an antigen-specific therapeutic, or both having specificity for, and being triggered or activated by, two or more antigens.

For example, in the second (from the top) cell depicted in FIG. 16, a circuit is employed that includes a BTTS responsive to antigen "A" and an antigen-specific therapeutic that binds to, and is activated by, antigen "C" or antigen "D". In such a circuit, IF antigen A is present THEN cell killing is induced based on the presence of antigen C OR antigen D. Note that killing of cells expressing antigen C and antigen D may also be induced, as well as killing of cells that express antigen C alone or antigen D alone.

In the third (from the top) cell depicted in FIG. 16, a circuit is employed that includes a BTTS responsive to antigen "A" or antigen "B" and an antigen-specific therapeutic that binds to, and is activated by, antigen "C". In such a circuit, IF antigen A OR antigen B is present THEN cell killing is induced based on the presence of antigen C. Note that the immune cells encoding the subject circuit may be primed to kill by a cell expressing only antigen A, only antigen B, or both antigens A and B.

In the fourth (bottom) cell depicted in FIG. 16, a circuit is employed that includes a BTTS responsive to antigen "A" or antigen "B" and an antigen-specific therapeutic that binds to, and is activated by, antigen "C" or antigen "D". In such a circuit, IF antigen A OR antigen B is present THEN cell killing is induced based on the presence of antigen C or antigen D. Note that the immune cells encoding the subject circuit may be primed to kill by a cell expressing only antigen A, only antigen B, or both antigens A and B. Also note that killing of cells expressing antigen C and antigen D may also be induced, as well as killing of cells that express antigen C alone or antigen D alone.

In some instances, the use of OR functionality may have certain advantages. For example, the above described circuits having OR gate functionality (i.e., the second, third and fourth cells of FIG. 16) and variations thereof provide resistance to escape and improved efficacy for heterogeneous cancers because, without being bound by theory, to escape a cancer (or tumor) would need to contain, or evolve/produce, a cell that does not express either of the two priming and/or killing antigens.

In some instances, multiple antigen binding domains present on a BTTS or antigen-specific therapeutic may provide an OR gate capability to the herein described molecular circuits. For example, in some instances, a BTTS having two different antigen binding domains may be responsive to a first antigen (e.g., a first priming antigen) OR a second antigen (e.g., a second priming antigen). In some instances, an antigen-specific therapeutic (e.g., a CAR, a TCR, etc.) having two different antigen binding domains may be responsive to a first antigen (e.g., a first targeting antigen) OR a second antigen (e.g., a second targeting antigen).

In some instances, such OR gates may be combined with other gates, including an AND gate. For example, a nucleic acid encoding an OR-gate antigen-specific therapeutic having two different antigen binding domains may be operably linked to a promoter that is responsive to a BTTS which is responsive to a first antigen (e.g., EGFRvIII). As such, upon binding the first antigen (e.g., EGFRvIII), the BTTS drives expression of the antigen-specific therapeutic which is responsive to two different antigens, resulting in an AND-OR gate.

In some instances, OR gates may find use in the circuits of the present disclosure to produce an OR gate for two or more targeting antigens (or two or more killing antigens). For example, in some instances, the circuit may be configured such that the cell genetically modified with the circuit contains a nucleic acid sequence encoding an antigen-specific therapeutic that binds to a first targeting/killing antigen or a second targeting/killing antigen expressed by a targeted cancer cell (or expressed by two different targeted cancer cells), thereby producing a cell that is activated, e.g., activated for cell killing, by either the first targeting/killing antigen or the second targeting/killing antigen. In some instances, a circuit of the present disclosure may include nucleic acid sequence encoding a first antigen-specific therapeutic and second antigen-specific therapeutic that each bind to a different targeting/killing antigen. Useful antigens in such dual antigen-specific therapeutic OR gates include but are not limited to e.g., EphA2, EphA3, IL13RA2 (or IL13RA1), EGFR and ERBB2.

In some instances, an OR gate may be employed to allow for simultaneous targeting of cells both in trans and in cis. For example, in some instances, a second killing antigen to which an OR gate is directed may be expressed by the priming cell. In some instances, an OR gate for targeting may be employed to target two antigens that that are not mutually exclusively expressed within cells of the GBM (i.e., GBM cells with overlapping, but not completely coincident, expression of two antigens). For example, in some instances, the second killing antigen to which an OR gate is targeted may be expressed by a subpopulation of GBM cells that also expresses the first killing antigen. However, the cancer may further include a subpopulation of cells that express the second killing antigen but not the first killing antigen. In some instances, the first and second killing antigens employed in an OR gate will not have overlapping expression in the cells of the heterogeneous cancer. As such, in some instances, the second killing antigen may be expressed by a cell of the heterogeneous GBM other than the priming cell and/or the GBM cell that expresses the first killing antigen.

Kits

The present disclosure provides a kit for carrying out a method as described herein and/or constructing one or more circuits, components thereof, nucleic acids encoding a circuit or a component thereof, etc. In some cases, a subject kit comprises a vector, e.g., an expression vector or a delivery vector, comprising a nucleotide sequence encoding a circuit of the present disclosure or one or more portions thereof. Delivery vectors may be provided in a delivery device or may be provided separately, e.g., as a kit that includes the delivery vector and the delivery device as separate components of the kit.

In some cases, a subject kit comprises a cell, e.g., a host cell or host cell line, that is or is to be genetically modified with a nucleic acid comprising nucleotide sequence encoding a circuit of the present disclosure or a portion thereof. In some cases, a subject kit comprises a cell, e.g., a host cell, that is or is to be genetically modified with a recombinant expression vector comprising a nucleotide sequence encoding a circuit of the present disclosure. Kit components can be in the same container, or in separate containers.

Any of the above-described kits can further include one or more additional reagents, where such additional reagents can be selected from: a dilution buffer; a reconstitution solution; a wash buffer; a control reagent; a control expression vector; a nucleic acid encoding a negative control (e.g., a circuit that lacks the one or more critical elements); a nucleic acid encoding a positive control polypeptide; and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of treating a subject for an epidermal growth factor receptor variant III (EGFRvIII) positive glioblastoma, the method comprising: administering to the subject an immune cell genetically modified with:
    (a) a nucleic acid sequence encoding a binding triggered transcriptional switch (BTTS) that binds to EGFRvIII;
    (b) a nucleic acid sequence encoding an antigen-specific therapeutic that binds to a killing antigen expressed by the glioblastoma; and
    (c) a regulatory sequence operably linked to (b) that is responsive to the BTTS;

wherein binding of the BTTS to EGFRvIII activates expression of the antigen-specific therapeutic which binds the killing antigen thereby inducing killing of glioblastoma cells expressing the killing antigen.

2. The method according to aspect 1, wherein the EGFRvIII positive glioblastoma comprises cells that express either EGFRvIII or the killing antigen.

3. The method according to aspect 1 or aspect 2, wherein the glioblastoma comprises cells that express both EGFRvIII and the killing antigen.

4. The method according to aspect 1, wherein the killing antigen is expressed by all cells of the glioblastoma.

5. The method according to any of the preceding aspects, wherein the killing antigen is expressed by non-glioblastoma cells in the subject.

6. The method according to any of the preceding aspects, wherein less than 95% of the glioblastoma cells express EGFRvIII.

7. The method according to any of the preceding aspects, wherein the killing antigen is selected from the group consisting of: Ephrin type-A receptor 2 (EphA2), Ephrin type-A receptor 3 (EphA3), Interleukin-13 receptor subunit alpha-1 (IL13RA1), Interleukin-13 receptor subunit alpha-2 (IL13RA2), Epidermal growth factor receptor (EGFR) and erb-b2 receptor tyrosine kinase 2 (ERBB2).

8. The method according to any of the preceding aspects, wherein the antigen-specific therapeutic, when expressed, is expressed on the surface of the immune cell.

9. The method according to aspect 8, wherein the antigen-specific therapeutic is a chimeric antigen receptor (CAR) or a T cell receptor (TCR).

10. The method according to any of aspects 1 to 7, wherein the antigen-specific therapeutic, when expressed, is secreted by the immune cell.

11. The method according to aspect 10, wherein the antigen-specific therapeutic is a chimeric bispecific binding member.

12. The method according to aspect 11, wherein the chimeric bispecific binding member is a TCR-targeted bispecific binding agent.

13. The method according to aspect 11 or aspect 12, wherein the chimeric bispecific binding member is specific for the killing antigen and a protein expressed on the surface of an immune cell.

14. The method according to aspect 13, wherein the protein expressed on the surface of an immune cell is CD3.

15. The method according to any of the preceding aspects, wherein the antigen-specific therapeutic comprises a bio-orthogonal adapter molecule.

16. The method according to aspect 15, wherein the bio-orthogonal adapter molecule is bound by an extracellular domain of a switchable CAR.

17. The method according to aspect 16, wherein the bio-orthogonal adapter molecule comprises a peptide neo-epitope (PNE) and the extracellular domain of the switchable CAR binds the PNE.

18. The method according to any of aspects 15 to 17, wherein the bio-orthogonal adapter molecule binds an antigen selected from the group consisting of: EphA2, EphA3, IL13RA1, IL13RA2, EGFR and ERBB2.

19. The method according to any of the preceding aspects, wherein the antigen-specific therapeutic binds two different killing antigens expressed by the glioblastoma.

20. The method according to aspect 19, wherein the two different killing antigens are expressed by EGFRvIII positive glioblastoma cells.

21. The method according to aspect 19, wherein the two different killing antigens are expressed by glioblastoma cells other than EGFRvIII positive glioblastoma cells.

22. The method according to aspect 19, wherein the two different killing antigens are expressed in the same glioblastoma cells.

23. The method according to aspect 19, wherein the two different killing antigens are expressed in different glioblastoma cells.

24. The method according to any of aspects 19 to 23, wherein the two different killing antigens are selected from the group consisting of: EphA2, EphA3, IL13RA1, IL13RA2, EGFR and ERBB2.

25. The method according to aspect 24, wherein the two different killing antigens are EphA2 and IL13RA2.

26. The method according to any of the preceding aspects, wherein the immune cell is further genetically modified with a nucleic acid sequence encoding a second antigen-specific therapeutic that binds to a second killing antigen expressed by the glioblastoma.

27. The method according to aspect 26, wherein the second killing antigen is expressed by EGFRvIII positive glioblastoma cells.

28. The method according to aspect 26, wherein the second killing antigen is expressed by glioblastoma cells expressing the first killing antigen.

29. The method according to aspect 26, wherein the second killing antigen is expressed by a cell of the glioblastoma other than the EGFRvIII positive glioblastoma cells or the glioblastoma cells expressing the first killing antigen.

30. The method according to any of aspects 26 to 29, wherein the second killing antigen is selected from the group consisting of: EphA2, EphA3, IL13RA1, IL13RA2, EGFR and ERBB2.

31. The method according to any of aspects 26 to 30, wherein the second killing antigen is expressed by all cells of the glioblastoma.

32. The method according to any of aspects 26 to 31, wherein the second killing antigen is expressed by non-glioblastoma cells in the subject.

33. The method according to any of the preceding aspects, wherein the BTTS is a SynNotch polypeptide.

34. The method according to any of the preceding aspects, wherein the immune cell is a myeloid cell.

35. The method according to any of aspects 1 to 33, wherein the immune cell is a lymphoid cell.

36. The method according to aspect 35, wherein the lymphoid cell is selected from the group consisting of: a T lymphocyte, a B lymphocyte and a Natural Killer cell.

37. The method according to any of the preceding aspects, wherein the method further comprises identifying that the glioblastoma comprises EGFRvIII positive cells and cells that express the killing antigen.

38. The method according to aspect 37, wherein the identifying comprises assaying a sample of the glioblastoma obtained from the subject for cellular expression of EGFRvIII and the killing antigen.

39. The method according to aspect 38, wherein the sample is a biopsy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Treatment of Glioblastoma Using EGFRviii Prime/Kill Circuit Encoding Therapeutic Cells in a Mouse Model Certain forms of glioblastoma are associated with a unique EGFR splice form called EGFRviii. This unique neoepitope can be targeted by a specific CAR T cell. However, although these CAR T cells have been shown to infiltrate tumors and kill the EGFRviii+ cells in clinical trials, clinical benefit has been limited because EGFRviii expression is highly heterogeneous (expressed in 25-70% of tumor cells) and cancer cells lacking the antigen escape and survive. Thus, the EGFRviii neoantigen has not been effectively harnessed as a target for adoptive CAR T cell therapy.

Conversely, other antigens that could potentially be targeted in GBM are not absolutely specific, and although some are expressed throughout the tumor, they are also be expressed in other normal tissues. Thus, targeting both EGFRviii and one or more other GBM antigens using combined independent therapies could be either ineffective or yield toxic cross-reactivity.

In this example, a novel way to use the targeting specificity of the EGFRviii neoantigen was developed by using it to prime the expression of a second molecule that targets and kills tumor cells based on a second, homogenously expressed antigen (or combination of antigens). This approach is effective even if the second antigen(s) are not perfectly tumor-specific. Without being bound by theory, in essence this approach harnesses two or more imperfect antigens (EGFRviii and the second antigen(s)) to develop a combinatorial T cell that shows both high selectivity and is insensitive to antigen expression heterogeneity.

Figure 1B:
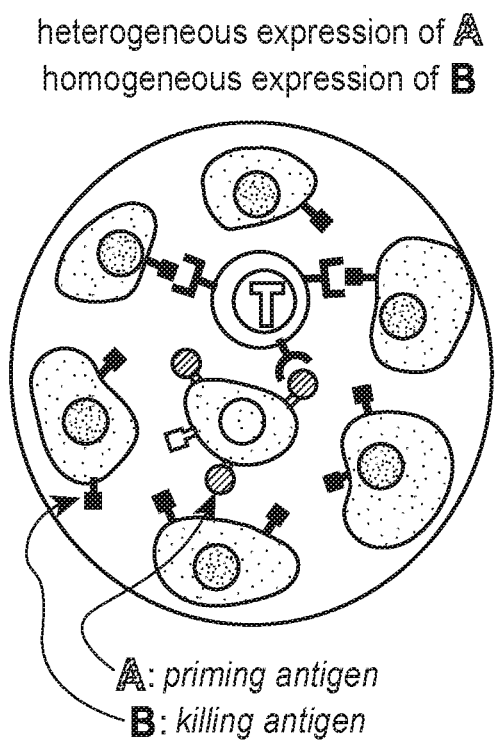

Circuits were designed in which a therapeutic cell is primed based on the tumor specific antigen EGFRviii, inducing expression of killing agent (e.g., a CAR, a BiTE, etc.) that then kills based on a homogenous antigen (see FIG. 1A). In other words, the circuit is primed based on the cancer-specific but heterogeneous antigen, but is then activated to kill in a "killing zone" around the priming antigen cells by targeting a homogeneously expressed antigen (see FIG. 1B). The killing zone size is tunable based on a variety of factors such as, but not limited to, killing receptor (e.g., CAR) stability or the use of extracellular diffusible agents as killing payload (e.g. bispecific adapters) (see FIG. 1C and FIG. 1D).

As depicted in FIG. 1A-1D, priming of therapeutic cells, such as a cell engineered with a circuit as depicted in FIG. 1A, creates a killing zone around the therapeutic cell such that tumor cells expressing the killing antigen are targeted even when such tumor cells do not express the priming antigen. An example of this scenario is schematized in FIG. 1B, which shows a therapeutic cell, shown as a T cell, primed by a tumor heterogeneously expressing the priming antigen, EGFRviii. The primed therapeutic cell targets and kills tumor cells in its proximity, including those expressing the killing antigen but not the priming antigen. In this way, cells in the proximity of the tumor prime the therapeutic cells to create a killing zone around the primed cell, leading to effective clearance of all tumor cells.

Figure 1C:
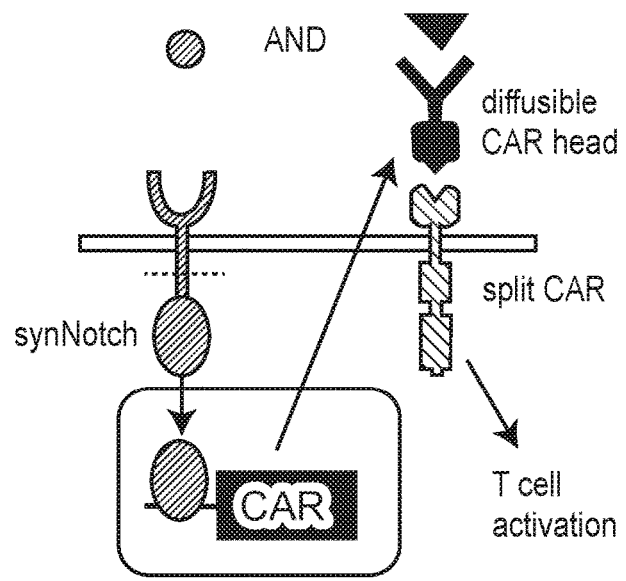

The size of the killing zone may be widened or tuned as desired, e.g., through the use of a diffusible payload, stability of the therapeutic employed (e.g., CAR stability). For example, FIG. 1C depicts a circuit that includes a synNotch binding-triggered transcriptional switch configured to bind a priming antigen (EGFRviii, circle) which induces expression of a diffusible CAR head. The diffusible CAR head is specific for a killing antigen (triangle) and is bound by a portion of a CAR, referred to in FIG. 1C as a "split CAR", that includes the intracellular signaling components necessary for T cell activation upon antigen binding. Accordingly, by diffusing away from the primed cell, the diffusible CAR head serves to mediate antigen recognition and target cell killing in more distant T cells that express the split CAR, but do not necessarily express the diffusible CAR head.

Figure 1D:
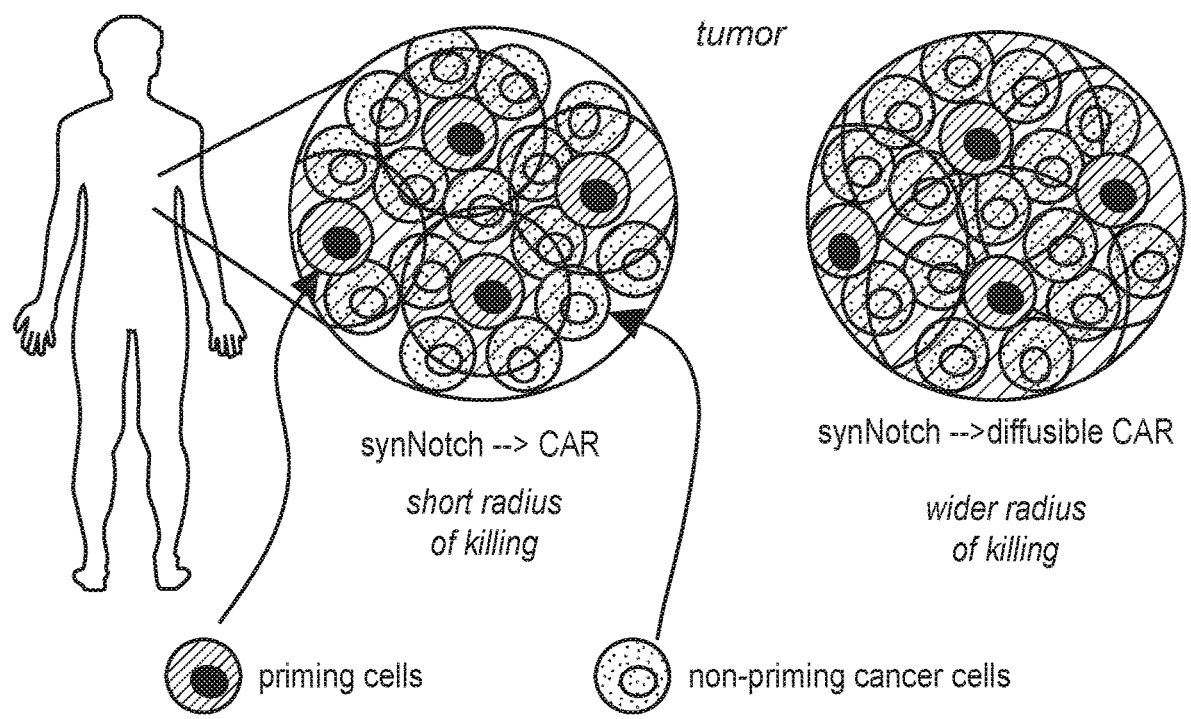

As depicted in the left panel of FIG. 1D, by using a circuit that includes a synNotch driving expression of a traditional CAR (i.e., a single continuous chain having an antigen recognition domain and the intracellular signaling components), the killing radius of non-priming cancer cells that express the killing antigen is kept relatively short. In comparison, as depicted in the right panel of FIG. 1D, by using a circuit that includes a diffusible orthogonal bispecific adapter, such as a diffusible CAR head, the killing radius of non-priming cancer cells that express the killing antigen is widened. Accordingly, the desired killing radius may be controlled as desired. In some instances, e.g., a short killing radius may be desired where a killing antigen is expressed in non-cancerous tissues (i.e., bystander tissues). In other instances, a wide killing radius may be desired where, e.g., relatively few cells expressing the priming antigen are present diffusely throughout a cancerous area of a subject.

Figure 2:
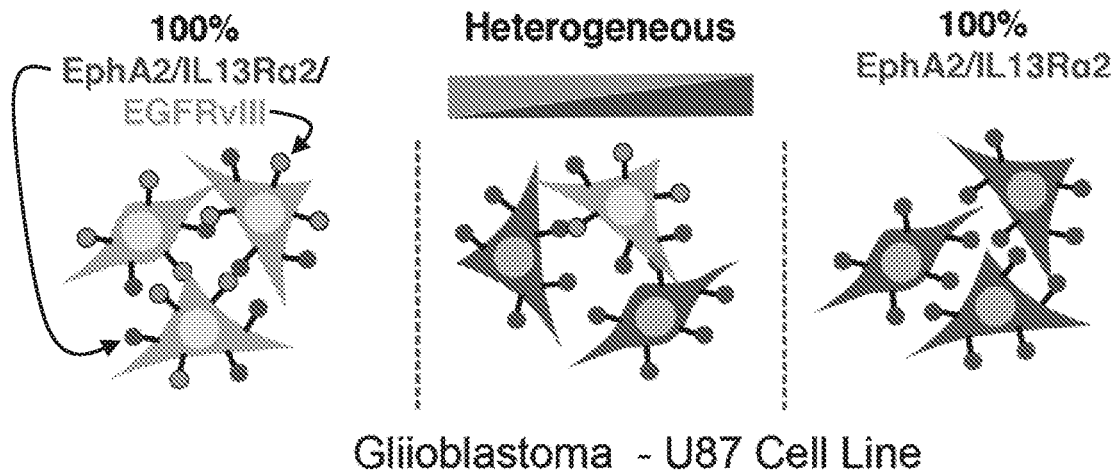
FIG. 2 depicts a schematic representation of a mixed tumor cell line model employed in the examples.
Figure 3:
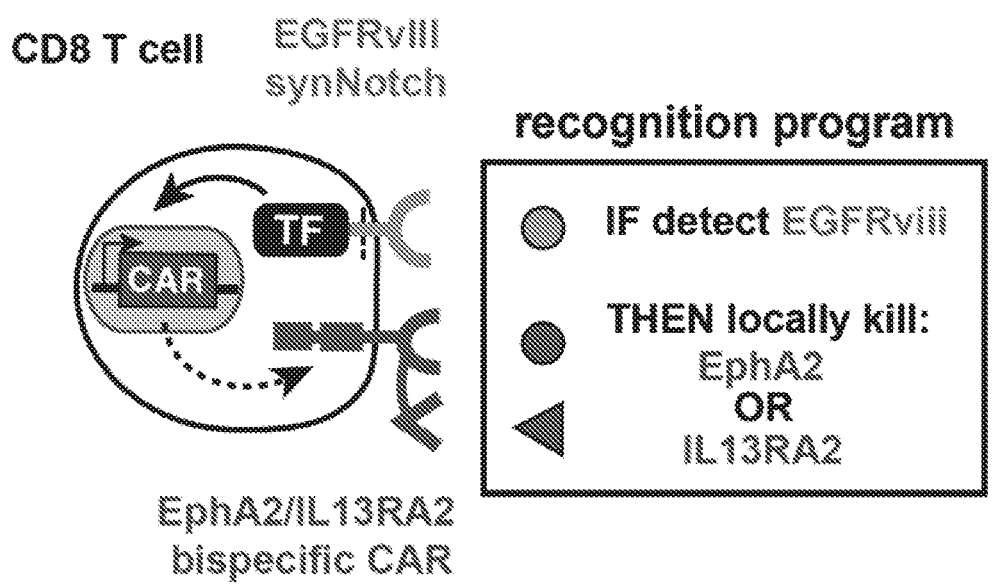
FIG. 3 depicts a schematic representation of a synNotch CAR T cell circuit that engages a priming antigen, EGFRvIII, to then expresses a CAR bi-specific for EphA2 and IL-13RA2.

Whether this type of circuit could function in a GBM model was tested. For this purpose a GBM specific antigen, Epidermal Growth Factor Receptor Variant III (EGFRvIII), as the priming antigen and GBM associated antigen, Ephrin type-A receptor 2 (EphA2) and IL-13 receptor α2, as the target antigen, were used. Tumor cell lines were mixed in varying ratios to recapitulate the heterogeneity observed in GBM patients (10-100% priming surface EGFRvIII U87 mixed with the requisite percentage of target U87 cells) (FIG. 2). Such heterogeneous tumor cell line mixtures were utilized in cytotoxicity assay with an engineered primary human CD8 T cells. These synNotch CAR T cells only express the inducible CAR when the cell engages EGFRvIII antigen, thus, the T cells that are cultured with only EGFRvIII negative U87 cells should not express any CAR. When the synNotch CAR T cell engages the priming antigen, EGFRvIII, the corresponding CAR expresses, and the T cells are 'primed' to kill surrounding target tumor cells (FIG. 3).

Since clinical models of glioblastoma have shown antigen escape to be a problem in tumor recurrence after CAR T cell treatment, testing to determine whether a tandem CAR IL13 mutein-EphA2 CAR could be effectively employed in the context of prime-and-kill circuit was performed. By targeting multiple antigens rather than a single antigen the risk of tumor escape is reduced.

The cytotoxic capability of a constitutive EphA2 CAR or constitutive IL13 Mutein-EphA2 CAR against U87 cells was first tested. The constitutive IL13 Mutein-EphA2 CAR had more efficient cytotoxicity as compared to the constitutive EphA2 CAR alone.

The IL13 Mutein-EphA2 CAR and the EphA2 CAR were tested under the control of anti-EGFRvIII synNotch to evaluate inducibility of expression as well as cytotoxic capacity under the prime-and-kill circuit. Both the IL13 Mutein-EphA2 CAR and the EphA2 CAR were only expressed when synNotch CAR T cells engaged with the priming antigen, EGFRvIII. Therefore, the circuits have minimal to no cytotoxicity to target cells when no priming cells are present. However, unlike the increased cytotoxicity in the constitutive IL13 Mutein-EphA2 CAR when compared against the constitutive EphA2 CAR, no significant difference in cytotoxic activity under the prime-and-kill circuit was observed. Since no decrease in cytotoxic activity was seen and because targeting two different antigen mitigates the risk for tumor escape, the IL13 mutein-EphA2 CAR was used for further characterization in both in vitro and in vivo assay.

Given the above described results, it was expected that the percentage of cells that express the priming antigen would be an important parameter that regulates the effectiveness of the 'prime and kill' circuit with the U87 system. Therefore, the induction of CAR expression and the kinetics of the elimination of two target tumor cell populations over 72 hours were assessed. The results showed that tumor cell populations with a lower percentage of priming tumor cells were more difficult to eliminate since both the level of CAR expression and percentage of T cells positive for CAR expression were lower. Even so, the 'prime and kill' circuit was effective at driving the full eradication of a heterogeneous population of tumor cells where only 10% of the tumor cells expressed the priming antigen (FIG. 4). Furthermore, it was observed that decreasing the ratio of priming antigen led to delayed killing kinetics (FIG. 5). All together, these findings show that synNotch CAR T cell prime/kill circuits may be employed to address heterogeneous tumors in glioblastoma and such circuits reduce both the chances of tumor escape and off-target toxicity.

The effectiveness of a prime/kill circuit based on priming with EGFRviii was also demonstrated using an in vivo preclinical heterogeneous GBM model, with 50% of GBM cells of the heterogeneous tumor expressing EGFRviii and 50% of GBM cells of the heterogeneous tumor negative for EGFRviii. Mice carrying the heterogeneous GBM model tumors were administered therapeutic T cells encoding a prime/kill circuit employing a synNotch receptor detecting EGFRviii to trigger expression of a two headed CAR (with domains that recognize EphA2 and IL13R antigens).

Figure 6A:
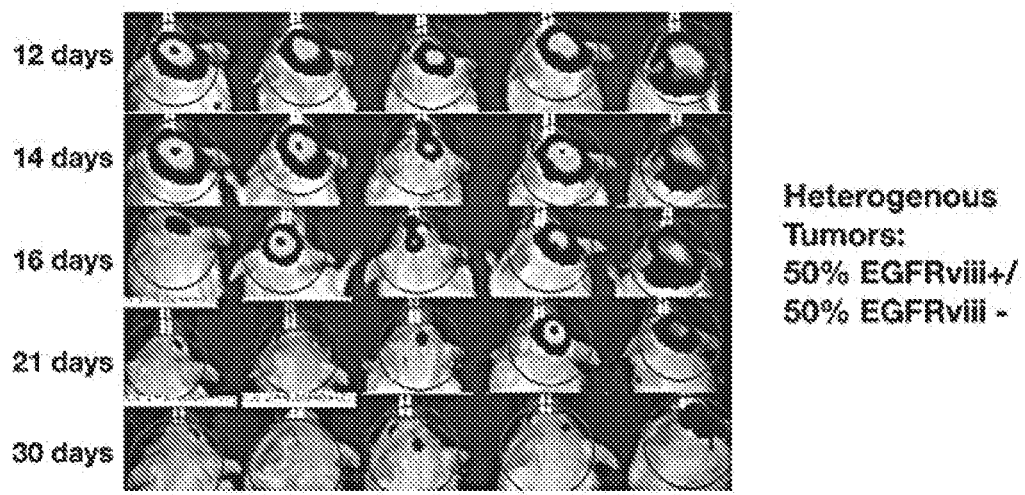
FIG. 6A-6C show the effective in vivo treatment of glioblastomas, in a representative preclinical mouse model, using an EGFRviii prime/kill circuit as described herein.
Figure 6B:
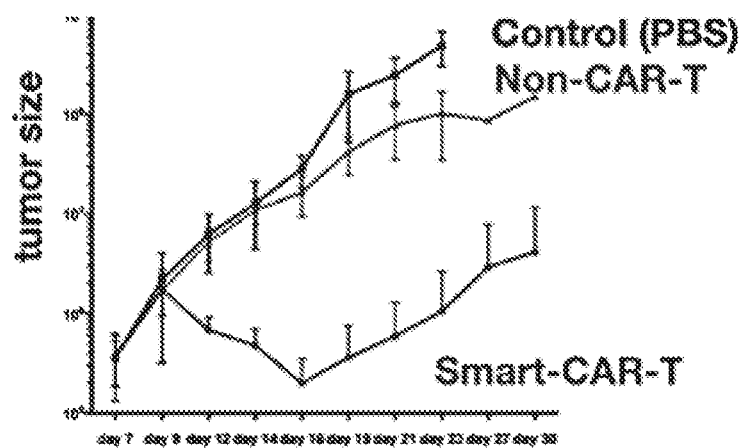
Figure 6C:
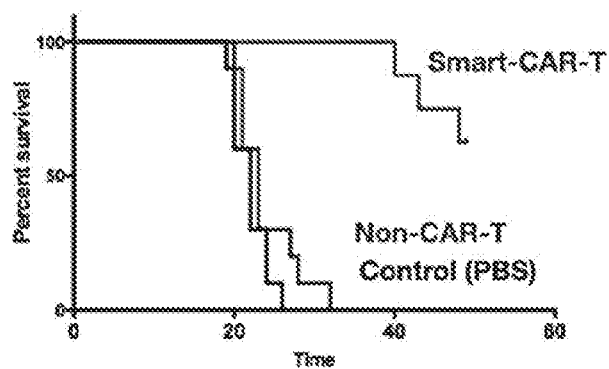

A time course displaying tumor reduction in five (5) of the treated mice is provided in FIG. 6A. Tumor size and model animal survival was also quantified. As shown in FIG. 6B, animals treated with cells encoding the EGFRviii priming and EphA2/IL13R killing circuit (refereed to "Smart-CAR-T") showed a reduction in tumor growth as compared to both vehicle ("PBS") and "Non-CAR-T" treated controls. As shown in FIG. 6C, mice treated with Smart-CAR-T cells also showed prolonged survival as compared to controls.

Figure 7:
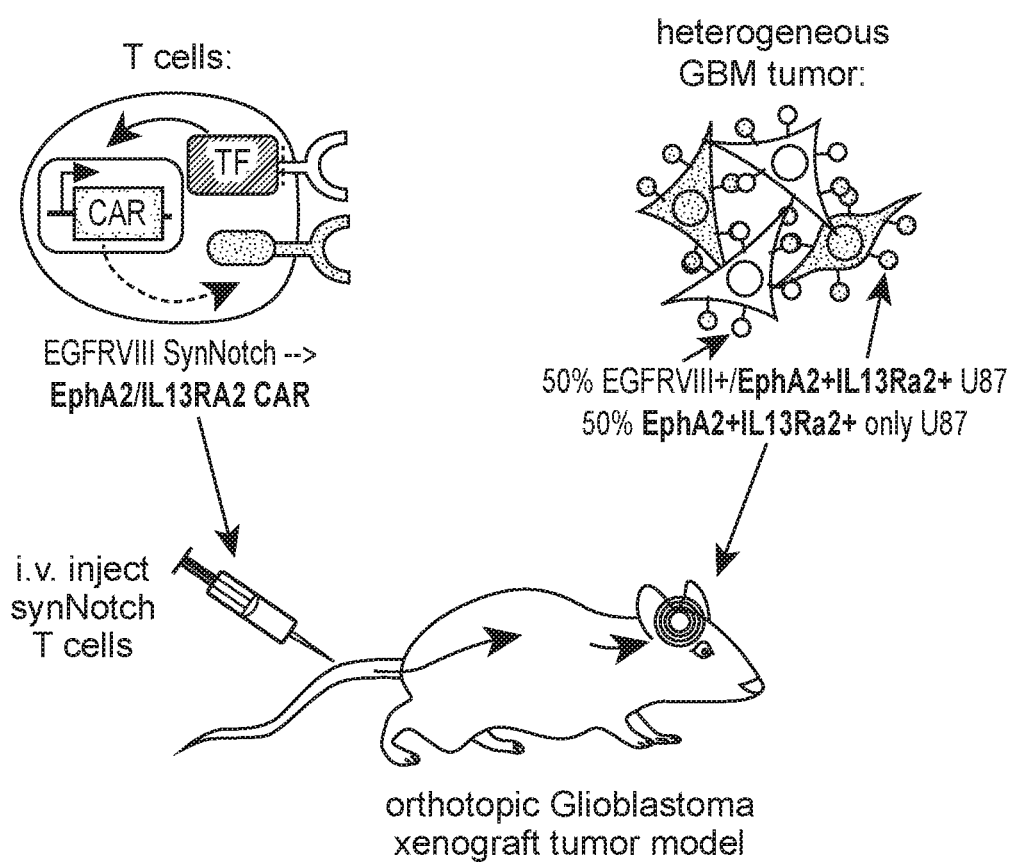
FIG. 7 depicts a schematic representation of a heterogeneous GBM tumor treatment model as described in the examples.
Figure 8:
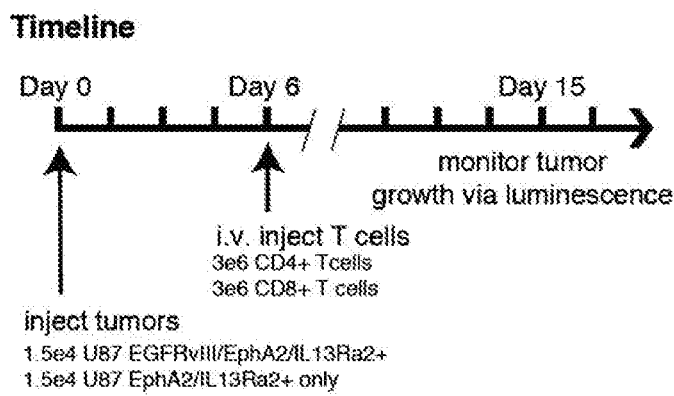
FIG. 8 depicts a timeline relevant to the heterogeneous GBM tumor treatment model.

In a further experiment U87wt (EphA2 and IL13ra2 expressing only) cells were mixed with U87-EGFRvIII cells in a 1:1 ratio and engrafted orthotopically into immunodeficient mice (see FIG. 7). In vivo heterogeneity of the SynNotch priming antigen, EGFRviii, was confirmed by histological examination of the brain on day 7. Mice were distributed according to tumor burden into equivalent treatment and control groups before receiving a single intravenous injection of 6 million of either EGFRviii-synCART or non-transduced T cells one week after establishment of heterogeneous GBM xenograft (FIG. 8).

Figure 9:
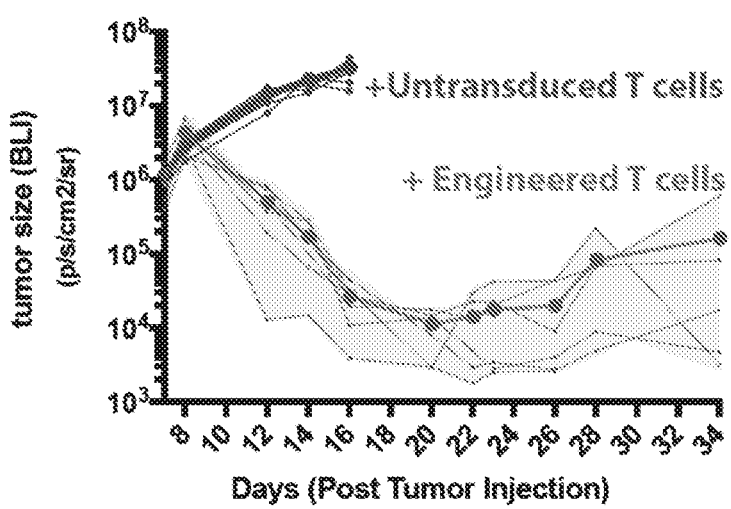
FIG. 9 depicts that mice treated with synCART showed a reduction in tumor burden as compared to controls.
Figure 10:
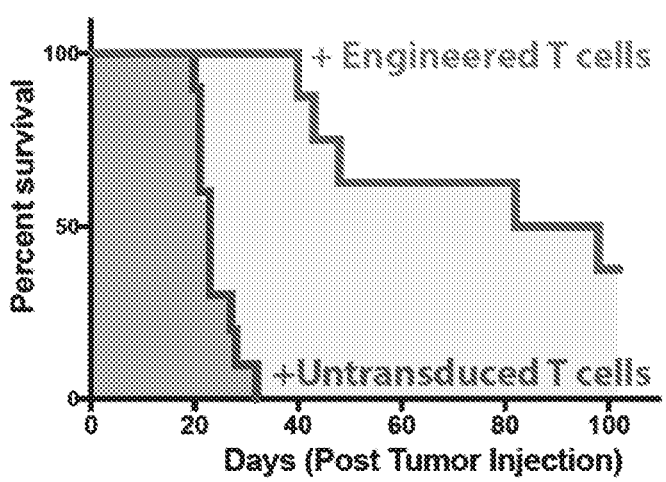
FIG. 10 depicts that mice treated with synCART showed increased survival as compared to controls.

Marked reduction in tumor burden was observed in the cohort of mice treated with synCART as assessed by longitudinal bioluminescence imaging (FIG. 9). In addition, substantial improvement in the survival was seen in the synCART-treated mice compared with non-transduced T cell treated controls (FIG. 10). Systemic delivery of synCART achieved potent and lasting tumor clearance as seen in follow-up histologic analysis of the brains of treated mice censored due to non-tumor related issues at endpoint triggered by the onset of GVHD.

Figure 11:
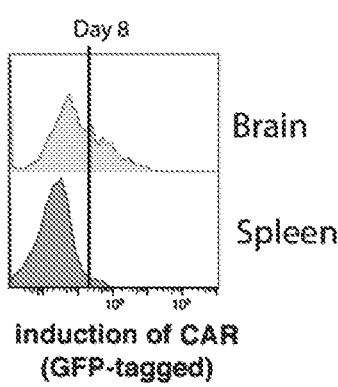
FIG. 11 demonstrates that expression of killing CAR in the synCART system is localized to the microenvironment bearing the priming antigen.

To study the in vivo dynamics of CAR expression following recognition of priming antigen EGFRviii, tumors were examined two days after administration of synCART. Upregulation of IL13 mutein-anti-EphA2 CAR (killing CAR) was observed, measured by a c-terminally tagged GFP, in the brain but not spleen (FIG. 11). This finding shows that expression of killing CAR is localized to the microenvironment bearing priming antigen. Furthermore, the induced CAR expression in the brain was downregulated with reduction in tumor burden.

Figure 12:
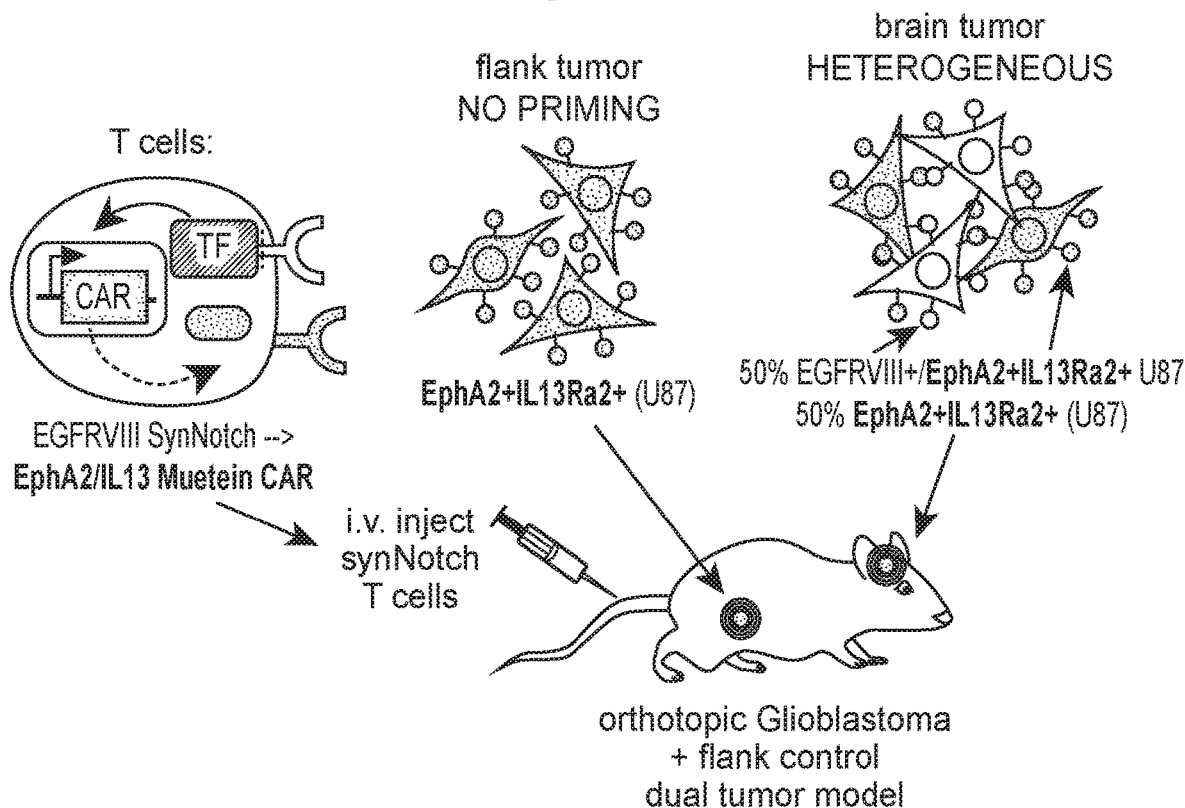
FIG. 12 depicts a schematic representation of a dual tumor model was employed to assess the ability of prime-and-kill T cells to ignore off-target/bystander cells.

The ability of prime-and-kill T cells to ignore off-target/bystander cells was also investigated using a flank control tumor expressing killing antigen (EphA2/IL13RA2) but lacking priming antigen. Put another way, given the observed success of EGFRviii-synCART in reducing tumor burden, whether prime-and-kill T cells activated in heterogeneous tumors would migrate out and attack cells expressing killing antigen alone was investigated. For these experiments, a dual tumor model was employed: a heterogeneous (1:1 U87-EGFRviii/U87wt) intracranial tumor and a flank tumor (U87wt—lacking priming antigen) (FIG. 12).

Figure 13:
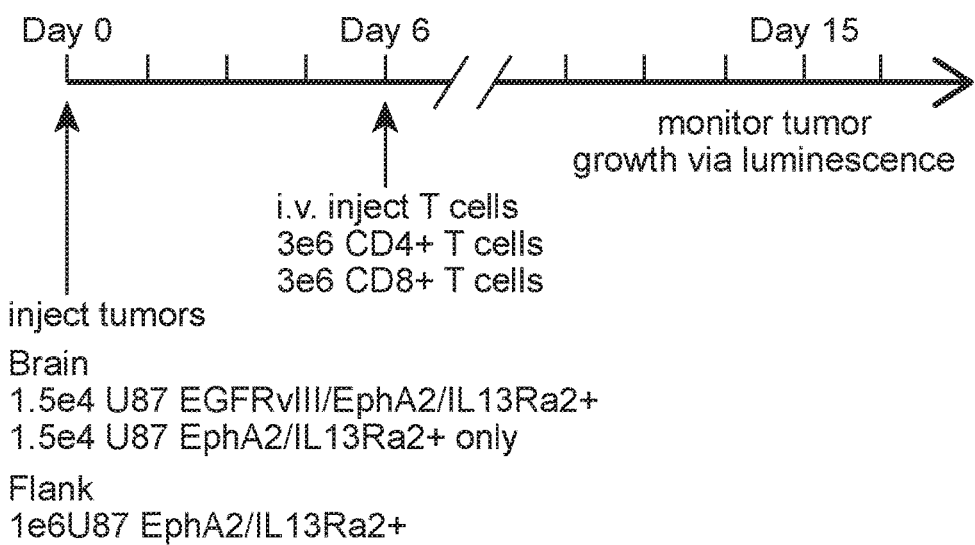
FIG. 13 depicts a timeline relevant to the dual tumor model.
Figure 14:
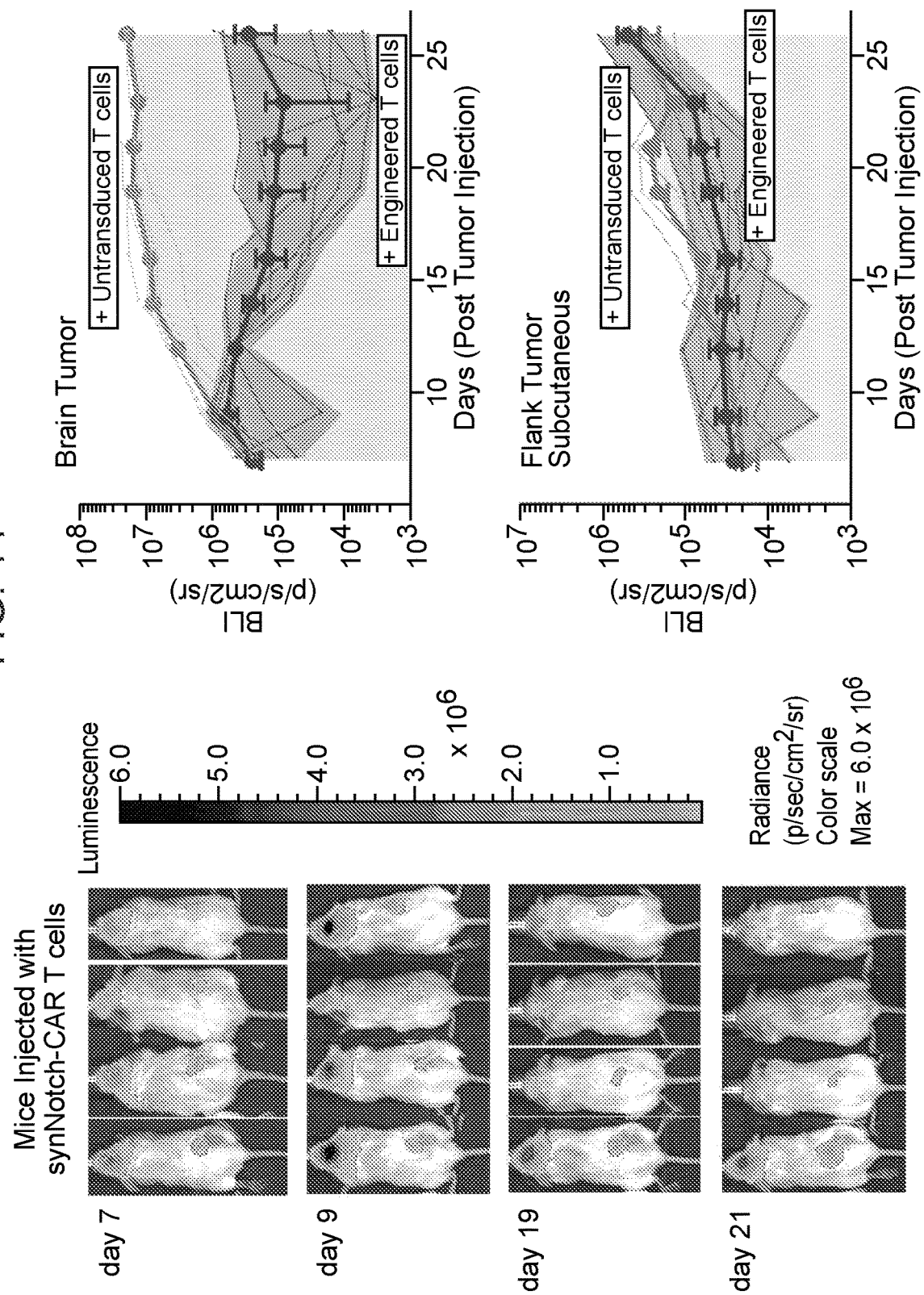
FIG. 14 demonstrates that synCART treated mice showed a reduction in brain tumor burden but bystander flank cells were unaffected.

Tumors were implanted and on day 6 CD4+ and CD8+ T cells engineered to express EGFRviii-synCAR were injected (FIG. 13). Tumor burden was assessed by longitudinal bioluminescence imaging. Mice treated with control untransduced T cells reached euthanasia endpoint rapidly while synCART treated animals displayed marked reduction in intracranial tumor burden without any impact on the growth of flank tumor (FIG. 14). This in vivo data shows that SynNotch driven IL13mutein/EphA2 CAR expression and T cell functionality is confined to tumors expressing both priming and killing antigen. No evidence of priming of synCART in flank tumors was observed, showing that the activate/kill behavior of synCART was absent in EphA2+ bystander tissues.

Collectively, these data demonstrate the effectiveness of prime/kill circuits using EGFRviii as the priming antigen for treating heterogeneous GBM.

Materials & Methods

SynNotch Receptor and Response Element Construct Design: SynNotch receptors were built by fusing the LaG17 (lower affinity GFP), or EGFRvIII 139 scFv (Johnson et al. Sci Transl Med. (2015) 7(275):275ra2; the disclosure of which is incorporated herein by reference in its entirety) to the mouse Notch1 (NM_008714) minimal regulatory region (Ile1427 to Arg1752) and Gal4 DBD VP64. All synNotch receptors contain an n-terminal CD8a signal peptide (MALPVTALLLPLALLLHAARP; SEQ ID NO:24) for membrane targeting and a myc-tag (EQKLISEEDL; SEQ ID NO:25) or flag-tag (DYKDDDDK; SEQ ID NO:26) for easy determination of surface expression with a-myc A647 (cell-signaling) or a-flag A647 (RND systems); see Morsut et al., Cell. (2016) 164(4):780-91 (the disclosure of which is incorporated herein by reference in its entirety) for synNotch receptor peptide sequences). The receptors were cloned into a modified pHR'SIN:CSW vector containing a PGK or SFFV promoter for all primary T cell experiments. The pHR'SIN:CSW vector was also modified to make the response element plasmids. Five copies of the Gal4 DNA binding domain target sequence (GGAGCACTGTCCTCCGAACG; SEQ ID NO:27) were cloned 5' to a minimal CMV promoter. Also included in the response element plasmids is a PGK promoter that constitutively drives mCherry or BFP expression to easily identify transduced T cells. Inducible EphA2 CAR was built by fusing the CD19 scFv (Porter et al. N Engl J Med. (2011) 365(8):725-33; the disclosure of which is incorporated herein by reference in its entirety), EphA2 scFv (Goldgur et al., Growth Factors. (2014) 32(6):214-22; the disclosure of which is incorporated herein by reference in its entirety), IL13 Mutein [E13K, K105R] (Krebs et al., Cytotherapy. (2014) 16(8):1121-3; the disclosure of which is incorporated herein by reference in its entirety)-G4Sx4-EphA2 scFv (Goldgur et al.) to the hinge region of the human CD8a chain and transmembrane and cytoplasmic regions of the human 4-1BB, and CD3z signaling endodomains. The inducible CAR constructs were cloned via a BamHI site in the multiple cloning site 3' to the Gal4 response elements. For some inducible CAR vectors, the CARs were tagged c-terminally with GFP/BFP or contain myc/flag tag to verify surface expression. All constructs were cloned via in fusion cloning (Clontech/Takara).

Primary Human T Cell Isolation and Culture: Primary CD4+ and CD8+ T cells were isolated from anonymous donor blood after apheresis by negative selection (STEMCELL Technologies). T cells were cryopreserved in RPMI-1640 with 20% human AB serum (Valley Biomedical) and 10% DMSO. After thawing, T cells were cultured in human T cell medium consisting of X-VIVO 15 (Lonza), 5% Human AB serum, and 10 mM neutralized N-acetyl L-Cysteine (Sigma-Aldrich) supplemented with 30 units/mL IL-2 (NCI BRB Preclinical Repository) for all experiments.

Lentiviral Transduction of Human T Cells: Pantropic VSV-G pseudotyped lentivirus was produced via transfection of Lenti-X 293T cells (Clontech/Takara) with a pHR'S-IN:CSW transgene expression vector and the viral packaging plasmids pCMVdR8.91 and pMD2.G using Fugene HD (Promega). Primary T cells were thawed the same day and, after 24 hr in culture, were stimulated with Human T-Activator CD3/CD28 Dynabeads (Life Technologies) at a 1:3 cell:bead ratio. At 48 hr, viral supernatant was harvested and the primary T cells were exposed to the virus for 24 hr. At day 4 after T cell stimulation, the Dynabeads were removed, and the T cells expanded until day 9 when they were rested and could be used in assays. T cells were sorted for assays with a Beckton Dickinson (BD) FACs ARIA Fusion. AND-gate T cells exhibiting basal CAR expression were gated out during sorting.

Cancer Cell Lines: The cancer cell lines used were K562 myelogenous leukemia cells (ATCC) and U87 MG glioblastoma cells (ATCC). K562s were lentivirally transduced to stably express human CD19 at equivalent levels as Daudi tumors. CD19 levels were determined by staining the cells with a-CD19 PE-Cy7 (BD Biosciences). K562s cells were also transduced to stably express surface GFP (GFP fused to the PDGF transmembrane domain). The CD19 and surface-GFP peptide sequences can be found in Morsut et al., (2016). U87 MG were lentivirally transduced to stably express GFP or mCherry under control of the spleen focus-forming virus (SFFV) promoter. At 72 hours after transductions, cells were sorted on an Aria Fusion cell sorter (BD Biosciences) on the basis of GFP expression to be 100% GFP or mCherry positive and subsequently expanded. All cell lines were sorted for expression of the transgenes.

In Vitro Stimulation of SynNotch T cells: For all in vitro synNotch T cell stimulations, $1 \times 10^5$ T cells were co-cultured with $1 \times 10^5$ K562 cells in complete human T cell media. After mixing the T cells and cancer cells in round bottom 96-well tissue culture plates, the cells were centrifuged for 1 min at 400×g to force interaction of the cells, and the cultures were analyzed at 24-72 hr for activation and specific lysis of target tumor cells. For all in vitro synNotch T cell stimulations co-cultured with U87, $1 \times 10^4$ U87s were cultured overnight in a flat bottom 96-well tissue culture plate. Next morning, $1 \times 10^4$-$5 \times 10^4$ T cells were added to the flat bottom 96-well tissue culture plate and the co-cultures were analyzed at 24-96 hr for activation and specific lysis of target tumor cells. All flow cytometry was performed using BD LSR II or Attune NxT Flow Cytometer and the analysis was performed in FlowJo software (TreeStar).

Assessment of SynNotch AND-Gate T Cell Cytotoxicity: CD8+ synNotch AND-Gate T cells were stimulated for 24-96 hr as described above with target cells expressing the indicated antigens. The level of specific lysis of target cancer cells was determined by comparing the fraction of target cells alive in the culture compared to treatment with untransduced T cell controls. Cell death was monitored by shifting of the target cells out of the side scatter and forward scatter region normally populated by the target cells. Alternatively, cell viability was analyzed using the IncuCyte Zoom system (Essen Bioscience). The target cells and T cells were co-cultured as described above. 2 fields of view were taken per well every 15 minutes. The mean florescence intensity (MFI) was calculated using IncuCyte Zoom software (Essen BioScience) in order to determine the target cell survival.

Mouse Models: For orthotropic heterogeneous model, mix of $1.5 \times 10^4$ U87-luc-mCherry and $1.5 \times 10^4$ U87-luc-EGFRvIII-GFP cells were implanted intracranially into 6- to 8-week-old female NCG mice (Charles River), with 6-10 mice per group. The surgical implants were done using a stereotactic surgical setup with tumor cells implanted 2 mm right and 1 mm anterior to the bregma and 3 mm into the brain. Before surgery and for 3 days after surgery, mice were treated with an analgesic and monitored for adverse symptoms. In subcutaneous model, NCG mice were injected with $1.0 \times 10^6$ U87-Luc-mcherry tumors subcutaneously in 100 μl of HBSS on day 0. Tumor progression was evaluated by luminescence emission on a Xenogen IVIS Spectrum after intraperitoneal D-luciferin injection according to the manufacturer's directions (GoldBio). Prior to the treatment, mice were randomized such that initial tumor burden in the control and treatment groups were equivalent. Mice were treated with $6.0 \times 10^6$ CART or a matched number of untransduced T cells intravenously via tail vein in 100 μl of PBS. Survival was followed over time until predetermined endpoint was reached (n=6 to 10 mice per group).

Immunofluorescence and Confocal Microscopy: Mice were euthanized before being perfused transcardially with cold PBS. Brains were then removed and fixed overnight in 4% PFA-PBS before being transferred to 30% sucrose and were allowed to sink (1-2 d). Subsequently, the brains were embedded in O.C.T. Compound (Tissue-Tek; 4583; Sakura Finetek). Serial 10-μm coronal sections were then cut on freezing microtome and stored at −20° C. Images were acquired using a Zeiss Axio Imager 2 microscope (×20 magnification) and TissueFAXS scanning software (TissueGnostics). Identical exposure times and threshold settings were used for each channel on all sections of similar experiments.

Examples of Relevant Amino Acid Sequences (And Domains Thereof) Employed in the Examples and/or Employable in the Described Methods:

EGFRvIII synNotch receptor:
(SEQ ID NO: 28)
DIQMTQSPSSLSASVGDRVTITCRASQGIRNNLAWYQQKPGKAPKRLIYA

ASNLQSGVPSRFTGSGSGTEFTLIVSSLQPEDFATYYCLQHHSYPLTSGG

GTKVEIKGSTSGSGKPGSGEGSEVQVLESGGGLVQPGGSLRLSCAASGFT

FSSYAMSWVRQAPGKGLEWVSAISGSGGSTNYADSVKGRFTISRDNSKNT

LYLQMNSLRAEDTAVYYCAGSSGWSEYWGQGTLVTVSSILDYSFTGGAGR

DIPPPQIEEACELPECQVDAGNKVCNLQCNNHACGWDGGDCSLNFNDPWK

NCTQSLQCWKYFSDGHCDSQCNSAGCLFDGFDCQLTEGQCNPLYDQYCKD

HFSDGHCDQGCNSAECEWDGLDCAEHVPERLAAGTLVLVVLLPPDQLRNN

SFHFLRELSHVLHTNVVFKRDAQGQQMIFPYYGHEEELRKHPIKRSTVGW

ATSSLLPGTSGGRQRRELDPMDIRGSIVYLEIDNRQCVQSSSQCFQSATD

VAAFLGALASLGSLNIPYKIEAVKSEPVEPPLPSQLHLMYVAAAAFVLLF

FVGCGVLLSRKRRRMKLLSSIEQACDICRLKKLKCSKEKPKCAKCLKNNW

ECRYSPKTKRSPLTRAHLTEVESRLERLEQLFLLIFPREDLDMILKMDSL

QDIKALLTGLFVQDNVNKDAVTDRLASVETDMPLTLRQHRISATSSSEES

SNKGQRQLTVSAAAGGSGGSGGSDALDDFDLDMLGSDALDDFDLDMLGSD

ALDDFDLDMLGSDALDDFDLDMLGS
(EGFRvIII scFv; Notch Core; Gal4VP64)

EphA2 CAR:
(SEQ ID NO: 29)
EIVLTQSPGTLSLSPGERATLSCRASQSVSSSNLAWYQQKPGQAPRLLIY

GASSRATGVPDRFSGSGSGTDFTLTISRLEPEDFAVYYCQQSSSYPWTFG

QGTKVEIKRTGGGGSGAGGSGGGGTGGGGSEVDLLESGGGLVQPGGSLRL

SCAASGFTFSRYWMHWVRQAPGKGLEWVSSISPYDGETNYADSVKGRFTI

SRDNSKNTLYLQMNSLRAEDTAVYYCARISEWYNWAVDVFDYWGQGTLVT

VSSTTTPAPRPPTPAPTIASQPLSLRPEACRPAAGGAVHTRGLDFACDIY

IWAPLAGTCGVLLLSLVITLYCGSGSGSGSGSKRGRKKLLYIFKQPFMRP

VQTTQEEDGCSCRFPEEEEGGCELGSGSGSRVKFSRSADAPAYKQGQNQL

YNELNLGRREEYDVLDKRRGRDPEMGGKPRRKNPQEGLYNELQKDKMAEA

YSEIGMKGERRRGKGHDGLYQGLSTATKDTYDALHMQALPPR
(EphA2 scFv; CD8alpha hinge Transmembrane Domain; GSlinker-41BB-CD3Zeta Domain)

IL13Ra2 CAR:
(SEQ ID NO: 30)
*LTCLGGFASPGPVPPSTALRKLIEELVNITQNQKAPLCNGSMVWSINLTA*

*GMYCAALESLINVSGCSAIEKTQRMLSGFCPHKVSAGQFSSLHVRDTKIE*

*VAQFVKDLLLHLRKLFREGRFN*TTTPAPRPPTPAPTIASQPLSLRPEACR

PAAGGAVHTRGLDFACDIYIWAPLAGTCGVLLLSLVITLYCGSGSGSGSG

SKRGRKKLLYIFKQPFMRPVQTTQEEDGCSCRFPEEEEGGCELGSGSGSR

VKFSRSADAPAYKQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR
(IL13 Mutein; CD8alpha hinge Transmembrane Domain; GSlinker-41BB-CD3Zeta Domain)

EphA2/IL13Ra2 CAR:
(SEQ ID NO: 31)
*LTCLGGFASPGPVPPSTALRKLIEELVNITQNQKAPLCNGSMVWSINLTA*

*GMYCAALESLINVSGCSAIEKTQRMLSGFCPHKVSAGQFSSLHVRDTKIE*

*VAQFVKDLLLHLRKLFREGRFN*GGGSGGGSGGGSGGGSEIVLTQSPGTLS

LSPGERATLSCRASQSVSSSNLAWYQQKPGQAPRLLIYGASSRATGVPDR

FSGSGSGTDFTLTISRLEPEDFAVYYCQQSSSYPWTFGQGTKVEIKRTGG

GGSGAGGSGGGGTGGGGSEVDLLESGGGLVQPGGSLRLSCAASGFTFSRY

WMHWVRQAPGKGLEWVSSISPYDGETNYADSVKGRFTISRDNSKNTLYLQ

MNSLRAEDTAVYYCARISEWYNWAVDVFDYWGQGTLVTVSSTTTPAPRPP

TPAPTIASQPLSLRPEACRPAAGGAVHTRGLDFACDIYIWAPLAGTCGVL

LLSLVITLYCGSGSGSGSGSKRGRKKLLYIFKQPFMRPVQTTQEEDGCSC

RFPEEEEGGCELGSGSGSRVKFSRSADAPAYKQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR
(IL13 Mutein; GSLinker; EphA2 scFv; CD8alpha hinge Transmembrane Domain; GSlinker-41BB-CD3Zeta Domain)

Bi-specific EphA2:
(SEQ ID NO: 32)
QVQLLESGGGLVQPGGSLRLSCAASGFTFSSYTMSWVRQAPGQALEWMGT

ISSGGTYTYYPDSVKGRFTISRDNAKNSLYLQMNSLRAEDTAVYYCAREA

IFTYWGRGTLVTSSGGGGSGGGGSGGGGSDIQLTQSPSSLSASVGDRVTI

TCKASQDINNYLSWYQQKPGQAPRLLIYRANRLVDGVPDRFSGSGYGTDF

TLTINNIESEDAAYYFCLKYDVFPYTFGQGTKVEIKSGGGGSDIKLQQSG

AELARPGASVKMSCKTSGYTFTRYTMHWVKQRPGQGLEWIGYINPSRGYT

NYNQKFKDKATLTTDKSSSTAYMQLSSLTSEDSAVYYCARYYDDHYCLDY

WGQGTTLTVSSGGGGSGGGGSGGGGSDIQLTQSPAIMSASPGEKVTMTCR

ASSSVSYMNWYQQKSGTSPKRWIYDTSKVASGVPYRFSGSGSGTSYSLTI

SSMEAEDAATYYCQQWSSNPLTFGAGTKLELKS
(EphA2 4H5 scFv; GSLinker; CD3 OKT3 scFv)

PNE Peptide Orthogonal Bispecific EphA2:
(SEQ ID NO: 33)
*NYHLENEVARLKKL*LVGEAAAKEAAAKAQVQLLESGGGLVQPGGSLRLSC

AASGFTFSSYTMSWVRQAPGQALEWMGTISSGGTYTYYPDSVKGRFTISR

DNAKNSLYLQMNSLRAEDTAVYYCAREAIFTYWGRGTLVTSSGGGGSGGG

GSGGGGSDIQLTQSPSSLSASVGDRVTITCKASQDINNYLSWYQQKPGQA

PRLLIYRANRLVDGVPDRFSGSGYGTDFTLTINNIESEDAAYYFCLKYDV

FPYTFGQGTKVEIKS

-continued (PNE Peptide; EAAAK Linker; EphA2 4H5 scFv)

PNE Peptide Cognate CAR:

(SEQ ID NO: 34)
DAVVTQESALTSSPGETVTLTCRSSTGAVTTSNYASWVQEKPDHLFTGLI

GGTNNRAPGVPARFSGSLIGDKAALTITGAQTEDEAIYFCVLWYSDHWVF

GGGTKLTVLGGGGSGGGGSGGGGSGGGGSDVQLQESGPGLVAPSQSLSI

TCTVSGFLLTDYGVNWVRQSPGKGLEWLGVIWGDGITDYNSALKSRLSVT

KDNSKSQVFLKMNSLQSGDSARYYCVTGLFDYWGQGTTLTVSSESKYGPP

CPPCPIYIWAPLAGTCGVLLLSLVITLYCKRGRKKLLYIFKQPFMRPVQT

TQEEDGCSCRFPEEEEGGCELRVKFSRSADAPAYKQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR
(PNE 52SR4 scFv; IgG4m hinge; CD8alpha Transmembrane Domain; 41BB-CD3Zeta Domain)

Example 2

Multi-Receptor Circuits for IF/THEN Gated EGFRvIII Dependent T Cell Activation

Figure 15A:
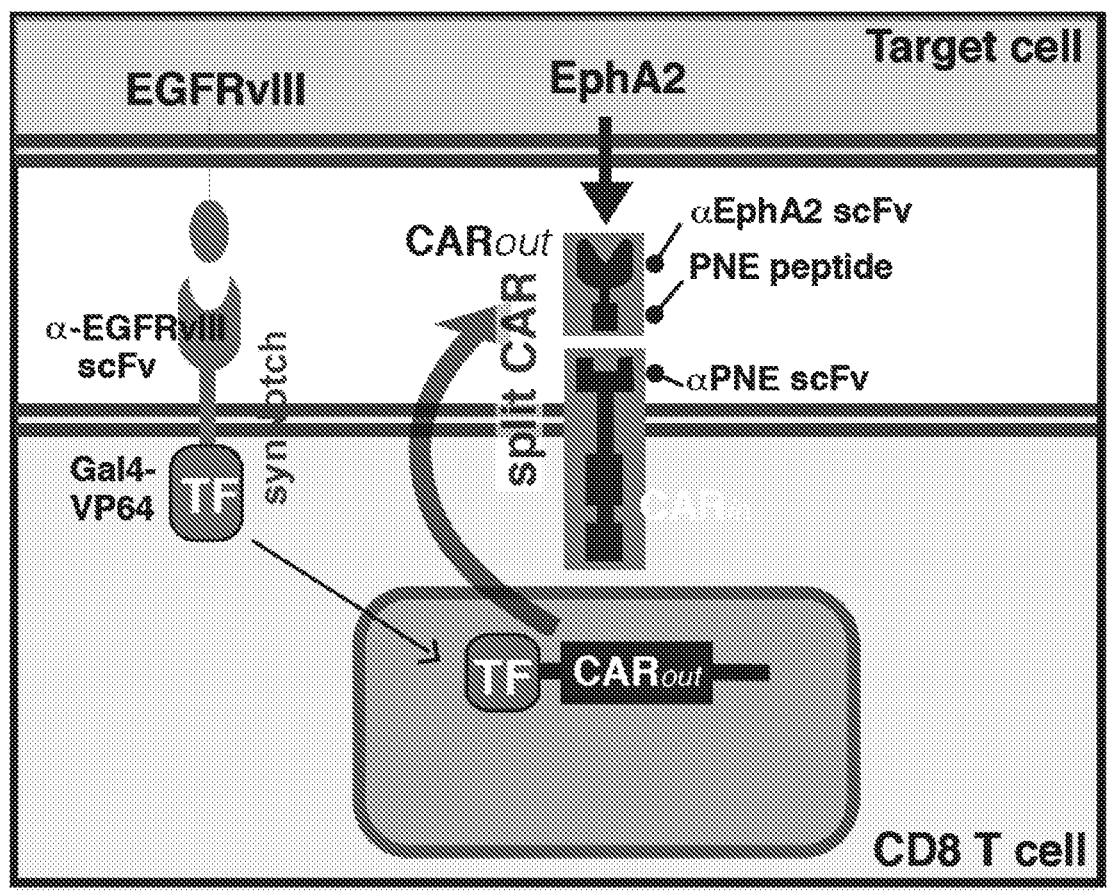
FIG. 15A-15D demonstrates killing of GBM target cells using a 2-receptor IF/THEN circuit dependent on the presence of EGFRvIII priming cells for CAR activity and target cell killing.

A molecular circuit was designed to demonstrate the use of an EGFRvIII dependent IF/THEN gate. A schematic depiction of the designed 2-receptor circuit engineered in primary human CD8 T cells to generate a 2-input IF/THEN gate controlling T cell activation is shown in FIG. 15A. In the depicted circuit a synNotch receptor specific for anti-EGFRvIII is expressed in CD8 T cells to control the expression of a split CAR through the release of the a Gal4VP64 transcription factor (TF) domain upon EGFRvIII antigen binding. The split CAR is made up of an anti-PNE-CAR ($CAR_{in}$) portion and a secreted portion ($CAR_{out}$) containing an anti-Epha2 scFv linked to the PNE peptide. The anti-EGFRvIII Gal4-VP64 synNotch controls expression of the $CAR_{out}$, and once $CAR_{out}$ is expressed, engineered CD8 T cells become capable of recognizing and killing EphA2+ target cells.

Figure 15B:
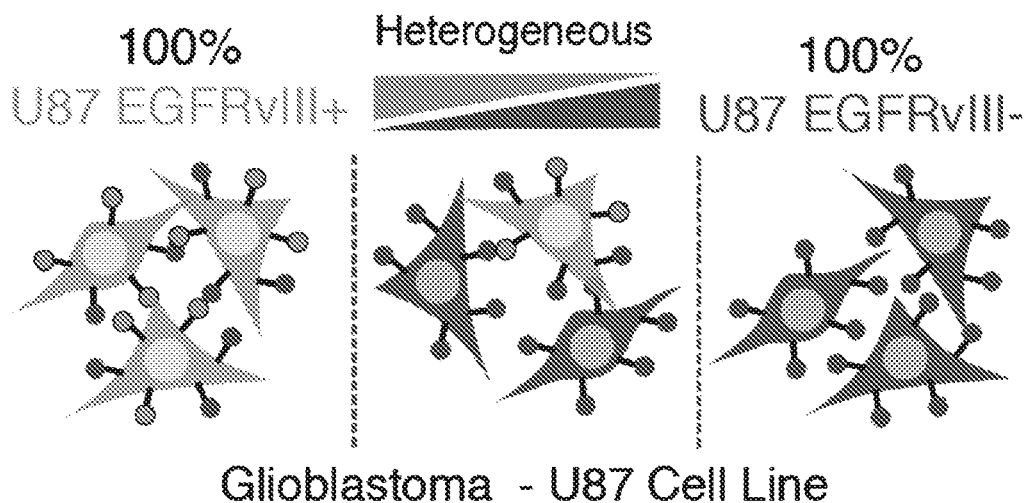

To test the above described circuit the heterogeneity observed in GBM was mimicked using engineered U87 GBM cell lines (FIG. 15B). U87 cells express EphA2, but not EGFRvIII ("U87 EGFRvIII-" cells—here also referred to as "target" cells). U87 cells that also express the EGFRvIII priming antigen ("U87 EGFRvIII+" cells—here also referred to as "priming" cells) were also used. Different levels of heterogeneity were systematically generated by mixing these different U87 cells at different ratios. Tumor cells were labeled with different fluorescent proteins to allow tracking of cell survival for each individual cell type.

Figure 15C:
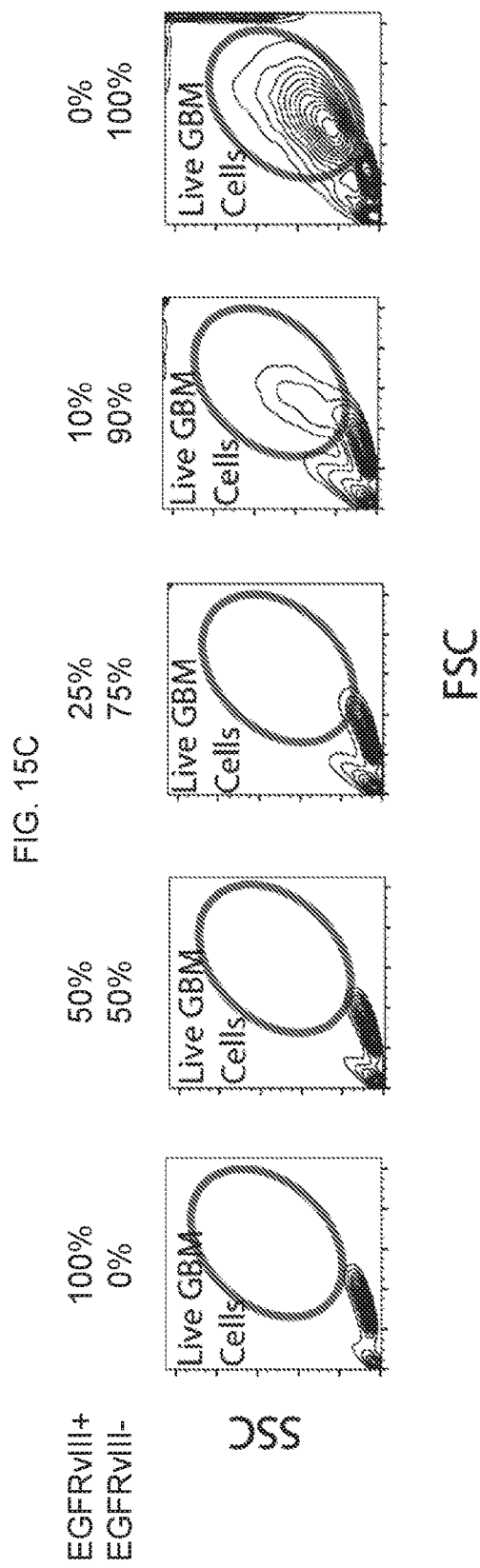
Figure 15D:
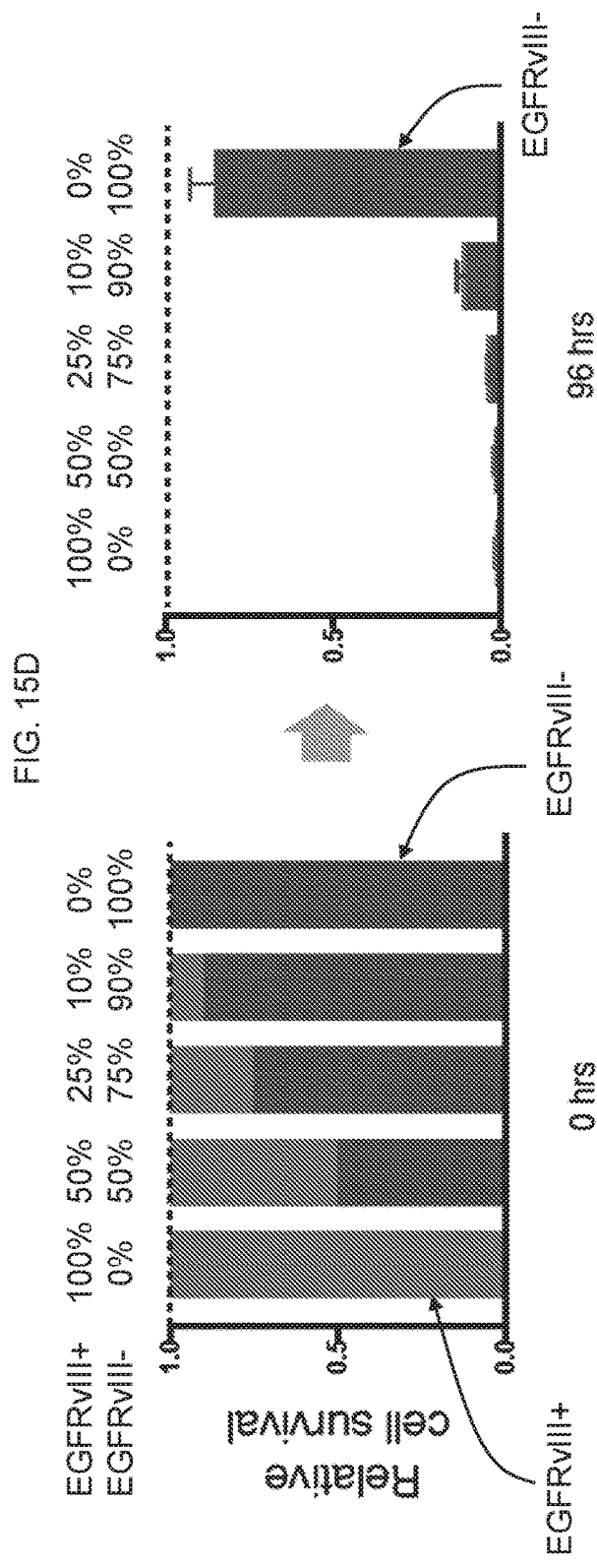

T cells engineered to contain the circuit described above were incubated with priming cells only, various mixtures of priming cells and target cells, or target cells only. Specifically, primary CD8+ synNotch split CAR T cells (schematically depicted in FIG. 15A) were co-cultured with the U87 cells described in FIG. 15B. FIG. 15C provides forward (FSC) and side scatter (SSC) flow cytometry plots after 96 hr co-culture of CD8+ synNotch split CAR T cells with the U87 priming cells (EGFRvIII+) only, target cells (EGFRvIII-) only and various mixtures of priming and target cells. The live U87 (i.e., "GBM") cells are identified in the indicated circled gates. FACS histograms showed only minimal killing of U87 cells in the absence of priming cells. However, significant killing of both priming and target cells was observed with as low as 10% priming cells (EGFRvIII+) in the priming/target cell mixture. FIG. 15D provides quantification related to FIG. 15C, specifically, quantification of CD8+ anti-EGFRvIII synNotch split CAR T cell killing as a function of priming/target cell ratio as shown in FIG. 15C.

Collectively, the data provided in this example demonstrates killing of GBM cells through the specific activation of a 2-receptor IF/THEN gate dependent upon the presence of EGFRvIII+ priming cells. In this embodiment, relatively small numbers (e.g., 10% of the population) of EGFRvIII+ priming cells were sufficient to induce widespread killing of targeted GBM cells whether or not the targeted cells express EGFRvIII.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a subject for an epidermal growth factor receptor variant III (EGFRvIII) positive glioblastoma, the method comprising:
    administering to the subject an immune cell genetically modified with:
    (a) a nucleic acid sequence encoding a binding triggered transcriptional switch (BTTS) that binds to EGFRvIII;
    (b) a nucleic acid sequence encoding a tandem chimeric antigen receptor (CAR) or a T cell receptor (TCR), wherein the tandem CAR or TCR comprises a first binding domain that recognizes Ephrin type-A receptor 2 (EphA2) and a second binding domain that recognizes IL-13 receptor α2 (IL-13Rα2); and
    (c) a regulatory sequence operably linked to (b) that is responsive to the BTTS;
    wherein binding of the BTTS to EGFRvIII on EGFRvIII positive glioblastoma cells activates expression of the tandem CAR or TCR, which binds to EphA2 and/or IL-13Rα2 in the EGFRvIII positive glioblastoma and induces killing of tumor cells in the EGFRvIII positive glioblastoma.

2. The method according to claim 1, wherein the BTTS is a SynNotch polypeptide.

3. The method according to claim 1, wherein the immune cell is a lymphoid cell.

4. The method according to claim 3, wherein the lymphoid cell is selected from the group consisting of: a T lymphocyte, a B lymphocyte and a Natural Killer cell.

5. The method of claim 1, wherein the subject is a human subject.

6. The method of claim 1, wherein the immune cell is a cytotoxic T cell.

7. The method of claim 1, wherein the BTTS comprises:
    an extracellular domain that comprises binding domains that bind to EGFRvIII;

a transmembrane domain,
one or more protease cleavage domains; and
a transcriptional activator,
wherein binding of the extracellular domains to EGFRvIII on EGFRvIII positive glioblastoma cells results in cleavage of the BTTS at the one or more protease cleavage domains to release the transcriptional activator, and wherein the released transcriptional activator binds to the regulatory sequence of (c) and activates expression of the tandem chimeric antigen receptor (CAR) or T cell receptor (TCR).

8. The method of claim 1, wherein the nucleic acid sequence of (b) encodes the tandem CAR.

* * * * *